US011535866B2

(12) United States Patent
Wilson et al.

(10) Patent No.: US 11,535,866 B2
(45) Date of Patent: Dec. 27, 2022

(54) GENE THERAPY FOR TREATING CITRULLENEMIA

(71) Applicant: The Trustees of the University of Pennsylvania, Philadelphia, PA (US)

(72) Inventors: James M. Wilson, Philadelphia, PA (US); Jenny Agnes Sidrane, Phoenixville, PA (US); Lili Wang, Phoenixville, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 402 days.

(21) Appl. No.: 16/478,971

(22) PCT Filed: Feb. 1, 2018

(86) PCT No.: PCT/US2018/016413
§ 371 (c)(1),
(2) Date: Jul. 18, 2019

(87) PCT Pub. No.: WO2018/144709
PCT Pub. Date: Aug. 9, 2018

(65) Prior Publication Data

US 2019/0352668 A1 Nov. 21, 2019

Related U.S. Application Data

(60) Provisional application No. 62/453,424, filed on Feb. 1, 2017, provisional application No. 62/469,650, filed on Mar. 10, 2017.

(51) Int. Cl.
*A61K 48/00* (2006.01)
*C12N 15/86* (2006.01)
*A61P 43/00* (2006.01)

(52) U.S. Cl.
CPC .............. *C12N 15/86* (2013.01); *A61P 43/00* (2018.01); *C12Y 603/04005* (2013.01); *A61K 48/00* (2013.01); *C12N 2750/14143* (2013.01); *C12N 2830/008* (2013.01); *C12N 2830/42* (2013.01)

(58) Field of Classification Search
CPC .... A61K 48/00; A61K 48/0058; C12N 15/86; C12N 2750/14143; C12N 2830/008; C12N 2830/42; C12Y 603/04005
See application file for complete search history.

(56) References Cited

U.S. PATENT DOCUMENTS

2006/0136184 A1 6/2006 Gustafsson et al.
2014/0032186 A1 1/2014 Gustafsson et al.
2015/0315612 A1 11/2015 Wilson et al.
2015/0376144 A1* 12/2015 DeRosa ............. A61K 31/7105 424/450

FOREIGN PATENT DOCUMENTS

WO WO 2003/052051 6/2003
WO WO 2005/033321 4/2005
WO WO 2011/126808 10/2011
WO WO 2013/049493 4/2013
WO WO 2015/012924 1/2015
WO WO 2017/015102 1/2017
WO WO 2017/100676 6/2017

OTHER PUBLICATIONS

Chandler etal, Gene Therapy 20: 1188-1191, 2013.*
Addgene, James Wilson lab deposit, pENN.AAV.TBG.PI.RBG.*
Castel hano-Carlos etal, Laboratory Animals 44: 88-103, 2010.*
Calcedo et al., Worldwide Epidemiology of Neutralizing Antibodies to Adeno-Associated Viruses. J Infect Dis. Feb. 1, 2009;199(3):381-90.
Chandler et al., Liver-directed adeno-associated virus serotype 8 gene transfer rescues a lethal murine model of citrullinemia type 1. Gene Ther. Dec. 2013;20(12):1188-91. Epub Oct. 17, 2013.
Engel et al., Mutations and polymorphisms in the human argininosuccinate synthetase (ASS1) gene. Hum Mutat. Mar. 2009;30(3):300-7.
Gao et al., Adeno-associated viruses undergo substantial evolution in primates during natural infections. Proc Natl Acad Sci U S A. May 13, 2003;100(10):6081-6. Epub Apr. 25, 2003.
GenBank Accession: AF513852.1, Adeno-associated virus 8 nonstructural protein and capsid protein genes, complete cds, Sep. 5, 2002.
Grimm et al., Titration of AAV-2 particles via a novel capsid ELISA: packaging of genomes can limit production of recombinant AAV-2. Gene Ther. Jul. 1999;6(7): 1322-30.
Kelly et al., Splicing of many human genes involves sites embedded within introns. Nucleic Acids Res. May 19, 2015;43(9):4721-32, Epub Apr. 20, 2015.
Kobayashi et al. Messenger RNA coding for argininosuccinate synthetase in citrullinemia. Am J Hum Genet. May 1986;3 8(5):667-80.
Kok et al., Adeno-associated virus-mediated rescue of neonatal lethality in argininosuccinate synthetase-deficient mice. Mol Ther. Oct. 2013;21(10):1823-31. doi: 10.1038/mt.2013.139. Epub Jul. 2, 2013.
Lock et al., Absolute determination of single-stranded and self-complementary adeno-associated viral vector genome titers by droplet digital PCR. Hum Gene Ther Methods. Apr. 2014;25(2):115-25, Epub Feb. 1, 20144.
Miyatake et al., Transcriptional targeting of herpes simplex virus for cell-specific replication, J Virol, Jul. 1997;71(7):5124-32.
NCBI Reference Sequence: YP_077180.1, capsid protein [Adeno-associated virus—8], Mar. 11, 2010.
Saheki et al., Qualitative and quantitative abnormalities of argininosuccinate synthetase in citrullinemia. Clin Chim Acta. Feb. 5, 1981;109(3):325-3 5.

(Continued)

*Primary Examiner* — Kevin K Hill
(74) *Attorney, Agent, or Firm* — Howson & Howson LLP

(57) ABSTRACT

Compositions and regimens useful in treating type I citrullenemia are provided. The compositions include recombinant adeno-associated virus (rAAV) with a transthyretin enhancer and promoter driving expression of a human Argininosuccinate Synthase 1 (ASS1).

20 Claims, 18 Drawing Sheets

Specification includes a Sequence Listing.

(56) References Cited

OTHER PUBLICATIONS

Sandig et al., HBV-derived promoters direct liver-specific expression of an adenovirally transduced LDL receptor gene. Gene Ther, Nov. 1996;3(11):1002-9.
SHEPELEV and FEDOROV. Advances in the Exon-Intron Database. Brief Bioinform, Jun. 2006;7(2):178-85, Epub Mar. 9, 2006.
Sommer et al., Quantification of adeno-associated virus particles and empty capsids by optical density measurement. Mol Ther. Jan. 2003;7(1): 122-8.
Thompson et al., A comprehensive comparison of multiple sequence alignments, Nucleic Acids Res. Jul. 1, 1999;27(13):2682-90.
Wobus et al., Monoclonal antibodies against the adeno-associated vims type 2 (AAV-2) capsid: epitope mapping and identification of capsid domains involved in AAV-2-cell interaction and neutralization of AAV-2 infection. J Virol. Oct. 2000;74(19):9281-93.
Wu et al., Effect of genome size on AAV vector packaging. Mol Ther. Jan. 2010;18(1):80-6. Epub Nov. 10, 2009.
Wu et al., Optimization of self-complementary AAV vectors for liver-directed expression results in sustained correction of hemophilia B at low vector dose. Mol Ther. Feb. 2008;16(2):280-9, Epub Dec. 4, 2007.
Search Report and Written Opinion in International Patent Application No. PCT/US18/16413, dated Oct. 4, 2018.

* cited by examiner

MAP of pAAV8.ApoE.A1AT(full).IVS2.hASS1co.bGH.

FIG. 11A - Male
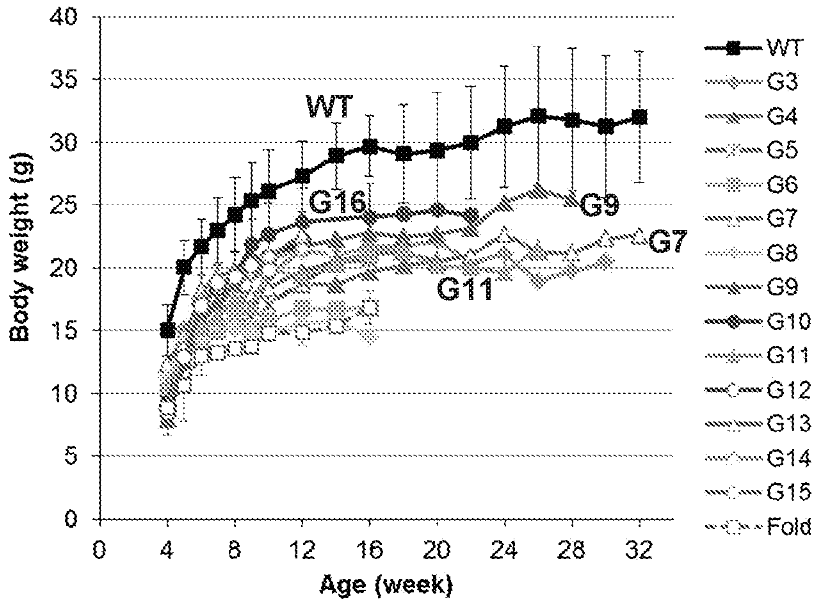
FIG. 11B - Female
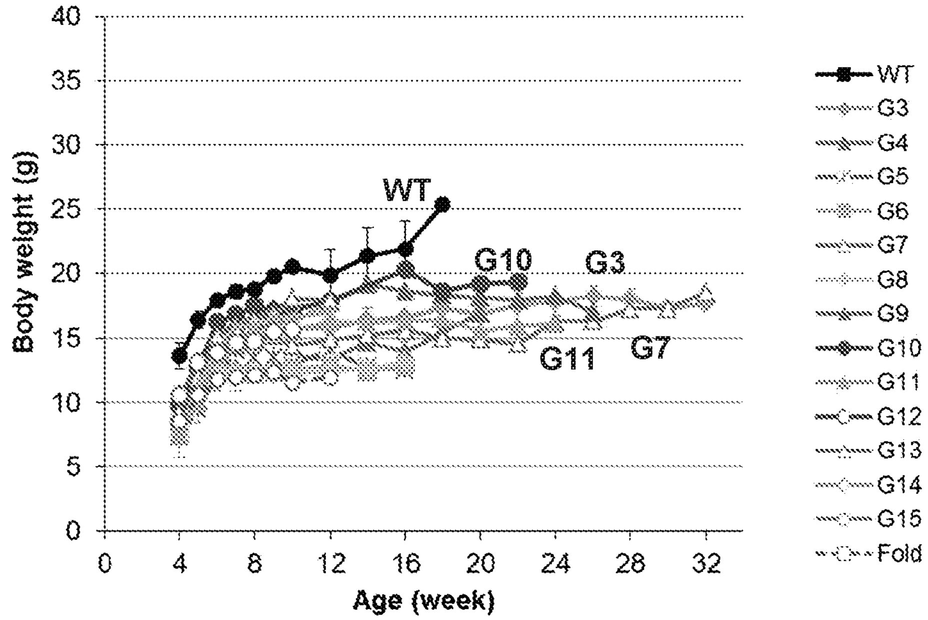

FIG. 12A – 2 Weeks
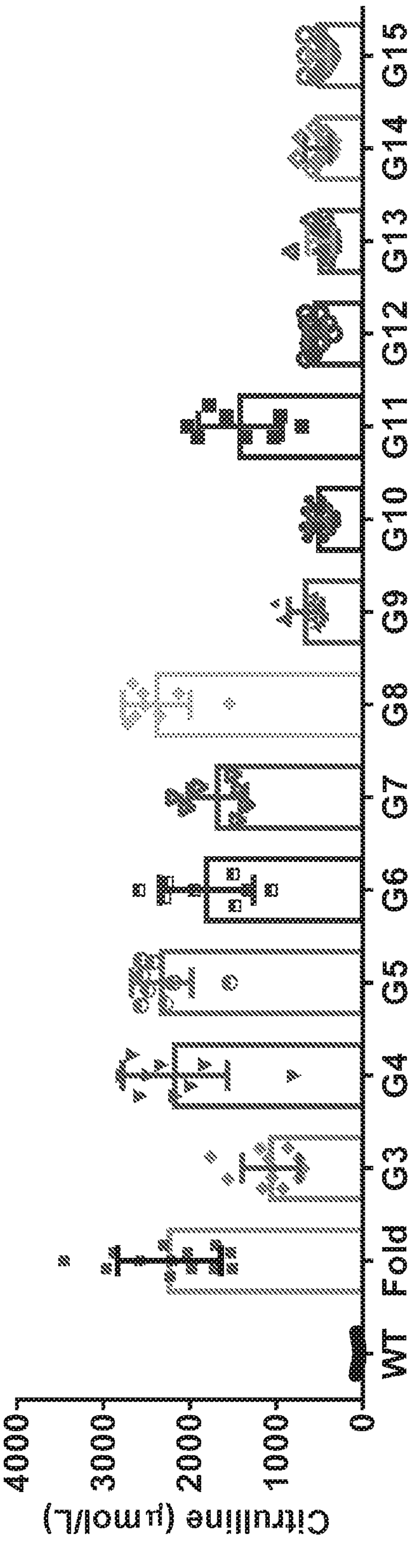
FIG. 12B – 6 Weeks
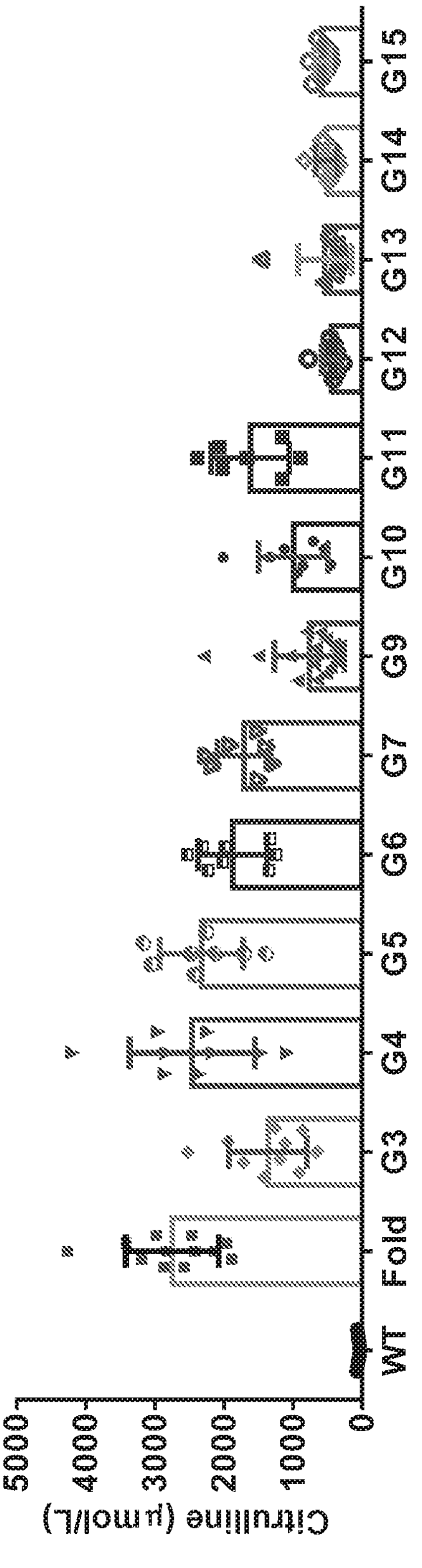

GENE THERAPY FOR TREATING CITRULLENEMIA

CROSS-REFERENCE TO RELATED APPLICATIONS

This is a National Stage Entry under 35 U.S.C. 371 of International Patent Application No. PCT/US2018/016413, filed Feb. 1, 2018, which claims priority to U.S. Provisional Patent Application No. 62/453,424, filed Feb. 1, 2017, and U.S. Provisional Patent Application No. 62/469,650, filed Mar. 10, 2017. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "16-7938PCT_Seq_Listing_ST25.txt".

1. BACKGROUND

The application relates to embodiments useful for a gene therapy for treating type I citrullenemia. Type I citrullenemia is an autosomal recessive disease caused by mutations in argininosuccinate synthase 1 (ASS1) enzyme that catalyzes the synthesis of argininosuccinate from citrulline and aspartate, resulting in citrullinemia and buildup of ammonia.

The clinical spectrum of Type I citrullenemia (CTLN1) ranges from severe neonatal onset form to milder late-onset forms. Owing to its relatively recent addition to the newborn screening panel, patients with type I citrullinemia will be identified early, allowing immediate implementation of treatment. However, despite this early identification of disease and treatment, some patients may progress. The untreated mortality rate in untreated classical CTLN1 is 100%, with most deaths occurring before 17 days of life.

Current treatment approaches for type I citrullenemia include dietary restriction (restriction of protein intake), medications (nitrogen scavenger therapy and carnitine), and arginine supplementation. Liver transplantation is curative for citrullinemia but transplant recipients are required to maintain a constant immune suppression regimen to prevent rejection. Liver directed AAV treatments for type I citrullenemia have been shown. See, e.g., Chandler et al, Liver-directed adeno-associated virus serotype 8 gene transfer rescues a lethal murine model of citrullinemia type 1, Gene Therapy (2013) 20, 1188-1191, which is incorporated herein by reference. However, liver-directed gene therapy did not fully correct the biochemical phenotype of systemic ASS1 deficiency; arginine levels plummeted in treated individuals of a murine model for CTLN1 (fold/fold) due to persistent renal deficiency. See also, Kok et al, Adeno-associated Virus-mediated Rescue of Neonatal Lethality in Argininosuccinate Synthase-deficient Mice, Molecular Therapy vol. 21 no. 10, 1823-1831, October 2013, which is incorporated herein by reference.

What are needed are more effective treatments for type 1 citrullinemia.

2. SUMMARY

The embodiments described herein relate to an AAV gene therapy vector for delivering normal human Argininosuccinate Synthase 1 (ASS1) to a subject in need thereof, following intravenous administration of the vector resulting in long-term, perhaps 10 years or more, of clinically meaningful correction of Type I citrullenemia (CTLN1) (also sometimes called citrullinuria or ASS1 deficiency). The subject patient population is patients with moderate to severe Type I citrullenemia, including those with the acute neonatal form (the "classic" form), a milder late-onset form (the "non-classic" form), or the form in which women have onset of severe symptoms during pregnancy or post-partum. The intended vector dose is, in one embodiment, intended to deliver ASS1 which results in near normal citrulline, glutamine and ammonia plasma levels. However, even nominal reductions in citrulline, glutamine and ammonia levels are desirable, and a desirable endpoint. As reported by Quinonez and Thoene, Pagon R A, Adam M P, Ardinger H H, et al., editors. Seattle (Wash.): University of Washington, Seattle; 1993-2016 (incorporated herein by reference), elevation of either citrulline or ammonia above acceptable levels (ammonia>100 μmol/L or plasma citrulline>~100 μmol/L) is sufficient evidence to initiate treatment for CTLN1. In another embodiment, a neonatal diagnosis based on genetic testing is sufficient to initiate treatment.

In one aspect, this application provides the use of a replication deficient adeno-associated virus (AAV) to deliver a human Argininosuccinate Synthase 1 (hASS1) gene to liver cells of patients (human subjects) diagnosed with CTLN1. The recombinant AAV vector (rAAV) used for delivering the hASS1 gene ("rAAV.hASS1") should have a tropism for the liver (e.g., a rAAV bearing an AAV8 capsid), and the hASS1 transgene should be controlled by liver-specific expression control elements. In one embodiment, the expression control elements include one or more of the following: an enhancer; a promoter; an intron; a WPRE; and a polyA signal. Such elements are further described herein.

In one embodiment, the ASS1 protein sequence is shown in SEQ ID NO: 1. In one embodiment, the hASS1 coding sequence is shown in SEQ ID NO: 3. The coding sequence for hASS1 is, in one embodiment, codon optimized for expression in humans. Such sequence may share at least 80% identity to the native hASS1 coding sequence (SEQ ID NO: 3). In another embodiment, the hASS1 coding sequence is that shown in SEQ ID NO: 3.

In another aspect, provided herein is an aqueous suspension suitable for administration to a CTLN1 patient which includes the rAAV described herein. In some embodiments, the suspension includes an aqueous suspending liquid and about $1\times10^{12}$ to about $1\times10^{14}$ genome copies (GC) of the rAAV/mL. The suspension is, in one embodiment, suitable for intravenous injection. In other embodiment, the suspension further includes a surfactant, preservative, and/or buffer dissolved in the aqueous suspending liquid.

In another embodiment, provided herein is a method of treating a patient having CTLN1 with an rAAV as described herein. In one embodiment, about $1\times10^{11}$ to about $3\times10^{13}$ genome copies (GC) of the rAAV/kg patient body weight are delivered the patient in an aqueous suspension.

3. BRIEF DESCRIPTION OF THE DRAWINGS

Figure 2A:
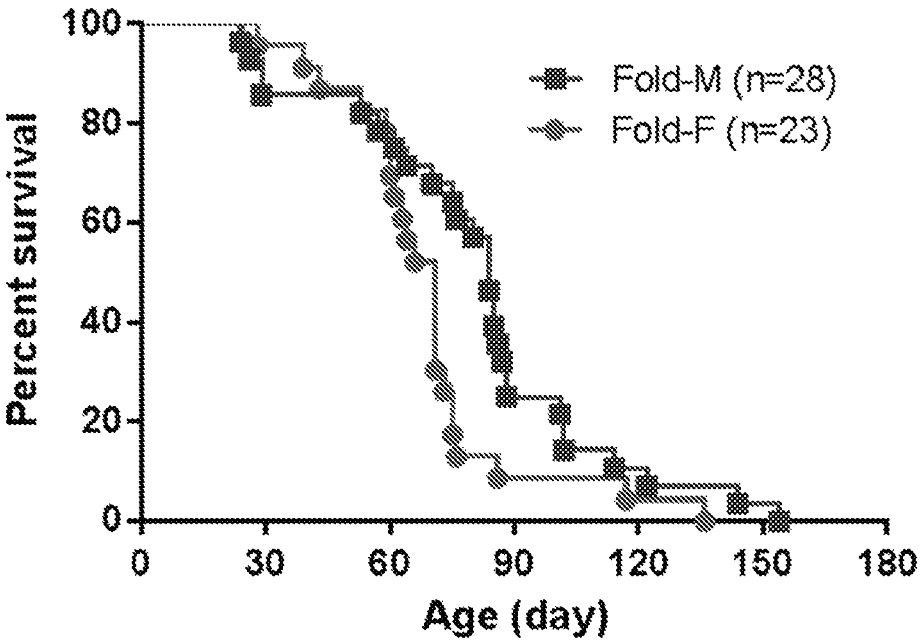
FIG. 2A is a survival curve of ASS1$^{fold/fold}$ mice as described in Example 2. Squares are male mice and circles are female mice.
Figure 2B:
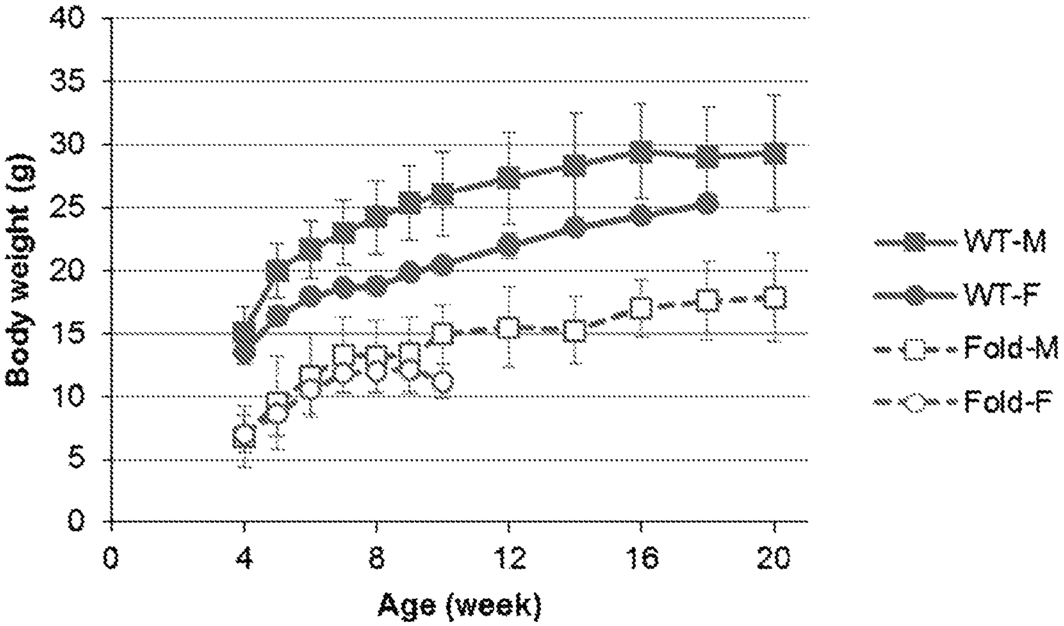

FIG. 2B is a line graph of body weights in both genders (M, male; F, female) of ASS1$^{fold/fold}$ mice (Fold). Wild-type littermates (WT) were provided as controls.

Figure 2C:
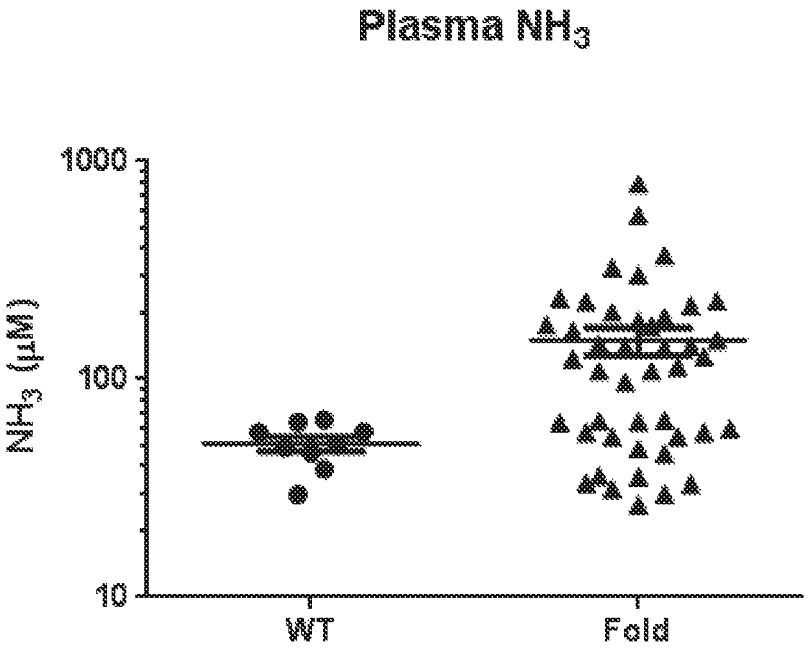

FIG. 2C is a graph showing elevated plasma NH3 levels of ASS1$^{fold/fold}$ mice. Wild-type (WT) mice were provided as controls. Each circle or triangle indicates one sample. Mean±SEM is also plotted. Mann Whitney test was performed and the p value between indicated groups is shown in the figure.

Figure 2D:
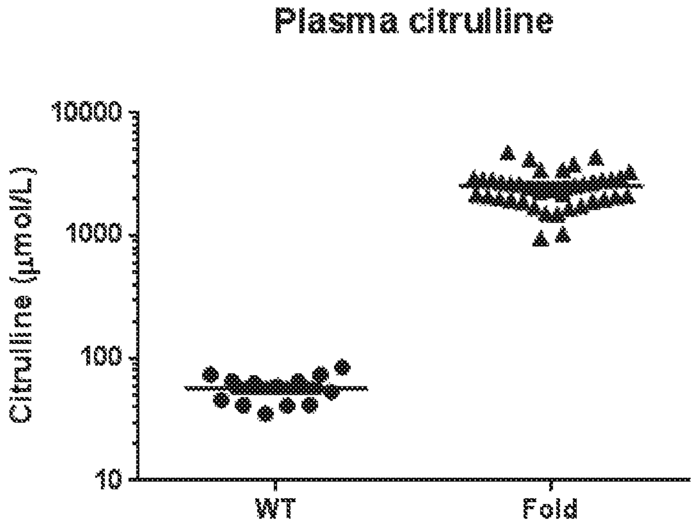

FIG. 2D is a graph showing elevated plasma citrulline levels of ASS1$^{fold/fold}$ mice. Wild-type (WT) mice were provided as controls. Each circle or triangle indicates one sample. Mean±SEM is also plotted. Mann Whitney test was performed and the p value between indicated groups is shown in the figure.

Figure 2E:
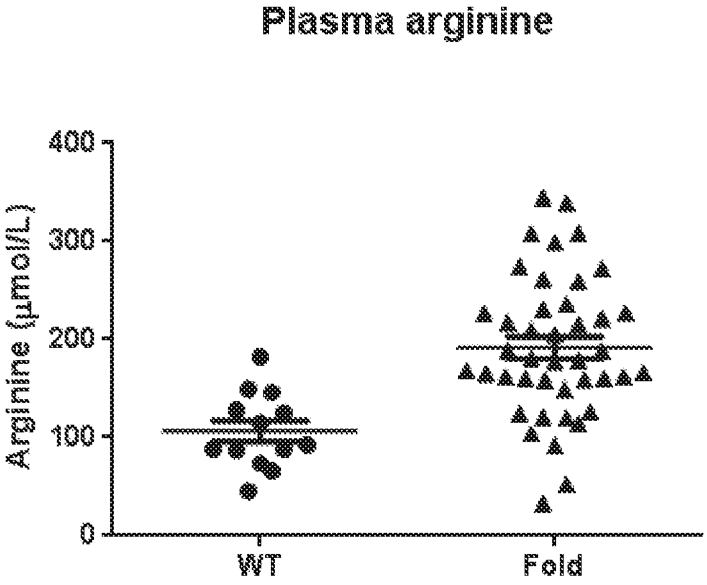

FIG. 2E is a graph showing elevated plasma arginine levels of ASS1$^{fold/fold}$ mice. Wild-type (WT) mice were provided as controls. Each circle or triangle indicates one sample. Mean±SEM is also plotted. Mann Whitney test was performed and the p value between indicated groups is shown in the figure.

Figure 2F:
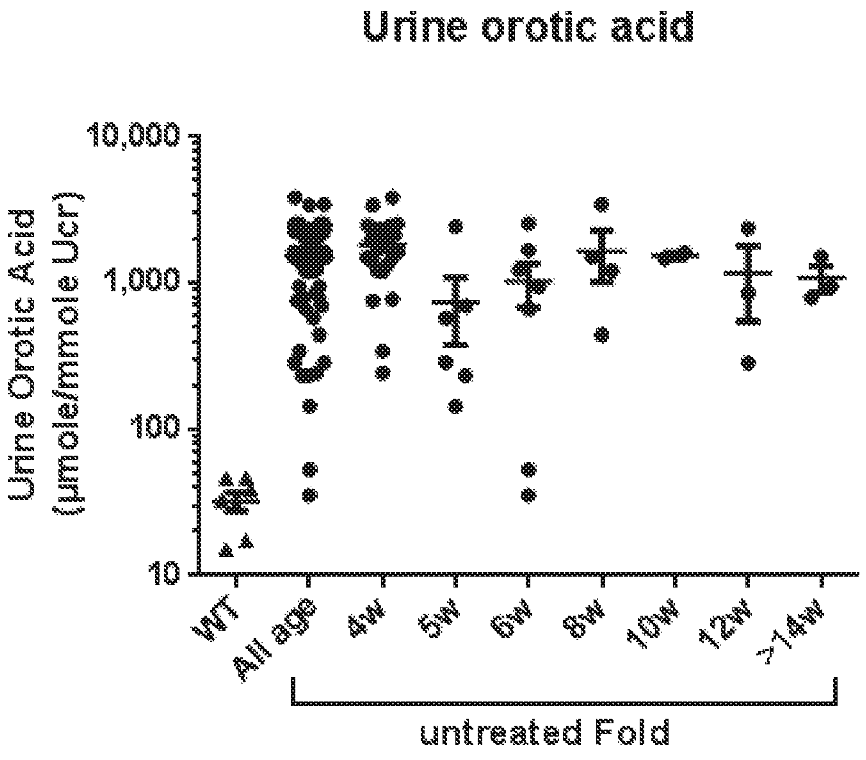

FIG. 2F is a graph showing elevated urine orotic acid levels of ASS1$^{fold/fold}$ mice at all age, or at the age of 4 weeks, 5 weeks, 6 weeks, 8 weeks, 10 weeks, 12 weeks and 14 weeks and older. Wild-type (WT) mice were provided as controls. Each dot indicates one sample. Mean±SEM is also plotted.

Figure 3A:
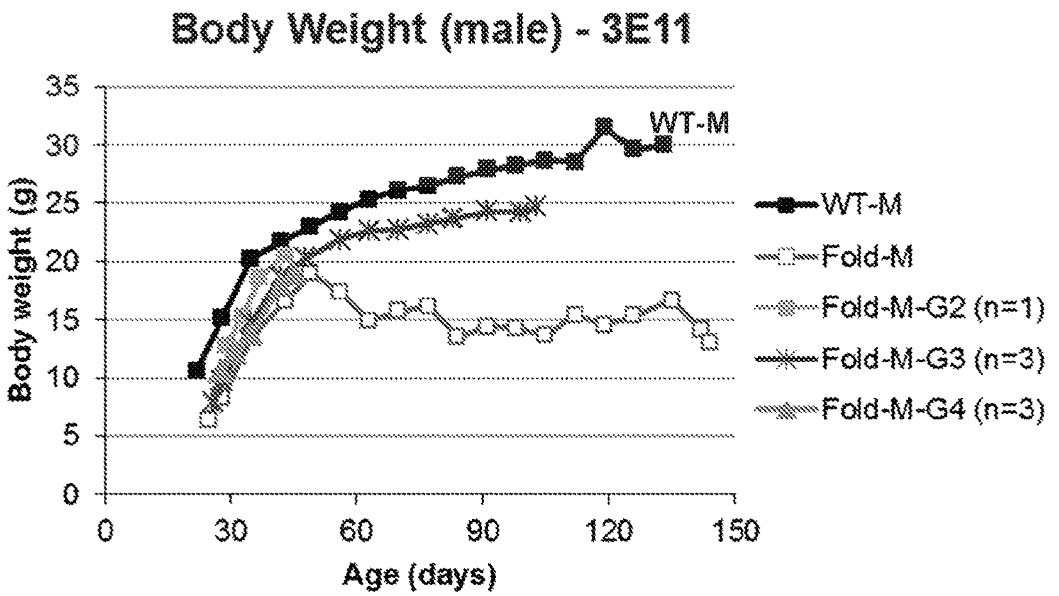

FIG. 3A is a line graph of body weights of male ASS1$^{fold/fold}$ mice injected intravenously at birth with $3\times10^{11}$ GC/pup of AAV8.TBG.PI.hASS1co.WPRE.bGH (Fold-M-G2, solid gray square, n=1) or AAV8.LSP.IVS2.hASS1co.bGH (Fold-M-G3, asterisk, n=3) or AAV8.TBG.PI.hASS1co.bGH (Fold-M-G4, triangle, n=3). Male ASS1$^{fold/fold}$ (Fold-M, open square) and wild-type (WT-M, solid black square) mice without treatment were provided as controls.

Figure 3B:
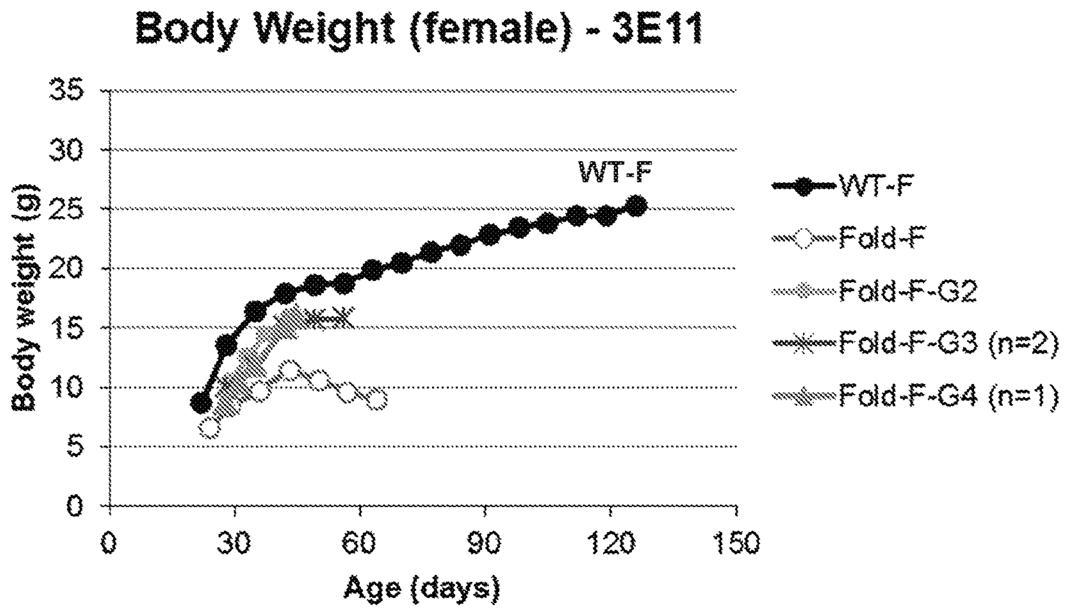

FIG. 3B is a line graph of body weights of female ASS1$^{fold/fold}$ mice injected intravenously at birth with $3\times10^{11}$ GC/pup of AAV8.TBG.PI.hASS1co.WPRE.bGH (Fold-F-G2, solid grey circle, n=1) or AAV8.LSP.IVS2.hASS1co.bGH (Fold-F-G3, asterisk, n=2) or AAV8.TBG.PI.hASS1co.bGH (Fold-F-G4, triangle, n=1). Female ASS1$^{fold/fold}$ (Fold-F, open circle) and wild-type (WT-F, solid black circle) mice without treatment were provided as controls.

Figure 3C:
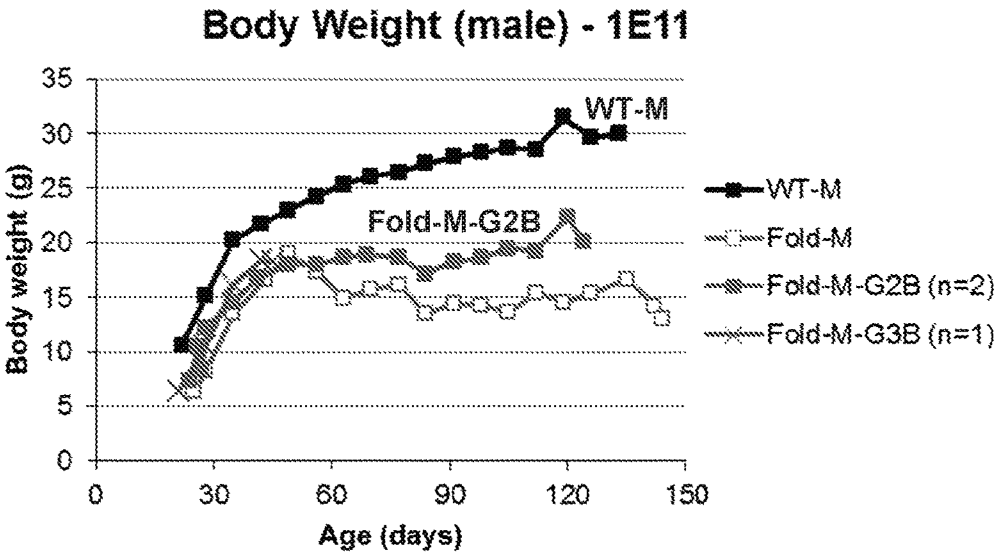

FIG. 3C is a line graph of body weights of male ASS1$^{fold/fold}$ mice injected intravenously at birth with $1\times10^{11}$ GC/pup of AAV8.TBG.PI.hASS1co.WPRE.bGH (Fold-M-G2, red, n=2) or AAV8.LSP.IVS2.hASS1co.bGH (Fold-M-G3, purple, n=1). Male ASS1$^{fold/fold}$ (Fold-M, blue) and wild-type (WT-M, black) mice without treatment were provided as controls.

Figure 3D:
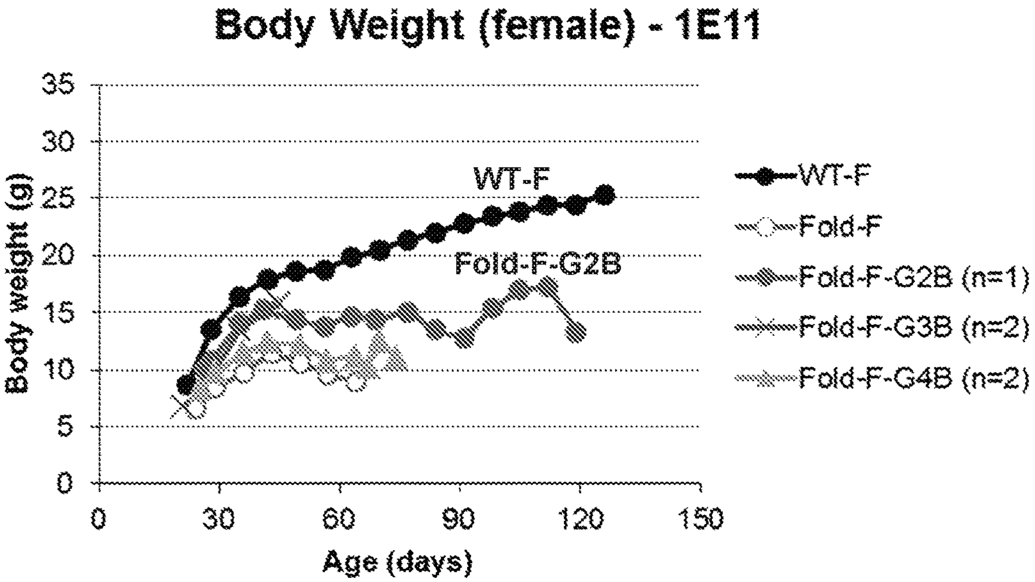

FIG. 3D is a line graph of body weights of female ASS1$^{fold/fold}$ mice injected intravenously at birth with $1\times10^{11}$ GC/pup of AAV8.TBG.PI.hASS1co.WPRE.bGH (Fold-F-G2, red, n=1) or AAV8.LSP.IVS2.hASS1co.bGH (Fold-F-G3, purple, n=2) or AAV8.TBG.PI.hASS1co.bGH (Fold-F-G4, green, n=2). Female ASS1$^{fold/fold}$ (Fold-F, blue) and wild-type (WT-F, black) mice without treatment were provided as controls.

Figure 3E:
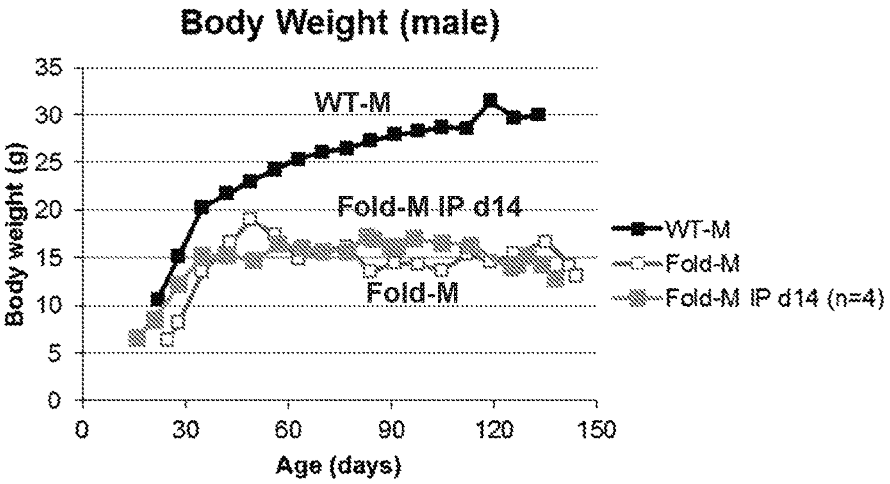

FIG. 3E is a line graph of body weights of male ASS1$^{fold/fold}$ mice injected intraperitoneal on postnatal day 14 with $1\times10^{11}$ GC/mouse of AAV8.TBG.PI.hASS1co.WPRE.bGH (Fold-M-IP d14, light blue, n=4). Male ASS1$^{fold/fold}$ (Fold-M, blue) and wild-type (WT-M, black) mice without treatment were provided as controls.

Figure 3F:
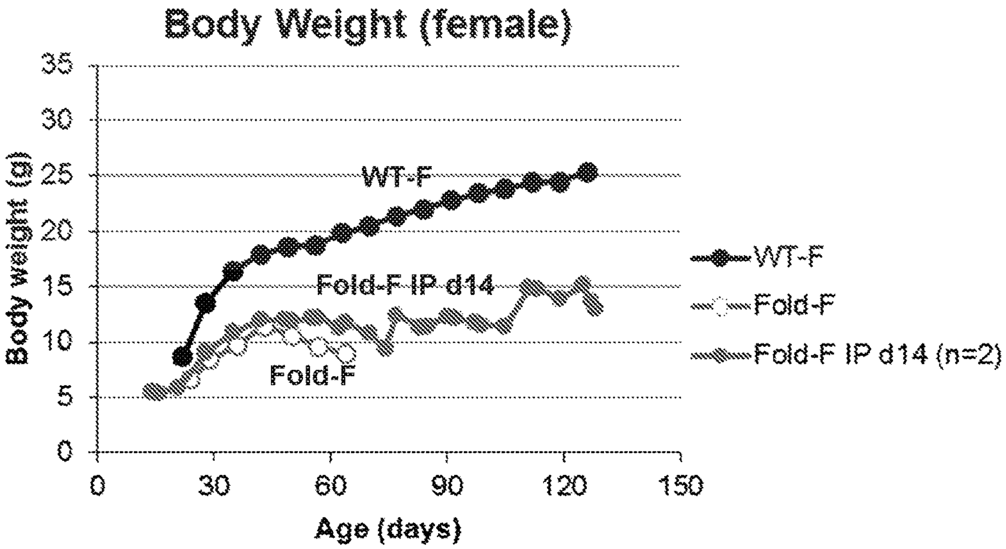

FIG. 3F is a line graph of body weights of female ASS1$^{fold/fold}$ mice injected intraperitoneal on postnatal day 14 with $1\times10^{11}$ GC/mouse of AAV8.TBG.PI.hASS1co.WPRE.bGH (Fold-F-IP d14, magenta, n=2). Female ASS1$^{fold/fold}$ (Fold-F, blue) and wild-type (WT-F, black) mice without treatment were provided as controls.

Figure 4A:
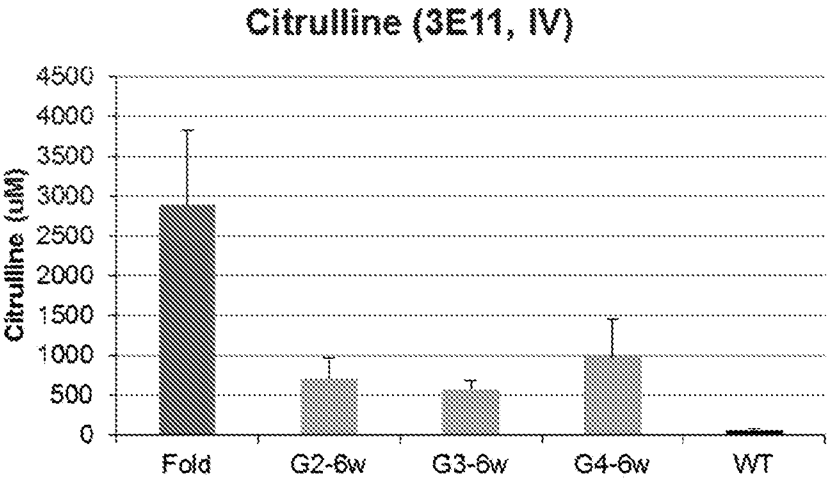

FIG. 4A is a bar graph of citrulline levels in the blood of ASS1$^{fold/fold}$ mice injected intravenously at birth with $3\times10^{11}$ GC/pup of AAV8.TBG.PI.hASS1co.WPRE.bGH (G2-6w) or AAV8.LSP.IVS2.hASS1co.bGH (G3-6w) or AAV8.TBG.PI.hASS1co.bGH (G4-6w). ASS1$^{fold/fold}$ (Fold) and wild-type (WT-M) mice without treatment were provided as controls.

Figure 4B:
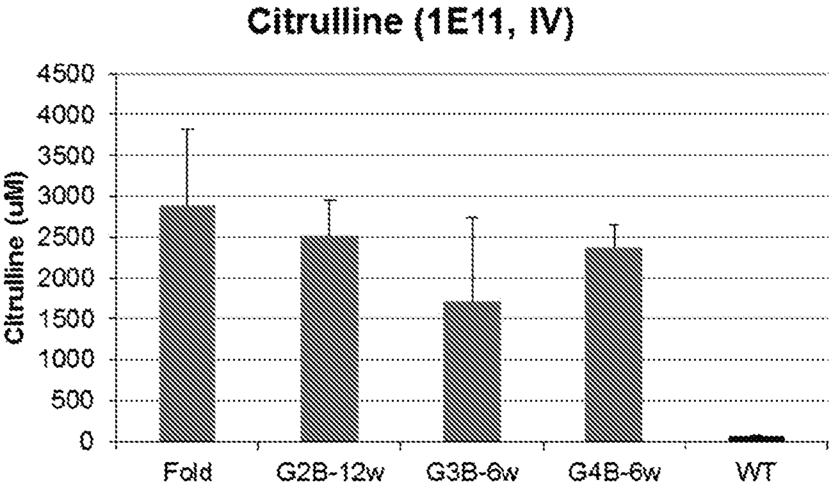

FIG. 4B is a bar graph of citrulline levels in the blood of ASS1$^{fold/fold}$ mice injected intravenously at birth with $1\times10^{11}$ GC/pup of AAV8.TBG.PI.hASS1co.WPRE.bGH (G2B-12w) or AAV8.LSP.IVS2.hASS co.bGH (G3B-6w) or AAV8.TBG.PI.hASS1co.bGH (G4B-6w). ASS1$^{fold/fold}$ (Fold) and wild-type (WT-M) mice without treatment were provided as controls.

Figure 5A:
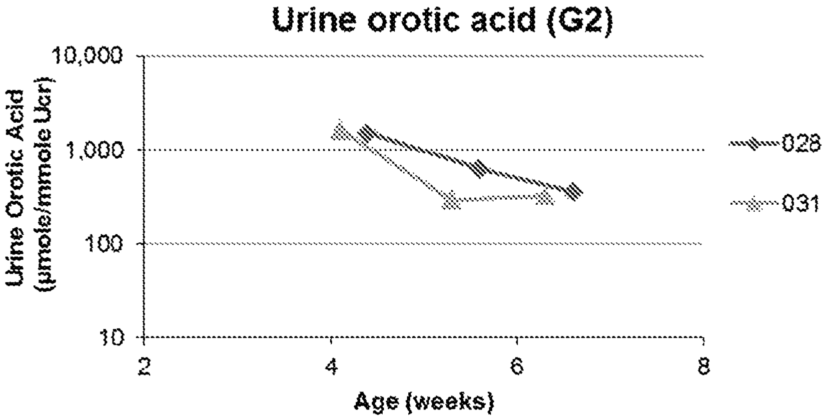

FIG. 5A is a line graph of urine orotic acid levels in ASS1$^{fold/fold}$ mice injected intravenously at birth with $3\times10^{11}$ GC/pup of AAV8.TBG.PI.hASS1co.WPRE.bGH. Data from mice with identification number 028 and 031 was acquired and plotted.

Figure 5B:
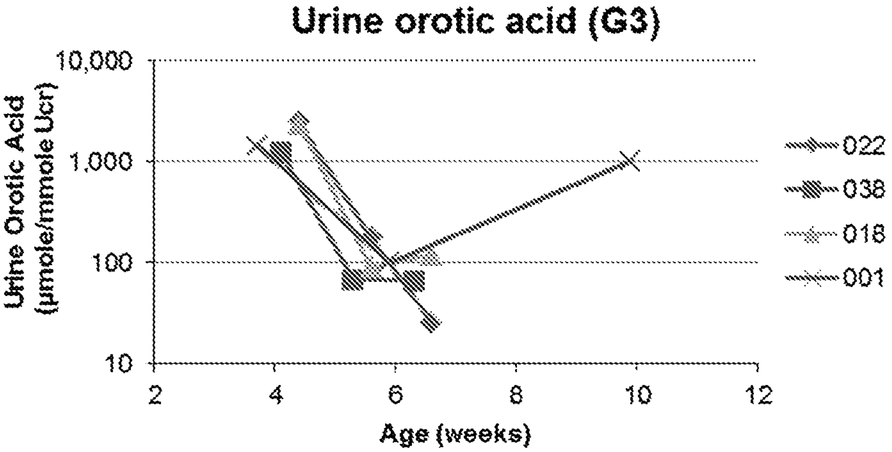

FIG. 5B is a line graph of urine orotic acid levels in ASS1$^{fold/fold}$ mice injected intravenously at birth with $3\times10^{11}$ GC/pup of AAV8.LSP.IVS2.hASS1co.bGH. Data from mice with identification number 022, 038, 018 and 001 was acquired and plotted.

Figure 5C:
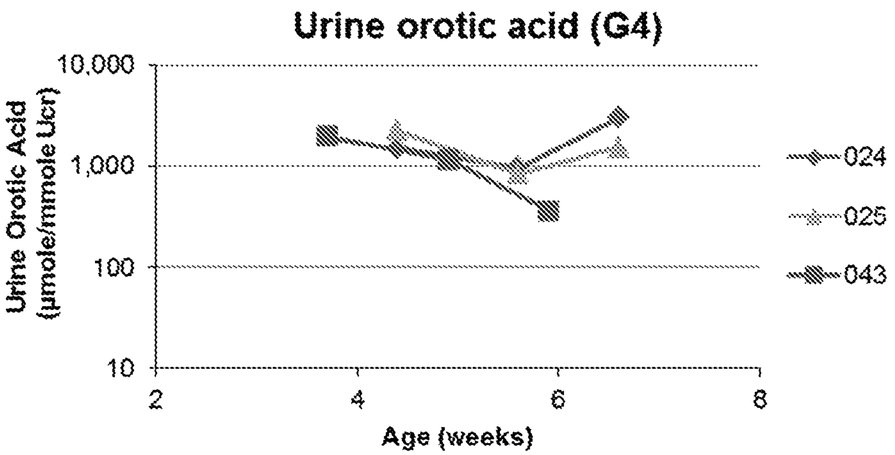

FIG. 5C is a line graph of urine orotic acid levels in ASS1$^{fold/fold}$ mice injected intravenously at birth with $3\times10^{11}$ GC/pup of AAV8.TBG.PI.hASS1co.bGH. Data from mice with identification number 024, 025 and 043 was acquired and plotted.

Figure 5D:
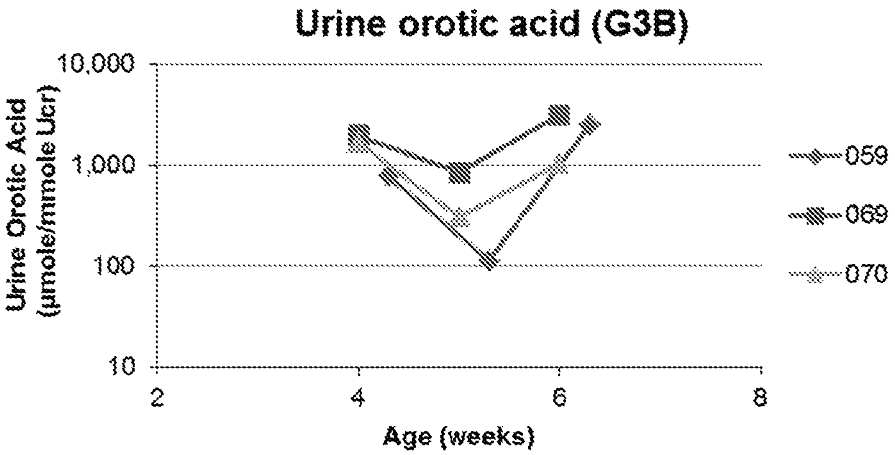

FIG. 5D is a line graph of urine orotic acid levels in ASS1$^{fold/fold}$ mice injected intravenously at birth with $1\times10^{11}$ GC/pup of AAV8.LSP.IVS2.hASS1co.bGH. Data from mice with identification number 059, 069 and 070 was acquired and plotted.

Figure 6A:
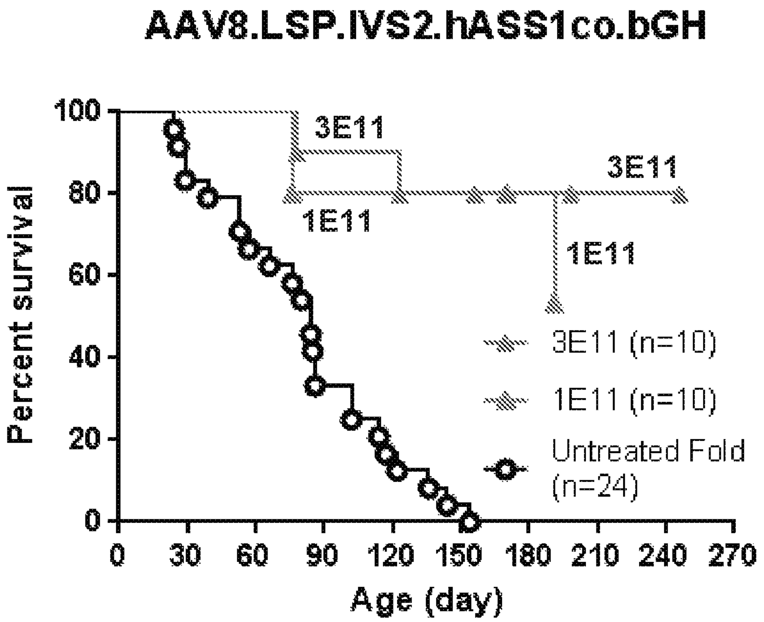

FIG. 6A is a survival curve of ASS1$^{fold/fold}$ mice demonstrating liver-directed gene therapy improves the survival of ASS1$^{fold/fold}$. Four-week old ASS1$^{fold/fold}$ (both males and females) received a single retro-orbital injection of AAV8.LSP.IVS.hASS1co.bGH vector at the dose of $3\times10^{11}$ GC/mouse (n=10) or $1\times10^{11}$ GC/mouse (n=10). Survival was monitored. Untreated ASS1$^{fold/fold}$ mice were provided as controls (n=24).

Figure 6B:
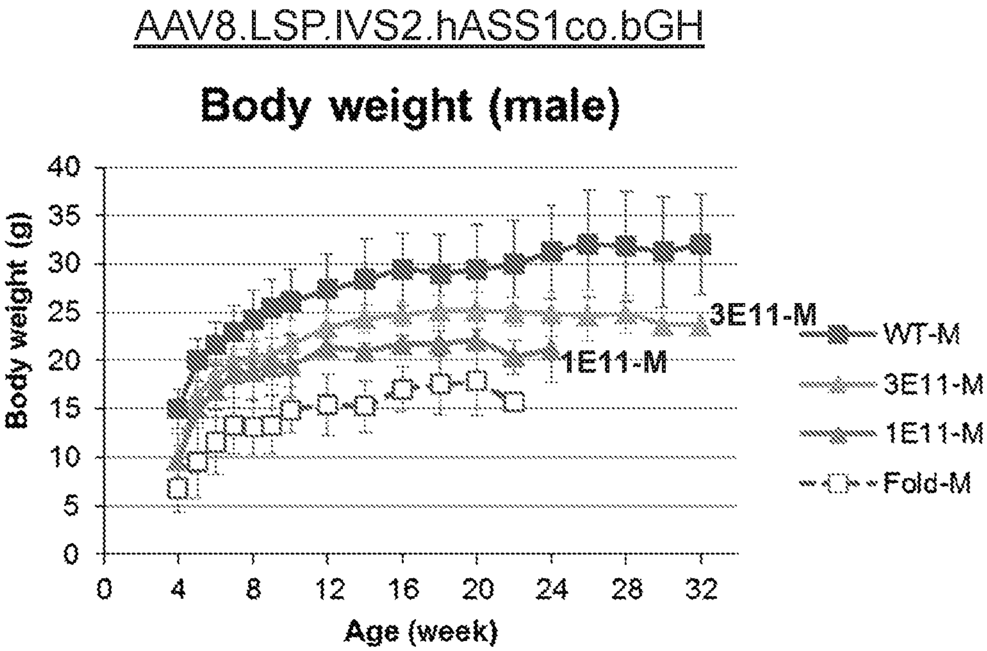

FIG. 6B is a line graph of body weights of male ASS1$^{fold/fold}$ mice demonstrating liver-directed gene therapy improves the body weight of ASS1$^{fold/fold}$. Four-week old ASS1$^{fold/fold}$ received a single retro-orbital injection of AAV8.LSP.IVS.hASS1 co.bGH vector at the dose of $3\times10^{11}$ GC/mouse or $1\times10^{11}$ GC/mouse. Body weights were monitored. Gender-matched untreated ASS1$^{fold/fold}$ (Fold) and wild-type (WT) mice were provided as controls.

Figure 6C:
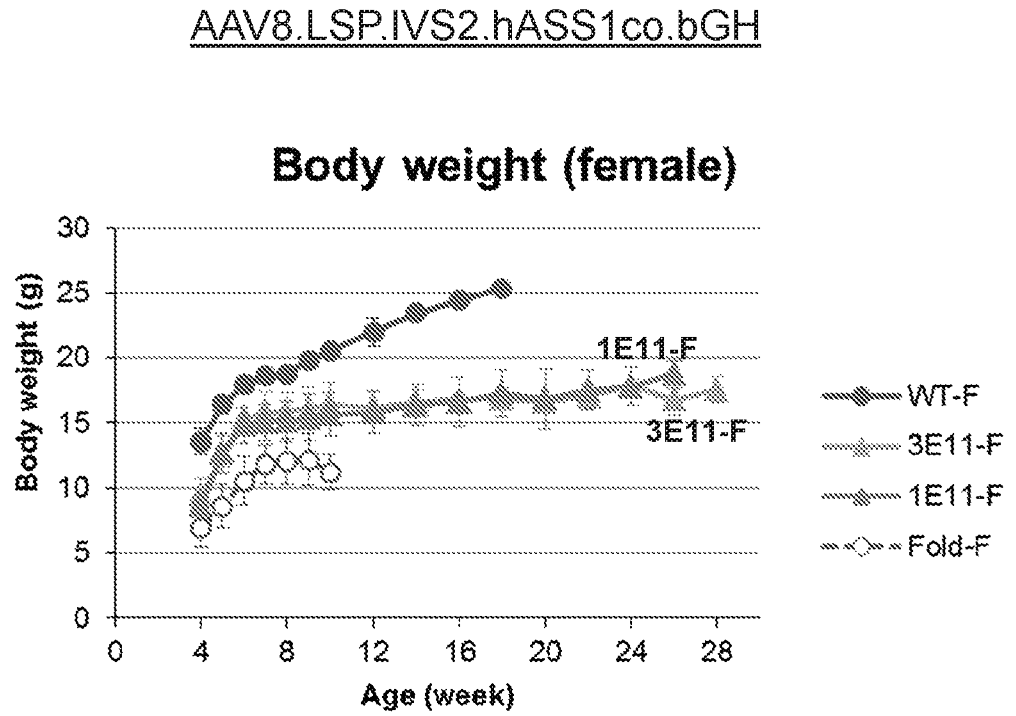

FIG. 6C is a line graph of body weights of female ASS1$^{fold/fold}$ mice demonstrating liver-directed gene therapy improves the body weight of ASS1$^{fold/fold}$ Four-week old ASS1$^{fold/fold}$ received a single retro-orbital injection of AAV8.LSP.IVS.hASS1co.bGH vector at the dose of $3\times10^{11}$ GC/mouse or $1\times10^{11}$ GC/mouse. Body weights were monitored. Gender-matched untreated ASS1$^{fold/fold}$ (Fold) and wild-type (WT) mice were provided as controls.

Figure 7A:
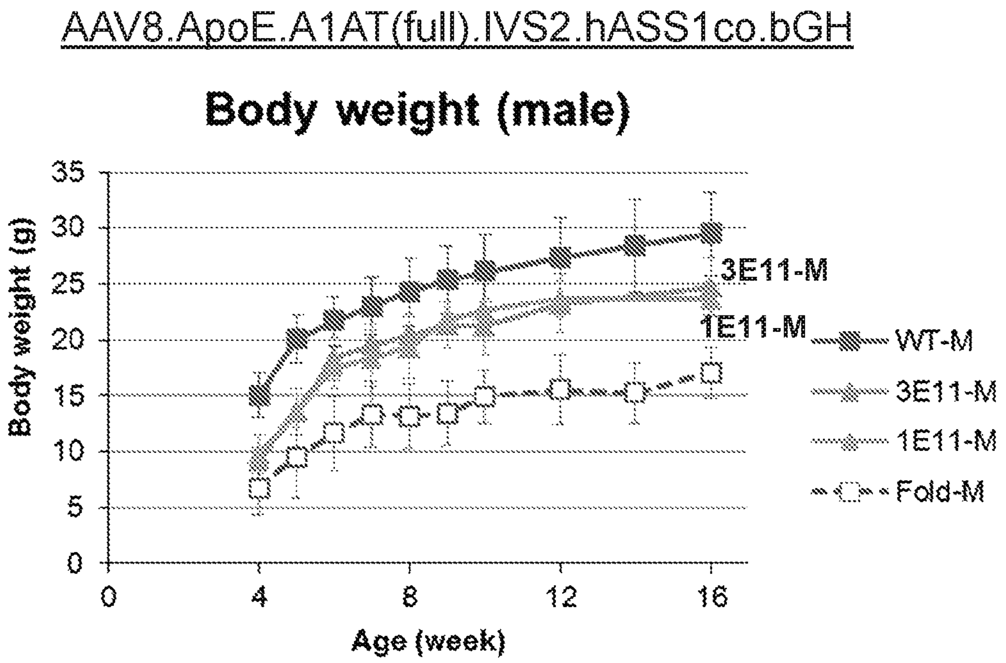

FIG. 7A is a line graph of body weights of male ASS1$^{fold/fold}$ mice demonstrating liver-directed gene therapy improves the body weight of ASS1$^{fold/fold}$. Four-week old ASS1$^{fold/fold}$ received a single retro-orbital injection of AAV8.ApoE.A1AT(full).IVS2.hASS1co.bGH vector at the dose of $3\times10^{11}$ GC/mouse or $1\times10^{11}$ GC/mouse. Body weights were monitored. Gender-matched untreated ASS1$^{fold/fold}$ (Fold) and wild-type (WT) mice were provided as controls.

Figure 7B:
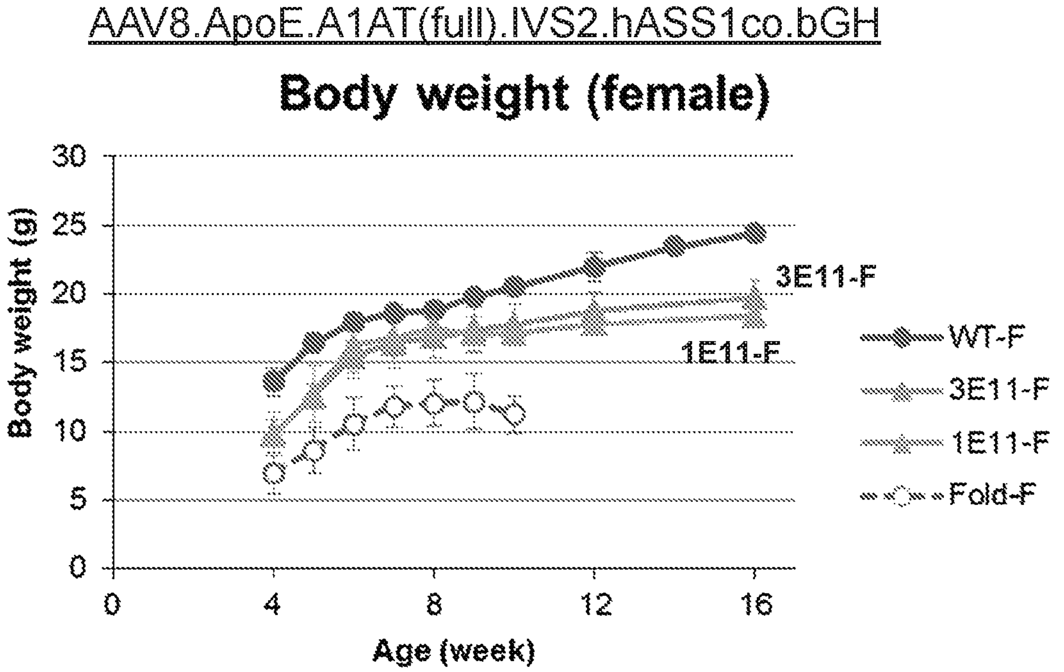

FIG. 7B is a line graph of body weights of female ASS1$^{fold/fold}$ mice demonstrating liver-directed gene therapy improves the body weight of ASS1$^{fold/fold}$ Four-week old ASS1$^{fold/fold}$ received a single retro-orbital injection of AAV8.ApoE.A1AT(full).IVS2.hASS1co.bGH vector at the dose of 3×10$^{11}$ GC/mouse or 1×10$^{11}$ GC/mouse. Body weights were monitored. Gender-matched untreated ASS1$^{fold/fold}$ (Fold) and wild-type (WT) mice were provided as controls.

Figure 8:
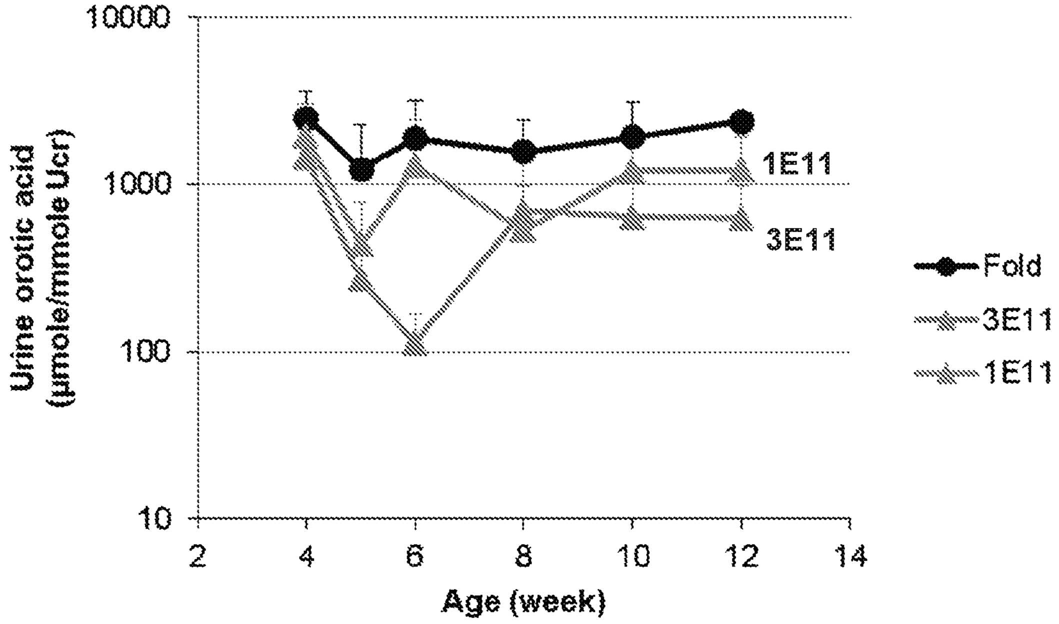

FIG. 8 is a line graph showing reduction of urine orotic acid in ASS1$^{fold/fold}$ following vector administration. Four-week old ASS1$^{fold/fold}$ received a single retro-orbital injection of AAV8.LSP.IVS2.hASS1co.bGH vector at the dose of 3×10$^{11}$ or 1×10$^{11}$ GC/mouse. ASS1$^{fold/fold}$ (Fold) mice were provided as controls.

Figure 9A:
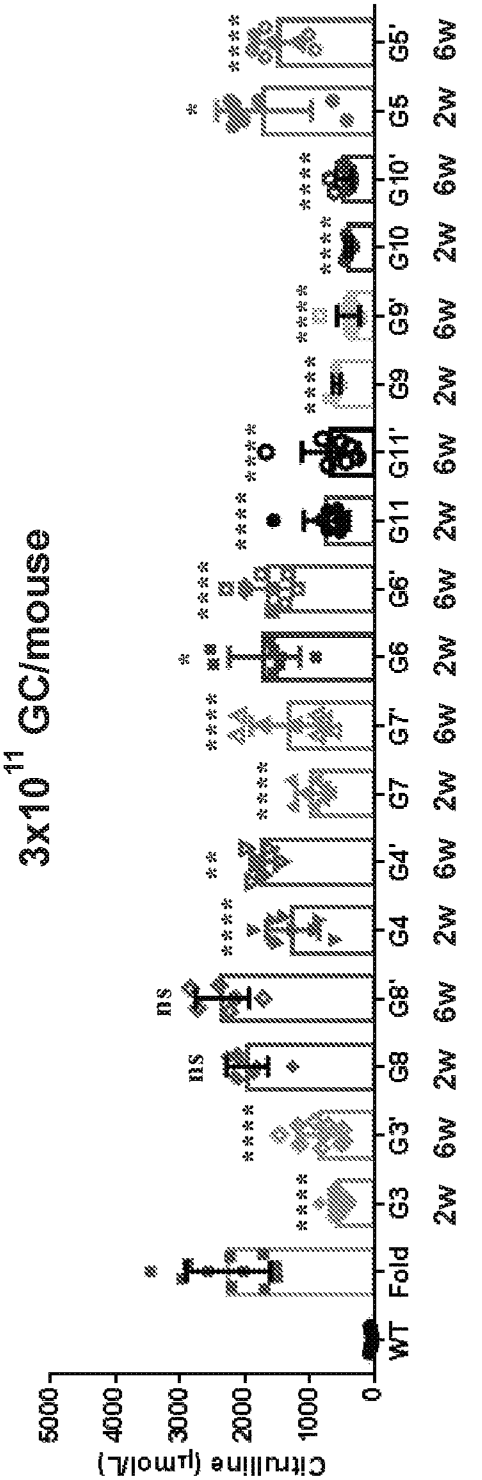
Figure 9B:
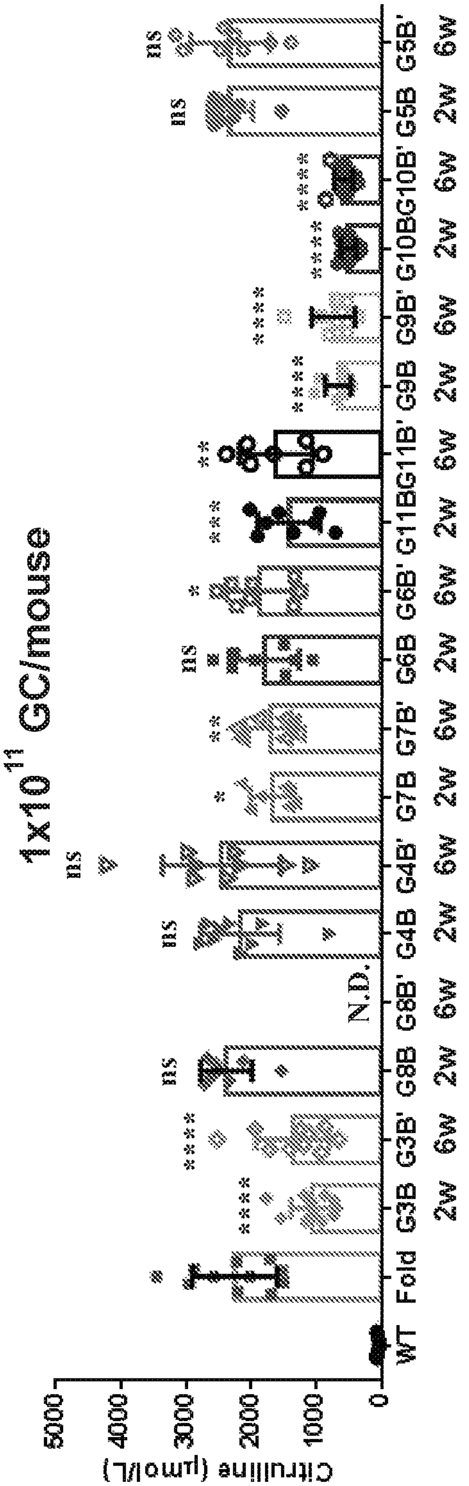

FIGS. 9A to 9B provide graphs showing citrulline levels in ASS1$^{fold/fold}$ mice at 2 weeks and 6 weeks post AAV8 vector administration. Four-week old ASS1$^{fold/fold}$ received a single retro-orbital injection of the indicated vector at the dose of 3×10$^{11}$ GC/mouse (FIG. 9A) or 1×10$^{11}$ GC/mouse (FIG. 9B). Code for each vector is listed in Table 1. Untreated ASS1$^{fold/fold}$ (Fold) and wild-type (WT) mice were provided as controls. Significant differences compared to untreated fold mice were calculated using one-way ANOVA Dunnett's multiple comparisons test. *P<0.05, P<0.01, *P<0.001, ****P<0.0001.

Figure 10:
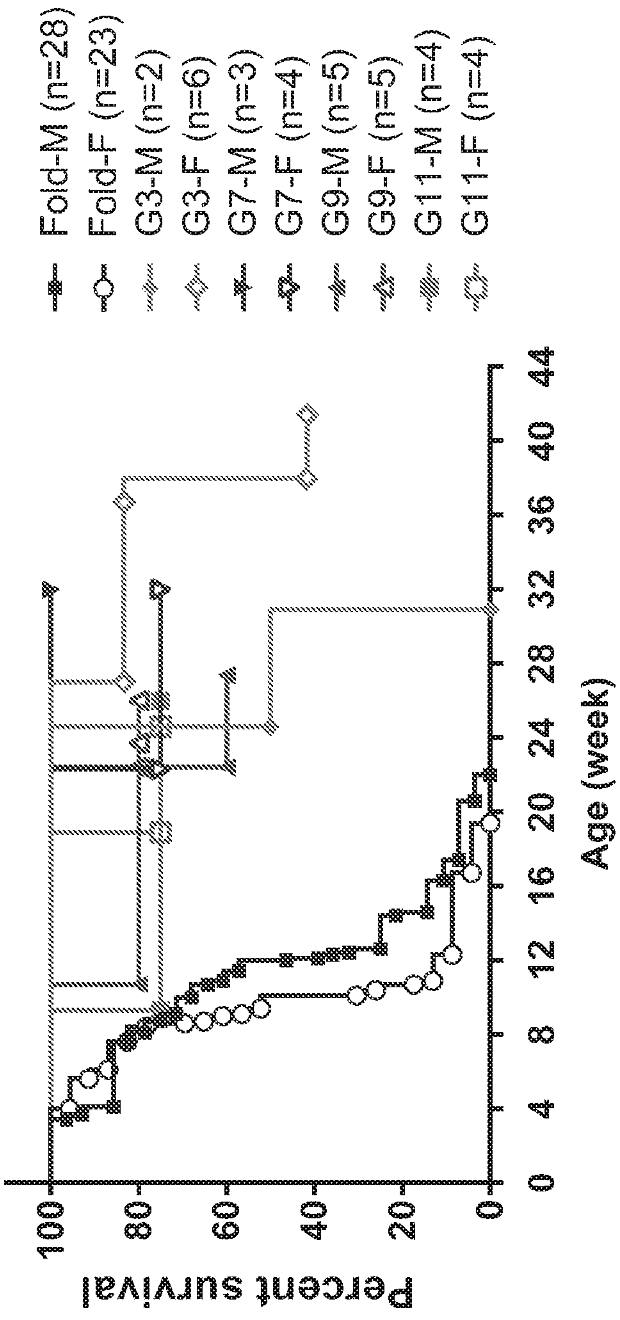

FIG. 10 is a graph showing percent survival in ASS1$^{fold/fold}$ mice. Four-week old ASS1$^{fold/fold}$ received a single retro-orbital injection of the indicated vector at the dose of 1×10$^{11}$ GC/mouse. Code for each vector is listed in Table 1. Untreated ASS1$^{fold/fold}$ (Fold) and wild-type (WT) mice were provided as controls.

FIG. 11A is a graph showing body weight in male ASS1$^{fold/fold}$ mice. Four-week old ASS1$^{fold/fold}$ received a single retro-orbital injection of the indicated vector at the dose of 1×10$^{11}$ GC/mouse. Code for each vector is listed in Table 1. Untreated ASS1$^{fold/fold}$ (Fold) and wild-type (WT) mice were provided as controls. Liver-directed gene therapy improves the body weight of ASS1$^{fold/fold}$.

FIG. 11B is a graph showing body weight in female ASS1$^{fold/fold}$ mice. Four-week old ASS1$^{fold/fold}$ received a single retro-orbital injection of the indicated vector at the dose of 1×10$^{11}$ GC/mouse. Code for each vector is listed in Table 1. Untreated ASS1$^{fold/fold}$ (Fold) and wild-type (WT) mice were provided as controls. Liver-directed gene therapy improves the body weight of ASS1$^{fold/fold}$.

FIGS. 12A and 12B are graphs showing a reduction in plasma citrulline levels by AAV. Four-week old ASS1 fold/fold (both males and females) received a single retro-orbital injection of AAV8-hASS1 vectors at the dose of 1×10$^{11}$ GC/mouse. Code for each vector is listed in Table 1. Plasma citrulline levels at 2 weeks (A) and 6 weeks (B) post vector administration. P<0.01; **P<0.0001, one-way ANOVA, Kruskal-Wallis test, compared to untreated fold mice.

Figure 13:
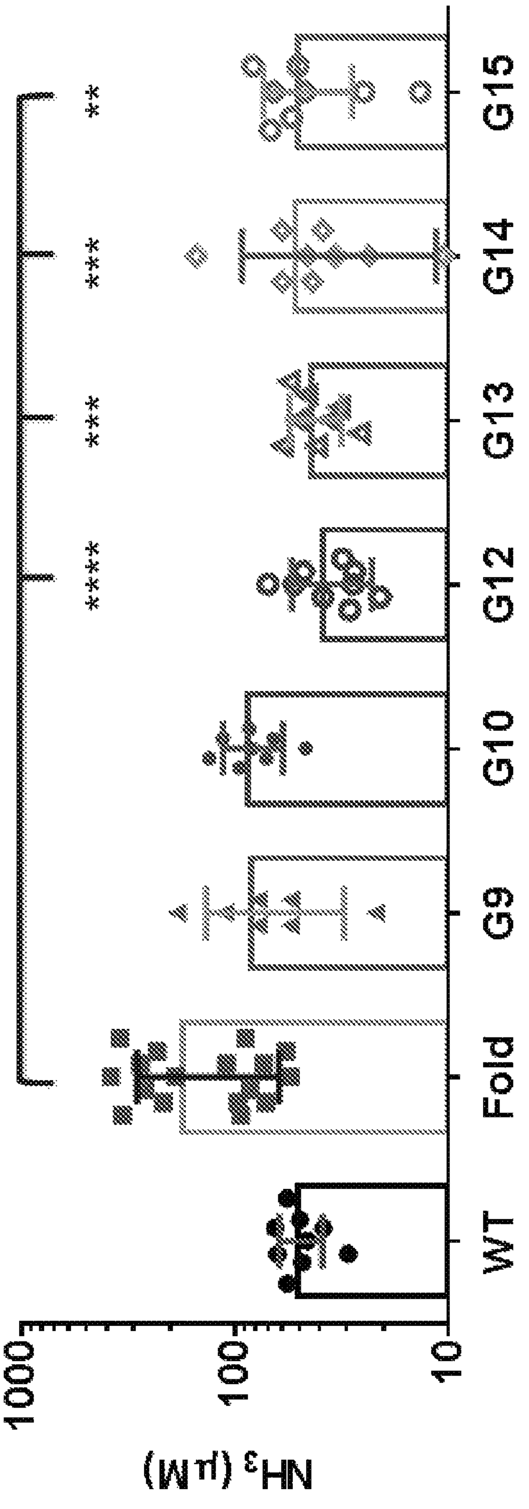

FIG. 13 is a graph showing a reduction in plasma citrulline levels by AAV. Four-week-old fold mice received a single retro orbital injection of AAV8-hASS1 vectors at the dose of 1.0×1011 GC. Plasma NH3 levels at 6 weeks post vector injection are shown here. P<0.01; *P<0.001; ****P<0.0001, one-way ANOVA, Kruskal-Wallis test, compared to untreated fold mice.

4. DETAILED DESCRIPTION

The embodiments described in the application relate to the use of a replication deficient adeno-associated virus (AAV) to deliver a human Argininosuccinate Synthase 1 (hASS1) gene to liver cells of patients (human subjects) diagnosed with type 1 citrullenemia (CTLN1). The recombinant AAV vector (rAAV) used for delivering the hASS gene ("rAAV.hASS1") should have a tropism for the liver (e.g., an rAAV bearing an AAV8 capsid), and the hASS1 transgene should be controlled by liver-specific expression control elements. In one embodiment, the expression control elements include one or more of the following: an enhancer; a promoter; an intron; a WPRE; and a polyA signal. Such elements are further described herein.

As used herein, "AAV8 capsid" refers to the AAV8 capsid having the amino acid sequence of GenBank, accession: YP_077180.1, SEQ ID NO: 19, and/or an AAV8 capsid encoded by the nucleic acid sequence of GenBank: AF513852.1, nt 2121-4337, SEQ ID NO: 36, which sequences are incorporated by reference herein. Some variation from this encoded sequence is permitted, which may include sequences having about 99% identity to the referenced amino acid sequence in YP_077180.1 and WO 2003/052051 (which is incorporated herein by reference) (i.e., less than about 1% variation from the referenced sequence). Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2015/0315612.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, the term "operably linked" refers to both expression control sequences that are contiguous with the gene of interest and expression control sequences that act in trans or at a distance to control the gene of interest.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

4.1 Gene Therapy Vectors

In one aspect, a recombinant adeno-associated virus (rAAV) vector carrying the human ASS1 gene is provided for use in gene therapy. The rAAV.hASS1 vector should have a tropism for the liver (e.g., a rAAV bearing an AAV8 capsid) and the hASS1 transgene should be controlled by liver-specific expression control elements. In another embodiment, the rAAV.hASS1 vector has a tropism for kidney. The vector is formulated in a buffer/carrier suitable for infusion in human subjects. The buffer/carrier should include a component that prevents the rAAV from sticking to the infusion tubing but does not interfere with the rAAV binding activity in vivo.

4.1.1. The rAAV.hASS Vector 4.1.1.1. The hASS1 Sequence

Citrullinemia type I (CTLN1) (also called "classic citrullinemia") results from deficiency of the enzyme argininosuccinate synthase 1 (ASS1), the third step in the urea cycle, in which citrulline is condensed with aspartate to form arginosuccinic acid.

Type I citrullinemia shows kinetically abnormal ASS1 in the liver, kidney, and cultured fibroblasts. In quantitative-type citrullinemia, low ASS1 is found in the liver but not in kidney or cultured skin fibroblasts. Residual enzyme in the liver has normal kinetic properties (Saheki et al., 1981). In a study of mRNA coding for ASS1, Kobayashi et al. (Am J. Hum. Genet., 38:667-80, 1986, which is incorporated herein by reference) found that patients with the quantitative type of citrullinemia had, as demonstrated in previous studies, about 10% of the control value of the enzyme in the liver but a normal level of mRNA. They concluded that in quantitative-type citrullinemia, the decrease in the enzyme protein is due either to increased degradation of the enzyme or to decreased or inhibited translation in the liver.

Although certain pathogenic variants are identified with some phenotypes, the phenotype cannot be predicted in all instances. Severe, classic citrullinemia type I typically results from 22 defined pathogenic variants (Engel et al, Human Mutation, 2009 March; 30(3):300-7, which is incorporated herein by reference). The pathogenic variant in exon 15, p.Gly390Arg, remains the most prevalent associated with the classic phenotype. Mild (i.e., late-onset) citrullinemia type I is associated with 12 pathogenic variants.

One goal of therapies described herein would provide functional ASS1 enzyme resulting in citrulline, glutamine, and/or ammonia levels less than 100 μmol/L. In another embodiment, any reduction in citrulline, glutamine, and/or ammonia levels is desirable. Other suitable clinical outcomes may include reduction in the use of scavenger, less restrictive diet or no need for liver transplant.

In one embodiment, the "subject" or "patient" is a mammalian subject having CTLN1 as described above. It is intended that a patient having CTLN1 of any severity is the intended subject. In addition, it is intended that a patient having any mutation in their native ASS1 gene is the intended subject.

In one embodiment, the hASS1 gene encodes the hASS1 protein shown in SEQ ID NO: 1. Thus, in one embodiment, the hASS1 transgene can include, but is not limited to, the sequence provided by SEQ ID NO:2 or SEQ ID NO: 3 which are provided in the attached Sequence Listing, which is incorporated by reference herein. SEQ ID NO: 3 provides the cDNA for native human ASS1. SEQ ID NO: 2 provides an engineered cDNA for human ASS1, which has been codon optimized for expression in humans (sometimes referred to herein as hASS1co). It is to be understood that reference to hASS1 herein may, in some embodiments, refer to the hASS1 native or codon optimized sequence. Alternatively or additionally, web-based or commercially available computer programs, as well as service based companies may be used to back translate the amino acid sequences to nucleic acid coding sequences, including both RNA and/or cDNA. See, e.g., backtranseq by EMBOSS, /www.ebi.ac.uk/Tools/st/; Gene Infinity (www.geneinfinity.org/sms-/sms_backtranslation.html); ExPasy (www.expasy.org/tools/). It is intended that all nucleic acids encoding the described hASS1 polypeptide sequences are encompassed, including nucleic acid sequences which have been optimized for expression in the desired target subject (e.g., by codon optimization).

In one embodiment, the nucleic acid sequence encoding hASS1 shares at least 95% identity with the native hASS1 coding sequence of SEQ ID NO: 3. In another embodiment, the nucleic acid sequence encoding hASS1 shares at least 90, 85, 80, 75, 70, or 65% identity with the native hASS1 coding sequence of SEQ ID NO: 3. In one embodiment, the nucleic acid sequence encoding hASS1 shares about 84% identity with the native hASS1 coding sequence of SEQ ID NO: 3. In one embodiment, the nucleic acid sequence encoding hASS1 is SEQ ID NO: 2.

In one embodiment, the hASS1 coding sequence is codon optimized for expression in the desirable subject species, e.g., humans. Codon-optimized coding regions can be designed by various different methods. This optimization may be performed using methods which are available online (e.g., GeneArt), published methods, or a company which provides codon optimizing services, e.g., as DNA2.0 (Menlo Park, Calif.). One codon optimizing approach is described, e.g., in International Patent Publication No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered (e.g., one or more of the individual immunoglobulin domains). By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Thermo Fisher Scientific Inc. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

4.1.1.2. The rAAV Vector

Because ASS1 is natively expressed in the liver, it is desirable to use an AAV which shows tropism for liver. In one embodiment, the AAV supplying the capsid is AAV8. In another embodiment, the AAV supplying the capsid is AAVrh. 10. In yet another embodiment, the AAV supplying the capsid is a Clade E AAV. Such AAV include rh.2; rh.10; rh. 25; bb.1, bb.2, pi.1, pi.2, pi.3, rh.38, rh.40, rh.43, rh.49, rh.50, rh.51, rh.52, rh.53, rh.57, rh.58, rh.61, rh.64, hu.6, hu.17, hu.37, hu.39, hu.40, hu.41, hu.42, hu.66, and hu.67. This clade further includes modified rh. 2; modified rh. 58; and modified rh.64. See, WO 2005/033321, which is incorporated herein by reference. However, any of a number of rAAV vectors with liver tropism can be used. In another embodiment, the rAAV vector has a tropism for kidney.

In a specific embodiment described in the Examples, infra, the gene therapy vector is an AAV8 vector expressing an hASS1 transgene under control of a thyroxine binding globulin (TBG) promoter referred to as AAV8.TBG.PI.hASS1co.WPRE.bGH. In another embodiment, the WPRE is removed. In another embodiment, the gene therapy vector is an AAV8 vector expressing an hASS1 transgene under control of a A1AT promoter, with an ApoE1 enhancer referred to as AAV8.ApoE.A1AT(full).IVS2.hASS1co.bGH. The external AAV vector component is a serotype 8, T=1 icosahedral capsid consisting of 60 copies of three AAV viral proteins, VP1, VP2, and VP3, at a ratio of 1:1:10. The capsid contains a single-stranded DNA rAAV vector genome.

In one embodiment, the rAAV.hASS1 genome contains an hASS1 transgene flanked by two AAV inverted terminal repeats (ITRs). In one embodiment, the hASS1 transgene includes one or more of an enhancer, promoter, an intron, a Woodchuck Hepatitis Virus (WHP) Posttranscriptional Regulatory Element (WPRE), an hASS1 coding sequence, and polyadenylation (polyA) signal. These control sequences are "operably linked" to the hASS1 gene sequences. The expression cassette containing these sequences may be engineered onto a plasmid which is used for production of a viral vector.

The ITRs are the genetic elements responsible for the replication and packaging of the genome during vector production and are the only viral cis elements required to generate rAAV. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hASS1 coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used. In one embodiment, the 5' ITR is that shown in SEQ ID NO: 16. In one embodiment, the 3' ITR is that shown in SEQ ID NO: 17.

Exemplary production plasmids to generate rAAVs are shown in SEQ ID NOs: 22 to 35. In one embodiment, provided herein is the plasmid of SEQ ID NO: 22. In another embodiment, provided herein is the plasmid of SEQ ID NO: 23. In another embodiment, provided herein is the plasmid of SEQ ID NO: 24. In another embodiment, provided herein is the plasmid of SEQ ID NO: 25. In another embodiment, provided herein is the plasmid of SEQ ID NO: 26. In another embodiment, provided herein is the plasmid of SEQ ID NO: 27. In another embodiment, provided herein is the plasmid of SEQ ID NO: 28. In another embodiment, provided herein is the plasmid of SEQ ID NO: 29. In another embodiment, provided herein is the plasmid of SEQ ID NO: 30. In another embodiment, provided herein is the plasmid of SEQ ID NO: 31. In another embodiment, provided herein is the plasmid of SEQ ID NO: 32. In another embodiment, provided herein is the plasmid of SEQ ID NO: 33. In another embodiment, provided herein is the plasmid of SEQ ID NO: 34. In another embodiment, provided herein is the plasmid of SEQ ID NO: 35.

Expression of the hASS1 coding sequence is driven from a liver-specific promoter. An illustrative plasmid and vector described herein uses the thyroxine binding globulin (TBG) promoter (SEQ ID NO: 9), or a modified version thereof. One modified version of the TBG promoter is a shortened version, termed TBG-S 1. A modified thyroxine binding globulin (TBG-S 1) promoter sequence is shown in SEQ ID NO: 8. Alternatively, other liver-specific promoters may be used such as the transthyretin promoter (TTR) (SEQ ID NO: 11). Another suitable promoter is the alpha 1 anti-trypsin (A1AT), or a modified version thereof (which sequence is shown in SEQ ID NO: 10). In one embodiment, the promoter is an A1AT promoter combined with an ApoE enhancer, sometimes referred to as ApoE.A1AT (full). In one embodiment, the sequence is shown in SEQ ID NO: 20. Another suitable promoter is the Liver specific promoter LSP (TH-binding globulin promoter/alpha1-microglobulin/bikunin enhancer) (SEQ ID NO: 21). Other suitable promoters include human albumin (Miyatake et al., J. Virol., 71:5124 32 (1997)), humAlb; and hepatitis B virus core promoter, (Sandig et al., Gene Ther., 3:1002-9 (1996). See, e.g., The Liver Specific Gene Promoter Database, Cold Spring Harbor, rulai.schl.edu/LSPD, which is incorporated by reference. Although less desired, other promoters, such as viral promoters, constitutive promoters, regulatable promoters [see, e.g., WO 2011/126808 and WO 2013/04943], or a promoter responsive to physiologic cues may be used may be utilized in the vectors described herein.

In one embodiment, the expression control sequences include one or more enhancer. In one embodiment, the En34 enhancer is included (34 bp core enhancer from the human apolipoprotein hepatic control region), which is shown in SEQ ID NO: 4. In another embodiment, the EnTTR (100 bp enhancer sequence from transthyretin) is included. Such sequence is shown in SEQ ID NO: 5. See, Wu et al, Molecular Therapy, 16(2):280-289, February 2008, which is incorporated herein by reference. In yet another embodiment, the $\alpha$1-microglogulin/bikunin precursor enhancer is included. In yet another embodiment, the ABPS (shortened version of the 100 bp distal enhancer from the $\alpha$1-microglogulin/bikunin precursor [ABP] to 42 bp) enhancer is included. Such sequence is shown in SEQ ID NO: 6. In yet another embodiment, the ApoE enhancer is included. Such sequence is shown in SEQ ID NO: 7. In another embodiment, more than one enhancer is present. Such combination may include more than one copy of any of the enhancers described herein, and/or more than one type of enhancer.

In addition to a promoter, an expression cassette and/or a vector may contain other appropriate transcription initiation, termination, enhancer sequences, and efficient RNA processing signals. Such sequences include splicing and polyadenylation (polyA) signals; regulatory elements that enhance expression (i.e., WPRE (SEQ ID NO: 15); sequences that stabilize cytoplasmic mRNA; sequences that enhance translation efficiency (i.e., Kozak consensus sequence); sequences that enhance protein stability; and when desired, sequences that enhance secretion of the encoded product. In one embodiment, a polyadenylation (polyA) signal is included to mediate termination of hASS1 mRNA transcripts. Examples of other suitable polyA sequences include, e.g., bovine growth hormone (SEQ ID NO: 12), SV40, rabbit beta globin, and TK polyA, amongst others.

In one embodiment, the regulatory sequences are selected such that the total rAAV vector genome is about 2.0 to about 5.5 kilobases in size. In one embodiment, the regulatory sequences are selected such that the total rAAV vector genome is about 2.1, 2.3, 2.8, 3.1, 3.2, 3.3 or 4.0 kb in size. In one embodiment, it is desirable that the rAAV vector genome approximate the size of the native AAV genome. Thus, in one embodiment, the regulatory sequences are selected such that the total rAAV vector genome is about 4.7 kb in size. In another embodiment, the total rAAV vector genome is less about 5.2 kb in size. The size of the vector genome may be manipulated based on the size of the regulatory sequences including the promoter, enhancer, intron, poly A, etc. See, Wu et al, Mol Ther, January 2010 18(1):80-6, which is incorporated herein by reference.

Thus, in one embodiment, an intron is included in the vector. Suitable introns include the human beta globin IVS2 (SEQ ID NO: 13). See, Kelly et al, Nucleic Acids Research, 43(9):4721-32 (2015), which is incorporated herein by reference. Another suitable promoter includes the Promega chimeric intron (SEQ ID NO: 14). See, Almond, B. and Schenborn, E. T. A Comparison of pCI-neo Vector and pcDNA4/HisMax Vector. [Internet] 2000, which is incorporated herein by reference. Available from: www.promega.com/resources/pubhub/enotes/a-comparison-of-pcineo-vector-and-pcdna4hismax-vector/). Another suitable intron includes the hFIX intron (SEQ ID NO: 18). Various introns suitable herein are known in the art and include, without limitation, those found at bpg.utoledo.edu/~afedorov/lab/eid.html, which is incorporated herein by reference. See also, Shepelev V., Fedorov A. Advances in the Exon-Intron Database. Briefings in Bioinformatics 2006, 7: 178-185, which is incorporated herein by reference.

In one embodiment, the rAAV vector genome comprises a sequence selected from nt 1 to nt 3216 of SEQ ID NO: 22, nt 1 to nt 2331 of SEQ ID NO: 23, nt 1 to nt 3261 of SEQ ID NO: 24, nt 1 to nt 3325 of SEQ ID NO: 25, nt 1 to nt 2777 of SEQ ID NO: 26, nt 1 to nt 2777 of SEQ ID NO: 27, nt 1 to nt 3216 of SEQ ID NO: 28, nt 1 to nt 3066 of SEQ ID NO: 29, nt 1 to nt 2083 of SEQ ID NO: 30, nt 1 to nt 2121 of SEQ ID NO:31, nt 1 to nt 3221 of SEQ ID NO: 32, nt 1 to nt 4040 of SEQ ID NO: 33, nt 1 to nt 2798 of SEQ ID NO: 34, or nt 1 to nt 3066 of SEQ ID NO: 35.

4.1.2. Compositions

In one embodiment, the rAAV.hASS1 virus is provided in a pharmaceutical composition which comprises an aqueous carrier, excipient, diluent or buffer. In one embodiment, the buffer is PBS. In a specific embodiment, the rAAV.hASS1 formulation is a suspension containing an effective amount of rAAV.hASS1 vector suspended in an aqueous solution containing 0.001% Pluronic F-68 in TMN200 (200 mM sodium chloride, 1 mM magnesium chloride, 20 mM Tris, pH 8.0). However, various suitable solutions are known including those which include one or more of: buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration.

For example, a suspension as provided herein may contain both NaCl and KCl. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene (poly (propylene oxide)) flanked by two hydrophilic chains of polyoxyethylene (poly(ethylene oxide)), SOLUTOL® HS 15 (Macrogol-15 Hydroxystearate), LABRASOL® (Polyoxy capryllic glyceride), polyoxy 10 oleyl ether, TWEEN®

(polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In another embodiment, the vector is suspended in an aqueous solution containing 180 mM sodium chloride, 10 mM sodium phosphate, 0.001% Poloxamer 188, pH 7.3.

In one embodiment, the formulation is suitable for use in human subjects and is administered intravenously. In one embodiment, the formulation is delivered via a peripheral vein by bolus injection. In one embodiment, the formulation is delivered via a peripheral vein by infusion over about 10 minutes (+5 minutes). In one embodiment, the formulation is delivered via a peripheral vein by infusion over about 20 minutes (+5 minutes). In one embodiment, the formulation is delivered via a peripheral vein by infusion over about 30 minutes (+5 minutes). In one embodiment, the formulation is delivered via a peripheral vein by infusion over about 60 minutes (+5 minutes). In one embodiment, the formulation is delivered via a peripheral vein by infusion over about 90 minutes (+10 minutes). However, this time may be adjusted as needed or desired. Any suitable method or route can be used to administer an AAV-containing composition as described herein, and optionally, to co-administer other active drugs or therapies in conjunction with the AAV-mediated delivery of hASS1 described herein. Routes of administration include, for example, systemic, oral, inhalation, intranasal, intratracheal, intraarterial, intraocular, intravenous, intramuscular, subcutaneous, intradermal, and other parental routes of administration.

In one embodiment, the formulation may contain, e.g., about $1.0\times10^{11}$ genome copies per kilogram of patient body weight (GC/kg) to about $1\times10^{14}$ GC/kg, about $5\times10^{11}$ genome copies per kilogram of patient body weight (GC/kg) to about $3\times10^{13}$ GC/kg, or about $1\times10^{12}$ to about $1\times10^{14}$ GC/kg, as measured by oqPCR or digital droplet PCR (ddPCR) as described in, e.g., M. Lock et al, Hum Gene Ther Methods. 2014 April; 25(2):115-25. doi: 10.1089/hgtb.2013.131. Epub 2014 Feb. 14, which is incorporated herein by reference. In one embodiment, the rAAV.hASS formulation is a suspension containing at least $1\times10^{13}$ genome copies (GC)/mL, or greater, as measured by oqPCR or digital droplet PCR (ddPCR) as described in, e.g., M. Lock et al, supra.

In order to ensure that empty capsids are removed from the dose of AAV.hASS1 that is administered to patients, empty capsids are separated from vector particles during the vector purification process, e.g., using the method discussed herein. In one embodiment, the vector particles containing packaged genomes are purified from empty capsids using the process described in U.S. Patent Appln No. 62/322,098, filed on Apr. 13, 2016, and entitled "Scalable Purification Method for AAV8", which is incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates. Similar purification methods can be used for vectors having other capsids.

While any conventional manufacturing process can be utilized, the process described herein (and in U.S. Patent Appln No. 62/322,098) yields vector preparations wherein between 50 and 70% of the particles have a vector genome, i.e., 50 to 70% full particles. Thus for an exemplary dose of $1.6\times10^{12}$ GC/kg, and the total particle dose will be between $2.3\times10^{12}$ and $3\times10^{12}$ particles. In another embodiment, the proposed dose is one half log higher, or $5\times10^{12}$ GC/kg, and the total particle dose will be between $7.6\times10^{12}$ and $1.1\times10^{13}$ particles. In one embodiment, the formulation is be characterized by an rAAV stock having a ratio of "empty" to "full" of 1 or less, preferably less than 0.75, more preferably, 0.5, preferably less than 0.3.

A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation.

Generally, methods for assaying for empty capsids and AAV vector particles with packaged genomes have been known in the art. See, e.g., Grimm et al., *Gene Therapy* (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the BI anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 ng/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2): 115-25. doi: 101089/hgtb.2013.131. Epub 2014 Feb. 14, 4.2 Patient Population As discussed above, a subject having CTLN1 of any severity is the intended recipient of the compositions and methods described herein.

Subjects may be permitted to continue their standard of care treatment(s) (e.g., protein restricted diet, and/or medications (including nitrogen scavenger therapy and carnitine)) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy.

Desirable endpoints of the gene therapy regimen are an increase in ASS activity resulting in citrulline levels below about 100 μmol/L and/or ammonia levels below about 100 μmol/L. In another embodiment, any reduction in citrulline, glutamine, and/or ammonia levels is desirable. Other suitable clinical outcomes may include reduction in the use of scavenger, less restrictive diet or no need for liver transplant. In one embodiment, patients achieve reduced circulating ASS1 levels after treatment with rAAV.hASS1, alone and/or combined with the use of adjunctive treatments.

4.3. Dosing & Route of Administration

In one embodiment, the rAAV.hASS1 vector is delivered as a single dose per patient. In one embodiment, the subject is delivered the minimal effective dose (MED) (as determined by preclinical study described in the Examples herein). As used herein, MED refers to the rAAV.hASS1 dose required to achieve ASS1 activity resulting in citrulline levels below about 100 μmol/L and/or ammonia levels below about 100 μmol/L.

As is conventional, the vector titer is determined on the basis of the DNA content of the vector preparation. In one embodiment, quantitative PCR or optimized quantitative PCR as described in the Examples is used to determine the DNA content of the rAAV.hASS1 vector preparations. In one embodiment, digital droplet PCR as described in the Examples is used to determine the DNA content of the rAAV.hASS1 vector preparations. In one embodiment, the dosage is about $1\times10^{11}$ genome copies (GC)/kg body weight to about $1\times10^{13}$ GC/kg, inclusive of endpoints. In one embodiment, the dosage is $5\times10^{11}$ GC/kg. In another embodiment, the dosage is $5\times10^{12}$ GC/kg. In specific embodiments, the dose of rAAV.hASS1 administered to a patient is at least $5\times10^{11}$ GC/kg, $1\times10^{12}$ GC/kg, $1.5\times10^{12}$ GC/kg, $2.0\times10^{12}$ GC/kg, $2.5\times10^{12}$ GC/kg, $3.0\times10^{12}$ GC/kg, $3.5\times10^{12}$ GC/kg, $4.0\times10^{12}$ GC/kg, $4.5\times10^{12}$ GC/kg, $5.0\times10^{12}$ GC/kg, $5.5\times10^{12}$ GC/kg, $6.0\times10^{12}$ GC/kg, $6.5\times10^{12}$ GC/kg, $7.0\times10^{12}$ GC/kg, or $7.5\times10^{12}$ GC/kg. Also, the replication-defective virus compositions can be formulated in dosage units to contain an amount of replication-defective virus that is in the range of about $1.0\times10^{9}$ GC to about $1.0\times10^{15}$ GC. As used herein, the term "dosage" can refer to the total dosage delivered to the subject in the course of treatment, or the amount delivered in a single (of multiple) administration.

In some embodiments, rAAV.hASS1 is administered in combination with one or more therapies for the treatment of CTLN1, such as a low protein diet or administration nitrogen scavenger therapy or dialysis.

4.4. Measuring Clinical Objectives

Measurements of efficacy of treatment can be measured by transgene expression and activity as determined by ammonia or citrulline levels and/or ASS1 activity. Further assessment of efficacy can be determined by clinical assessment of dietary citrulline tolerance.

As used herein, the rAAV.hASS1 vector herein "functionally replaces" or "functionally supplements" the patients defective ASS1 with active ASS1 when the patient expresses a sufficient level of ASS1 to achieve ASS1 activity resulting in citrulline and/or ammonia levels less than about 100 μmol/L. In another embodiment, the rAAV.hASS1 vector functionally replaces or functionally supplements the patient's defective ASS1 when partial rescue is provided. This allows for treatment with a combination of scavengers and dietary control. In one embodiment, the treatment provides sufficient rescue such that liver transplantation is not required. In another embodiment, a reduction in the rate of complications such as viral diseases (e.g., flu) is desired.

5. EXAMPLES

The following examples are illustrative only and are not intended to limit the present invention.

Example 1: AAV Vectors Containing hASS1

An exemplary gene therapy vector AAV8.TBG.PI.hASS1co.WPRE.bGH was constructed by an AAV8 vector bearing a codon-optimized human ASS1 cDNA (hASS1co) under the control of TBG, a hybrid promoter based on the human thyroid hormone-binding globulin promoter and microglobin/bikunin enhancer. The ASS1 expression cassette was flanked by AAV2 derived inverted terminal repeats (ITRs) and the expression was driven by a hybrid of the TBG enhancer/promoter and the Woodchuck Hepatitis Virus (WHP) posttranscriptional regulatory element (WPRE) as an enhancer. The transgene also included the Promega SV40 misc intron (PI) and a bovine growth hormone polyadenylation signal (bGH).

Another Exemplary Gene Therapy Vector

Figure 1:
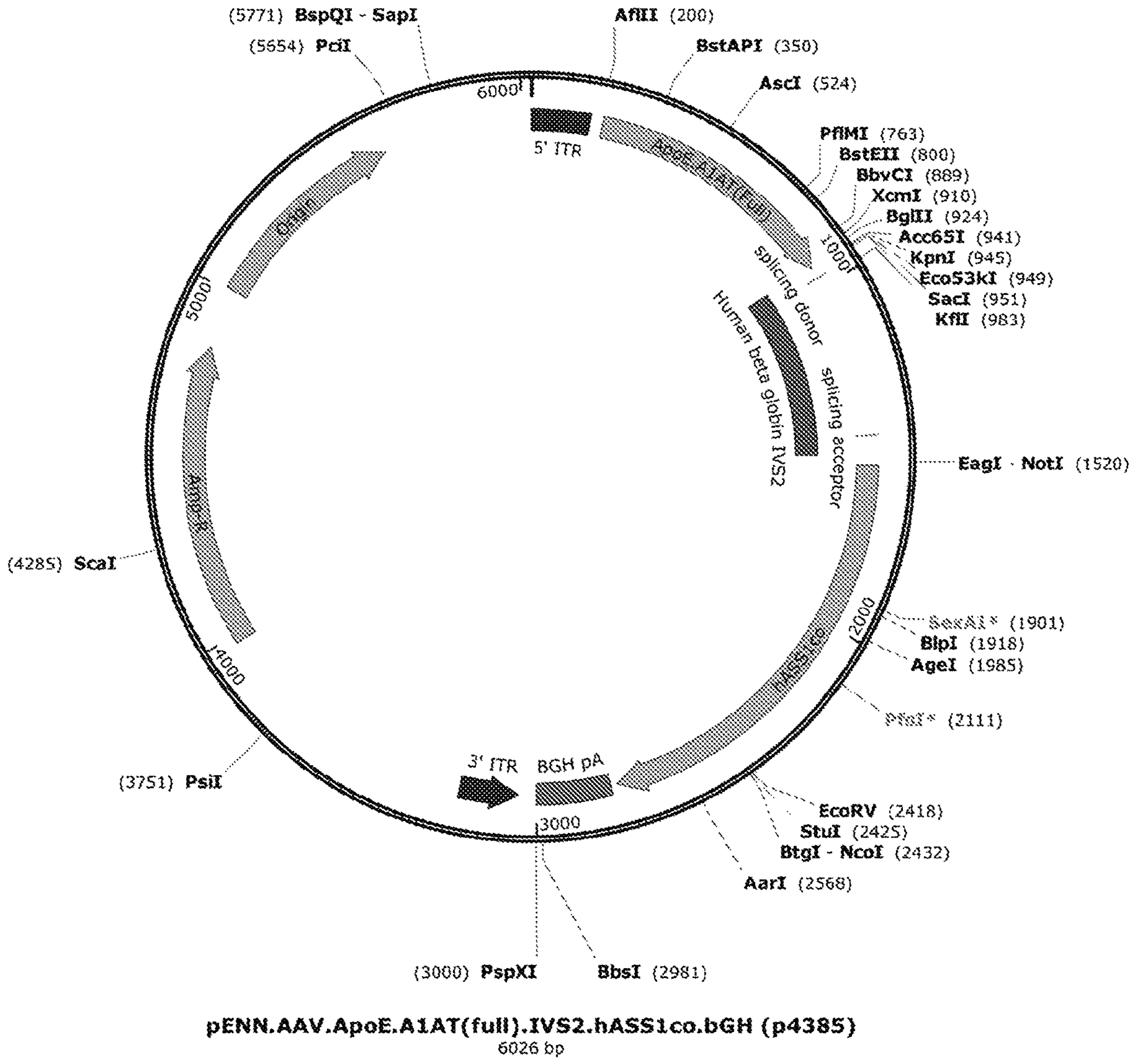
FIG. 1 is a schematic representation of AAV.hASS1co cis plasmid.

AAV8.ApoE.A1AT(full).IVS2.hASS1 co.bGH was constructed by an AAV8 vector bearing a codon-optimized human ASS1 cDNA (hASS1 co) under the control of A1AT promoter and a ApoE enhancer (FIG. 1). The ASS1 expression cassette was flanked by AAV2 derived inverted terminal repeats (ITRs) and the expression was driven by the ApoE.A1AT enhancer/promoter. The transgene also included the human beta globin IVS2 as an intron and a bovine growth hormone polyadenylation signal (bGH).

The vector AAV8.TBG.PI.hASS1co.bGH was constructed as described above without WPRE as an enhancer.

The AAV8.LSP.IVS2.hASS1co.bGH vector encodes a codon-optimized human ASS1 cDNA (hASS co) under the control of a liver-specific promoter (LSP), with intervening sequence 2 (IVS2) and a bovine growth hormone polyadenylation signal (bGH).

The vector was prepared using conventional triple transfection techniques in 293 cells as described e.g., by Mizukami, Hiroaki, et al. *A Protocol for AAV vector production and purification*. Diss. Di-vision of Genetic Therapeutics, Center for Molecular Medicine, 1998, which is incorporated herein by reference. All vectors were produced by the Vector Core at the University of Pennsylvania as previously described [Lock, M., et al, Hum Gene Ther, 21: 1259-1271 (2010)].

Example 2: Natural History Study

All animal procedures were performed in accordance with protocols approved by the Institutional Animal Care and Use Committee (IACUC) of the University of Pennsylvania.

Citrullinemia is an autosomal recessive disease caused by mutations in argininosuccinate synthase (ASS1) enzyme that catalyzes the synthesis of argininosuccinate from citrulline and aspartate, results in citrullinemia and buildup of ammonia. $ASS1^{fold/fold}$ mouse express deficient argininosuccinate synthase 1 (ASS1) [Harris B S, et al., Follicular dystrophy: a new skin and hair mutation on mouse Chromosome 2. MGI Direct Data Submission. 2007]. FOLD allele mice have a T3891 substitution in exon 15 leading to an unstable protein structure with normal ASS1 mRNA and protein levels. Homozygotes survive up to 3 weeks or longer, have 5-10% enzyme activity and display clinical and biochemical parameters similar to CTLN1. At 1 week of age fold homozygotes lack hair such that they can be distinguished from their control littermates, and at 2 weeks of age fold homozygotes have wrinkled skin, a sparse coat does grow in. By P14 mice show a 10- to 40-fold increase in the levels of citrulline, and a 1.5- to threefold increase in the plasma levels of many amino acids, including glutamine, cystine, methionine, and lysine and arginine, glutamic acid, leucine, and omithine levels are decreased.

$ASS1^{fold/fold}$ mice thus served as a mouse model for Citrullinemia. Survival curve was generated based on the observation of 28 male and 23 female $ASS1^{fold/fold}$ mice (FIG. 2A). The result demonstrated that functionally deficient ASS1 reduced the lifespan of $ASS1^{fold/fold}$ mice significantly.

As a second parameter for normal development and growth, the body weights of $ASS1^{fold/fold}$ mice and healthy littermates after weaning were closely monitored and recorded. The results showed that female $ASS1^{fold/fold}$ mice weight remained relatively constant and the body weights of male $ASS1^{fold/fold}$ mice reached plateau at about 8 weeks old while both genders of wild-type littermates exhibited a steady growth over the observation period (FIG. 2B). It further demonstrated that functionally deficient ASS1 compromised the development and growth of the mice.

Additional testing was done on the untreated $ASS1^{fold/fold}$ mice and healthy littermates, including measurement of plasma ammonia (FIG. 2C), plasma citrulline (FIG. 2D). plasma arginine (FIG. 2E), urine orotic acid (FIG. 2E). Ammonia, citrulline, arginine and orotic acid levels were all elevated in untreated $ASS1^{fold/fold}$ mice as compared to healthy littermates.

Example 3: AAV8.hASS1 Vectors in the Model of Citrullenemia

To evaluate the efficacy and determine the dose-dependent effects of AAV8.hASS1co vectors, $ASS1^{fold/fold}$ mice were injected with $1\times10^{11}$ GC/mouse or $3\times10^{11}$ GC/mouse of the gene therapy vectors intravenously at birth, as shown in the Table 1 below. Wild-type and heterozygous littermates served as controls.

$3\times10^{11}$ GC/pup of AAV8.LSP.IVS2.hASS1co.bGH vector successfully increased the rate of weight gain in male $ASS1^{fold/fold}$ mice (FIG. 3A). In females, $3\times10^{11}$ GC/pup of all three tested vectors rescued the reduction in body weight upon growth (FIG. 3B). Meanwhile, mice injected intravenously at birth with $1\times10^{11}$ GC/pup of the vectors demonstrated a slight increase in weights (FIG. 3C and FIG. 3D). Mice which received an intraperitoneal injection of the AAV8.TBG.PI.hASS1 co.WPRE.bGH vector at postnatal day 14 did not exhibit any increase in body weight (FIG. 3E and FIG. 3F).

A further experiment was performed to assess the survival of citrullenemia mice treated with the AAV8.hAASco vectors. To assess citrulline accumulation in the blood, concentration of citrulline in $ASS1^{fold/fold}$ mice with intravenous injections of AAV8.TBG.PI.hASS1co.WPRE.bGH, AAV8.LSP.IVS2.hASS1co.bGH or AAV8.TBG.PI.hASS1co.bGH on postnatal day 0 at $1\times10^{11}$ or $3\times10^{11}$ GC/pup were examined (FIG. 4B and FIG. 4A, respectively). Injection of $1\times10^{11}$ GC/pup of the vectors resulted in a minor decrease in citrulline compared to the untreated $ASS1^{fold/fold}$ mice (FIG. 4B), while $3\times10^{11}$ GC/pup of the vectors successfully brought the citrulline level down (FIG. 4A).

A further study of expression and enzyme activity of ASS1 in the injected $ASS1^{fold/fold}$ mice is performed. Livers from the tested mice injected with AAV8.hASSco vectors and the healthy littermate controls are collected and lysates are prepared. The mRNA is extracted and the expression of ASS1 is evaluated via RT-PCR. The protein expression of ASS1 is determined by western blot and immunohistochemistry. Experiments are also performed to assess the ASS1 activity in the $ASS1^{fold/fold}$ mice treated with the vector as well as controls.

An additional experiment was performed, where weight (FIG. 5A), ALT (FIG. 5B), and alkaline phosphatase (FIG. 5C) were measured on $ASS1^{fold/fold}$ mice treated with $1\times10^{11}$ GC/pup of the vector AAV8.TBG.PI.hASS1co.WPRE.bGH. Wild-type and heterozygous littermates serves as controls.

Urine orotic acid levels were measured in $ASS1^{fold/fold}$ mice injected intravenously at birth with $3\times10^{11}$ GC/pup of AAV8.TBG.PI.hASS1co.WPRE.bGH (FIG. 6A), AAV8.LSP.IVS2.hASS1co.bGH (FIG. 6B), AAV8.TBG.PI.hASS1co.bGH (FIG. 6C), or with $1\times10^{11}$ GC/pup of AAV8.LSP.IVS2.hASS1co.bGH (FIG. 6D).

Example 4: Additional Vectors

Additional AAV vectors as shown in Table below were produced. $ASS1^{fold/fold}$ mice were injected on postnatal day 0 at $1\times10^{11}$ or $3\times10^{11}$ GC/pup with the noted vectors. Citrulline levels at two and six week post injection were measured (FIGS. 9A and 9B).

FIG. 10 shows a survival curve of male and female mice injected with G3, G7, G9 and G11. All vectors tested provided significant increase in survival of $ASS1^{fold/fold}$ mice. Likewise, all vectors tested provided an increase in body weight in both male (FIG. 11A) and female (FIG. 11B) mice, a decrease in citrulline levels at 2 weeks (FIG. 12A) and 6 weeks (FIG. 12B) post injection, and a decrease in ammonia levels (FIG. 13).

In conclusion, a single injection of AAV8.hASSco vectors resulted in substantial blood citrulline reduction and concomitant functional correction when administered intravenously in ASS1-deficient mice.

Example 5: Long-Term Rescue of a Hypomorphic Lethal Murine Model of Citrullinemia Type I by Liver-Directed, AAV8-Mediated Gene Therapy Citrullinemia type I (CTLN1) is an autosomal, recessive disorder of the urea cycle caused by a deficiency of argininosuccinate synthase 1 (ASS1). The clinical

TABLE 1

Summary of Vectors for liver directed therapy for treatment of citrullinemia

| Grp | Vector | Key elements in vector<br>Enhancer-Promoter | Intron | Transgene |
|---|---|---|---|---|
| G2 | AAV8.TBG.PI.hASS1co.WPRE.bGH (p3795) | ABPx2-TBG | PI | hASS1co |
| G3 | AAV8.TBG.IVS2.hASS1co.bGH (p4169) | ABPx2-TBG | IVS2 | hASS1co |
| G4 | AAV8.TBG.PI.hASS1co.bGH (p4157) | ABPx2-TBG | PI | hASS1co |
| G5 | AAV8.EnTTR.TTR.hASS1co.bGH (p4319) | EnTTR-TTR | — | hASS1co |
| G6 | AAV8.En34.A1AT.hASS1co.bGH (p4320) | En34-A1AT | — | hASS1co |
| G7 | AAV8.TBG.PI.hASS1-native.bGH (p4339) | ABPx2-TBG | PI | hASS1-native |
| G8 | AAV8.TBG.hFIXintron.hASS1co.bGH (p4382) | ABPx2-TBG | hFIX intron | hASS1co |
| G9 | AAV8.ApoE.A1AT.IVS2.hASS1co.bGH (p4383) | ApoE-A1AT | IVS2 | hASS1co |
| G10 | AAV8.ApoE.A1AT(full).IVS2.hASS1co.bGH (p4385) | ApoE-A1AT (full) | IVS2 | hASS1co |
| G11 | AAV8.En34.A1AT.PI.hASS1co.bGH (p4340) | En34-A1AT | PI | hASS1co |
| G12 | AAV8.ApoE.A1AT(full).IVS2.hASS1-native.bGH (p4456) | ApoE-A1AT (full) | IVS2 | hASS1-native |
| G13 | AAV8.ApoE.A1AT.IVS2.hASS1-native.bGH (p4457) | ApoE-A1AT | IVS2 | hASS1-native |
| G14 | AAV8.TBG.IVS2.hASS1-native.bGH (p4458) | ABPx2-TBG | IVS2 | hASS1-native |
| G15 | AAV8.EnTTR.TTR.IVS2.hASS1-native.bGH (p4459) | EnTTR-TTR | IVS2 | hASS1-native |

| Grp | Size (bp) (ITR-ITR) | Yield (GC)/ Cellstack | w2 citrulline (μM) Mean ± STD<br>3E11 GC/mouse | 1E11 GC/mouse | w6 citrulline (% reduction)<br>3E11 GC/mouse | 1E11 GC/mouse |
|---|---|---|---|---|---|---|
| G2 | 3325 | 1.21E+14 | 714 ± 161 (n = 5)**** | N.D. | 68.4% | N.D. |
| G3 | 3261 | 8.60E+13 | 564 ± 122 (n = 13)**** | 1065 ± 329 (n = 12) | 75 | 52 |
| G4 | 2777 | 1.26E+14 | 1272 ± 406 (n = 9) | 2176 ± 607 (n = 9) | 43 | 3 |
| G5 | 2121 | 9.90E+13 | 1707 ± 732 (n = 8) | 2328 ± 348 (n = 8) | 24 | −4 |
| G6 | 2083 | 6.60E+13 | 1702 ± 549 (n = 8) | 1808 ± 542 (n = 8) | 24 | 19 |
| G7 | 2777 | 1.17E+14 | 980 ± 231 (n = 8) | 1681 ± 337 (n = 7) | 56 | 25 |
| G8 | 4040 | 1.38E+14 | 1966 ± 319 (n = 8) | 2389 ± 392 (n = 8) | 12 | −7 |
| G9 | 3066 | 6.75E+13 | 591 ± 57 (n = 9)**** | 664 ± 196 (n = 9)** | 74 | 70 |
| G10 | 3216 | 1.01E+14 | 404 ± 45 (n = 9)**** | 509 ± 118 (n = 16)**** | 82 | 77 |
| G11 | 2331 | 1.17E+14 | 746 ± 348 (n = 8)** | 1420 ± 485 (n = 8) | 67 | 37 |

TABLE 1-continued

| Summary of Vectors for liver directed therapy for treatment of citrullinemia | | | | | | |
|---|---|---|---|---|---|---|
| G12 | 3216 | 7.27E+13 | N.D. | 548 ± 111 (n = 10)**** | N.D. | 76 |
| G13 | 3066 | 1.10E+14 | N.D. | 494 ± 148 (n = 10)**** | N.D. | 78 |
| G14 | 3221 | 7.12E+13 | N.D. | 523 ± 147 (n = 9)**** | N.D. | 77 |
| G15 | 2798 | 1.37E+14 | N.D. | 513 ± 119 (n = 10)**** | N.D. | 77 |
| | | Fold | 2239 ± 596 (n = 13) | | | |

spectrum of CTLN1 ranges from a severe neonatal onset form to a milder form with later onset. Affected patients have persistent elevated plasma citrulline levels and are at risk of life-threatening elevation of ammonia that can lead to irreversible cognitive impairment, coma, and death. Current treatment for CTLN1 patients, which includes a low protein diet, supplementation of arginine and administration of nitrogen scavengers, is often unable to prevent ongoing hyperammonemic crises. Liver transplantation has shown successful reduction of plasma ammonia and citrulline levels, but donor liver is limiting, the procedure itself carries significant morbidity, and immunosuppressive drugs are necessary for the duration of the graft. Therefore, there is a need for other approaches to therapy for CTLN1.

AAV vector-based gene therapy provides an alternative to current treatment options as long as the vector delivers sufficient and sustained transgene expression in the liver without substantial toxicity. Several candidate AAV8 vectors for CTLN1 were generated with different liver-specific promoters, introns, and cDNA sequences (native or codon-optimized hASS1 cDNA). In vivo evaluation of vectors was performed in a murine model of CTLN1 ($ASS1^{fold/fold}$). Homozygous $ASS1^{fold/fold}$ (fold) mice carried a hypomorphic mutation and display lethality after weaning. Half of the untreated fold mice perished before the age of 12 weeks old, while a few (5%) lived up to 5 months. In addition to significantly elevated plasma citrulline levels, untreated fold mice had significantly reduced body weight, variable elevated plasma ammonia levels and urine orotic acid levels, and they were not fertile.

Four-week-old fold mice were dosed via retro-orbital or intraperitoneal injection with $3\times10^{11}$ GC or $1\times10^{11}$ GC of vector. Reduction of plasma citrulline levels was chosen as the main criteria to differentiate the performance of different vectors. A lead vector containing the ApoE enhancer-alpha 1 antitrypsin promoter and the beta globulin intervening sequence 2 achieved 77% reduction of citrulline levels two weeks post vector administration at the dose of $1\times10^{11}$ GC. Intron played an important role in expression of ASS1 and vectors carrying the same promoter with other introns, or no intron, showed significantly perturbed efficiency in reducing citrulline levels. Vector with native cDNA sequences performed slightly better than a vector with codon-optimized cDNA sequences. Fold mice treated with the top candidate vectors gained weight, became fertile, and survived more than 9 months (still on-going).

(Sequence Listing Free Text)

The following information is provided for sequences containing free text under numeric identifier <223>.

| SEQ ID NO | Amino Acid or Nucleic Acid Sequence | Free text under <223> | Description |
|---|---|---|---|
| 1 | Amino Acid | | human ASS1 |
| 2 | Nucleic Acid | <223> constructed sequence | engineered cDNA for human ASS1 |
| 3 | Nucleic Acid | | cDNA for native human ASS1 |
| 4 | Nucleic Acid | <223> constructed sequence | En34 enhancer |
| 5 | Nucleic Acid | <223> constructed sequence | EnTTR enhancer |
| 6 | Nucleic Acid | <223> constructed sequence | ABPS enhancer |
| 7 | Nucleic Acid | <223> constructed sequence | ApoE enhancer |
| 8 | Nucleic Acid | <223> constructed sequence | TBG-S1 |
| 9 | Nucleic Acid | <223> constructed sequence | TBG promoter |
| 10 | Nucleic Acid | <223> constructed sequence | Al AT promoter |
| 11 | Nucleic Acid | <223> constructed sequence | TTR promoter |
| 12 | Nucleic Acid | <223> constructed sequence | bGH poly A |
| 13 | Nucleic Acid | <223> constructed sequence | human beta globin IVS2 |
| 14 | Nucleic Acid | <223> constructed sequence | Promega ® chimeric intron |
| 15 | Nucleic Acid | <223> constructed sequence | WPRE |
| 16 | Nucleic Acid | <223> constructed sequence | 5' ITR |
| 17 | Nucleic Acid | <223> constructed sequence | 3' ITR |
| 18 | Nucleic Acid | <223> constructed sequence | hFIX intron |
| 19 | Amino Acid | <223> AAV8 | AAV8 capsid |
| 20 | Nucleic Acid | <223> constructed sequence | A1AT promoter combined with an ApoE enhancer |
| 21 | Nucleic Acid | <223> constructed sequence | liver-specific promoter LSP |
| 22 | Nucleic Acid | <223> constructed sequence | ApoE.A1AT(full).IVS2.hASS1co.bGH cis plasmid |
| 23 | Nucleic Acid | <223> constructed sequence | En34.A1AT.PI.hASS1co.bGH cis plasmid |
| 24 | Nucleic Acid | <223> constructed sequence | TBG.IVS2.hASS1co.bGH cis plasmid |
| 25 | Nucleic Acid | <223> constructed sequence | TBG.PI.hASS1co.WPRE.bGH cis plasmid |
| 26 | Nucleic Acid | <223> constructed sequence | TBG.PI.hASS1co.bGH cis plasmid |
| 27 | Nucleic Acid | <223> constructed sequence | TBG.PI.hASS1-native.bGH cis plasmid |

-continued

| SEQ ID NO | Amino Acid or Nucleic Acid Sequence | Free text under <223> | Description |
|---|---|---|---|
| 28 | Nucleic Acid | <223> constructed sequence | ApoE. A1AT(full).IVS2.hASS1-native.bGH cis plasmid |
| 29 | Nucleic Acid | <223> constructed sequence | ApoE.AlAT.IVS2.hASS1co.bGH cis plasmid |
| 30 | Nucleic Acid | <223> constructed sequence | En34.A1AT.hASS1co.bGH cis plasmid |
| 31 | Nucleic Acid | <223> constructed sequence | EnTTR.TTR.hASS1co.bGH cis plasmid |
| 32 | Nucleic Acid | <223> constructed sequence | TBG.IVS2.hASS1-native.bGH cis plasmid |
| 33 | Nucleic Acid | <223> constructed sequence | TBG.hFIXintron.hASSlco.bGH cis plasmid |
| 34 | Nucleic Acid | <223> constructed sequence | EnTTR.TTRTVS2.hASS1-native.bGH cis plasmid |
| 35 | Nucleic Acid | <223> constructed sequence | ApoE.A1AT.IVS2.hASS1-native.bGH cis plasmid |
| 36 | Nucleic Acid | | AAV8 capsid |

All publications cited in this specification are incorporated herein by reference in their entireties, as are U.S. Provisional Patent Application No. 62/453,424, filed Feb. 1, 2017, and U.S. provisional Patent Application No. 62/469,650, filed Mar. 10, 2017. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant adeno-associated virus (rAAV) useful as a liver-directed therapeutic for citrullinemia, said rAAV comprising an AAV capsid, and a vector genome packaged therein, said vector genome comprising:

(a) an AAV 5' inverted terminal repeat (ITR);

(b) a promoter;

(c) a coding sequence encoding a human argininosuccinate synthase 1 (ASS1);

(d) an AAV 3' ITR, wherein the coding sequence of (c) is SEQ ID NO: 2.

2. The rAAV according to claim 1, wherein the AAV capsid is an AAV8 capsid or variant thereof.

3. The rAAV according to claim 1, wherein the promoter is a thyroxine binding globulin (TBG) promoter.

4. The rAAV according to claim 1, wherein the promoter is an alpha 1 anti-trypsin (A1AT) promoter.

5. The rAAV according to claim 1, wherein the promoter comprises SEQ ID NO: 21.

6. The rAAV according to claim 1, wherein the promoter is a transthyretin promoter (TTR) promoter.

7. The rAAV according to claim 1, wherein the AAV 5' ITR and/or AAV 3' ITR is from AAV2.

8. The rAAV according to claim 1, wherein the vector genome further comprises a polyadenylation (polyA) sequence.

9. The rAAV according to claim 1, wherein the polyA sequence is a bovine growth hormone (bGH) polyA sequence.

10. The rAAV according to claim 1, wherein the vector genome further comprises a woodchuck hepatitis virus post-transcriptional regulatory element (WPRE).

11. The rAAV according to claim 1, wherein the vector genome further comprises an intron.

12. The rAAV according to claim 11, wherein the intron is human beta globin IVS2 or SV40 intron.

13. The rAAV according to claim 1, wherein the vector genome further comprises an enhancer.

14. The rAAV according to claim 13, wherein the enhancer is an APB enhancer, an ABPS enhancer, an alpha mic/bik enhancer, a TTR enhancer, en34, or an ApoE enhancer.

15. The rAAV according to claim 1, wherein the vector genome is about 3 kilobases to about 5.5 kilobases in size.

16. An aqueous suspension suitable for administration to a citrullinemia patient, said suspension comprising an aqueous suspending liquid and about $1\times10^{12}$ genome copies (GC)/mL to about $1\times10^{14}$ GC/mL of a rAAV useful as a liver-directed therapeutic for citrullinemia, said rAAV having an AAV capsid, and having packaged therein a vector genome comprising:

(a) an AAV 5' ITR;
(b) a promoter;
(c) a coding sequence encoding an ASS1; and
(d) an AAV 3' ITR, wherein the coding sequence of (c) is SEQ ID NO: 2.

17. The aqueous suspension according to claim 16, wherein the suspension is suitable for intravenous injection.

18. The aqueous suspension according to claim 16, wherein the suspension further comprises a surfactant, preservative, and/or buffer dissolved in the aqueous suspending liquid.

19. A method of treating a patient having citrullinemia with an rAAV, the method comprising:

administering to the patient about $1\times10^{12}$ to about $1\times10^{14}$ GC/kg of the rAAV according to claim 2 in an aqueous suspension, wherein the GC are calculated by optimized quantitative polymerase chain reaction (oqPCR) or digital droplet polymerase chain reaction (ddPCR).

20. The aqueous suspension according to claim 16, wherein the AAV capsid is an AAV8 capsid.

* * * * *

```
                              SEQUENCE LISTING

<160> NUMBER OF SEQ ID NOS: 36

<210> SEQ ID NO 1
<211> LENGTH: 412
<212> TYPE: PRT
<213> ORGANISM: Homo sapiens

<400> SEQUENCE: 1

Met Ser Ser Lys Gly Ser Val Val Leu Ala Tyr Ser Gly Gly Leu Asp
1               5                   10                  15

Thr Ser Cys Ile Leu Val Trp Leu Lys Glu Gln Gly Tyr Asp Val Ile
            20                  25                  30

Ala Tyr Leu Ala Asn Ile Gly Gln Lys Glu Asp Phe Glu Glu Ala Arg
        35                  40                  45

Lys Lys Ala Leu Lys Leu Gly Ala Lys Lys Val Phe Ile Glu Asp Val
    50                  55                  60

Ser Arg Glu Phe Val Glu Glu Phe Ile Trp Pro Ala Ile Gln Ser Ser
65                  70                  75                  80

Ala Leu Tyr Glu Asp Arg Tyr Leu Leu Gly Thr Ser Leu Ala Arg Pro
                85                  90                  95

Cys Ile Ala Arg Lys Gln Val Glu Ile Ala Gln Arg Glu Gly Ala Lys
            100                 105                 110

Tyr Val Ser His Gly Ala Thr Gly Lys Gly Asn Asp Gln Val Arg Phe
        115                 120                 125

Glu Leu Ser Cys Tyr Ser Leu Ala Pro Gln Ile Lys Val Ile Ala Pro
    130                 135                 140

Trp Arg Met Pro Glu Phe Tyr Asn Arg Phe Lys Gly Arg Asn Asp Leu
145                 150                 155                 160

Met Glu Tyr Ala Lys Gln His Gly Ile Pro Ile Pro Val Thr Pro Lys
                165                 170                 175

Asn Pro Trp Ser Met Asp Glu Asn Leu Met His Ile Ser Tyr Glu Ala
            180                 185                 190

Gly Ile Leu Glu Asn Pro Lys Asn Gln Ala Pro Pro Gly Leu Tyr Thr
        195                 200                 205
```

```
Lys Thr Gln Asp Pro Ala Lys Ala Pro Asn Thr Pro Asp Ile Leu Glu
    210                 215                 220

Ile Glu Phe Lys Lys Gly Val Pro Val Lys Val Thr Asn Val Lys Asp
225                 230                 235                 240

Gly Thr Thr His Gln Thr Ser Leu Glu Leu Phe Met Tyr Leu Asn Glu
                245                 250                 255

Val Ala Gly Lys His Gly Val Gly Arg Ile Asp Ile Val Glu Asn Arg
            260                 265                 270

Phe Ile Gly Met Lys Ser Arg Gly Ile Tyr Glu Thr Pro Ala Gly Thr
        275                 280                 285

Ile Leu Tyr His Ala His Leu Asp Ile Glu Ala Phe Thr Met Asp Arg
    290                 295                 300

Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
                325                 330                 335

Cys Ile Ala Lys Ser Gln Glu Arg Val Glu Gly Lys Val Gln Val Ser
            340                 345                 350

Val Leu Lys Gly Gln Val Tyr Ile Leu Gly Arg Glu Ser Pro Leu Ser
        355                 360                 365

Leu Tyr Asn Glu Glu Leu Val Ser Met Asn Val Gln Gly Asp Tyr Glu
    370                 375                 380

Pro Thr Asp Ala Thr Gly Phe Ile Asn Ile Asn Ser Leu Arg Leu Lys
385                 390                 395                 400

Glu Tyr His Arg Leu Gln Ser Lys Val Thr Ala Lys
                405                 410
```

<210> SEQ ID NO 2
<211> LENGTH: 1236
<212> TYPE: DNA
<213> ORGANISM: Artificial Sequence
<220> FEATURE:
<223> OTHER INFORMATION: constructed sequence

<400> SEQUENCE: 2

```
atgagcagca agggctctgt ggtgctggcc tactctggcg gcctggacac cagctgtatc      60

ctcgtgtggc tgaaagaaca gggctacgac gtgatcgcct acctggccaa catcggccag     120

aaagaggact tcgaggaagc ccggaagaag gccctgaagc tgggcgccaa gaaggtgttc     180

atcgaggacg tgtcccgcga gttcgtggaa gagttcatct ggcccgccat ccagagcagc     240

gccctgtacg aggacagata cctgctgggc accagcctgg ccagaccctg tatcgcccgg     300

aaacaggtgg aaatcgccca gcgcgagggc gccaaatacg tgtctcacgg cgccaccggc     360

aagggcaacg accaggtgcg ctttgagctg agctgctact ccctggcccc ccagatcaaa     420

gtgatcgccc cttggcggat gcccgagttc tacaaccggt tcaagggccg gaacgacctg     480

atggaatacg ccaagcagca cggcatcccc atccccgtga cccccaagaa cccttggagc     540

atggacgaga acctgatgca catcagctac gaggccggca tcctggaaaa ccccaagaat     600

caggcccctc ccggcctgta cacaaagacc caggaccctg ccaaggcccc caacaccccc     660

gacattctgg aaatcgagtt caagaaaggc gtgcccgtga aagtgaccaa cgtgaaggac     720

ggcaccaccc accagacctc cctggaactg ttcatgtacc tgaacgaggt ggccggcaag     780

cacggcgtgg gcagaatcga catcgtggaa aacagattca tcggcatgaa gtcccggggc     840

atctacgaga caccagccgg caccatcctg taccacgccc acctggatat cgaggccttc     900
```

accatggacc gggaagtgcg gaagatcaag cagggcctgg gcctgaagtt cgccgagctg 960
gtgtacacag gcttttggca cagccccgag tgcgagtttg tgcggcactg cattgccaag 1020
agccaggaac gggtggaagg caaggtgcag gtgtccgtgc tgaagggcca ggtgtacatt 1080
ctgggcagag agagcccccct gagcctgtac aacgaggaac tggtgtctat gaacgtgcag 1140
ggcgactacg agcccaccga cgccaccggc ttcatcaaca tcaacagcct gagactgaaa 1200
gagtaccacc ggctgcagtc caaagtgacc gccaag 1236

<210> SEQ ID NO 3
<211> LENGTH: 1236
<212> TYPE: DNA
<213> ORGANISM: Homo sapiens

<400> SEQUENCE: 3
atgtccagca aaggctccgt ggttctggcc tacagtggcg gcctggacac ctcgtgcatc 60
ctcgtgtggc tgaaggaaca aggctatgac gtcattgcct atctggccaa cattggccag 120
aaggaagact tcgaggaagc caggaagaag gcactgaagc ttggggccaa aaaggtgttc 180
attgaggatg tcagcaggga gtttgtggag gagttcatct ggccggccat ccagtccagc 240
gcactgtatg aggaccgcta cctcctgggc acctctcttg ccaggccctg catcgcccgc 300
aaacaagtgg aaatcgccca gcgggagggg gccaagtatg tgtcccacgg cgccacagga 360
aaggggaacg atcaggtccg gtttgagctc agctgctact cactggcccc ccagataaag 420
gtcattgctc cctggaggat gcctgaattc tacaaccggt tcaagggccg caatgacctg 480
atggagtacg caaagcaaca cgggattccc atcccggtca ctcccaagaa cccgtggagc 540
atggatgaga acctcatgca catcagctac gaggctggaa tcctggagaa ccccaagaac 600
caagcgcctc caggtctcta cacgaagacc caggacccag ccaaagcccc caacacccct 660
gacattctcg agatcgagtt caaaaaaggg gtccctgtga aggtgaccaa cgtcaaggat 720
ggcaccaccc accagacctc cttggagctc ttcatgtacc tgaacgaagt cgcgggcaag 780
catggcgtgg gccgtattga catcgtggag aaccgcttca ttggaatgaa gtcccgaggt 840
atctacgaga ccccagcagg caccatcctt taccacgctc atttagacat cgaggccttc 900
accatggacc gggaagtgcg caaaatcaaa caaggcctgg gcttgaaatt tgctgagctg 960
gtgtataccg gtttctggca cagccctgag tgtgaatttg tccgccactg catcgccaag 1020
tcccaggagc gagtggaagg gaaagtgcag gtgtccgtcc tcaagggcca ggtgtacatc 1080
ctcggccggg agtccccact gtctctctac aatgaggagc tggtgagcat gaacgtgcag 1140
ggtgattatg agccaactga tgccaccggg ttcatcaaca tcaattccct caggctgaag 1200
gaatatcatc gtctccagag caaggtcact gccaaa 1236

<210> SEQ ID NO 4
<211> LENGTH: 34
<212> TYPE: DNA
<213> ORGANISM: Artificial Sequence
<220> FEATURE:
<223> OTHER INFORMATION: constructed sequence

<400> SEQUENCE: 4
tgtttgctgc ttgcaatgtt tgcccatttt aggg 34

<210> SEQ ID NO 5
<211> LENGTH: 100
<212> TYPE: DNA

<213> ORGANISM: Artificial Sequence
<220> FEATURE:
<223> OTHER INFORMATION: constructed sequence

<400> SEQUENCE: 5
ctacctcgtg atcgcccggc ccctgttcaa acatgtccta atactctgtc tctgcaaggg 60
tcatcagtag ttttccatct tactcaacat cctcccagtg 100

<210> SEQ ID NO 6
<211> LENGTH: 42
<212> TYPE: DNA
<213> ORGANISM: Artificial Sequence
<220> FEATURE:
<223> OTHER INFORMATION: constructed sequence

<400> SEQUENCE: 6
aggttaattt ttaaactgtt tgctctggtt aataatctca gg 42

<210> SEQ ID NO 7
<211> LENGTH: 322
<212> TYPE: DNA
<213> ORGANISM: Artificial Sequence
<220> FEATURE:
<223> OTHER INFORMATION: constructed sequence

<400> SEQUENCE: 7
aaggctcaga ggcacacagg agtttctggg ctcaccctgc ccccttccaa cccctcagtt 60
cccatcctcc agcagctgtt tgtgtgctgc ctctgaagtc cacactgaac aaacttcagc 120
ctactcatgt ccctaaaatg ggcaaacatt gcaagcagca aacagcaaac acacagccct 180
ccctgcctgc tgaccttgga gctggggcag aggtcagaga cctctctggg cccatgccac 240
ctccaacatc cactcgaccc cttggaattt cggtggagag gagcagaggt tgtcctggcg 300
tggtttaggt agtgtgagag gg 322

<210> SEQ ID NO 8
<211> LENGTH: 176
<212> TYPE: DNA
<213> ORGANISM: Artificial Sequence
<220> FEATURE:
<223> OTHER INFORMATION: constructed sequence

<400> SEQUENCE: 8
actcaaagtt caaaccttat cattttttgc tttgttcctc ttggccttgg ttttgtacat 60
cagctttgaa aataccatcc cagggttaat gctggggtta atttataact aagagtgctc 120
tagttttgca atacaggaca tgctataaaa atggaaagat gttgctttct gagaga 176

<210> SEQ ID NO 9
<211> LENGTH: 477
<212> TYPE: DNA
<213> ORGANISM: Artificial Sequence
<220> FEATURE:
<223> OTHER INFORMATION: constructed sequence

<400> SEQUENCE: 9
agggctggaa gctacctttg acatcatttc ctctgcgaat gcatgtataa tttctacaga 60
acctattaga aaggatcacc cagcctctgc ttttgtacaa ctttccctta aaaaactgcc 120
aattccactg ctgtttggcc caatagtgag aactttttcc tgctgcctct tggtgctttt 180
gcctatggcc cctattctgc ctgctgaaga cactcttgcc agcatggact taaacccctc 240
cagctctgac aatcctcttt ctcttttgtt ttacatgaag ggtctggcag ccaaagcaat 300
cactcaaagt tcaaacctta tcatttttttg ctttgttcct cttggccttg gttttgtaca 360
tcagctttga aaataccatc ccagggttaa tgctggggtt aatttataac taagagtgct 420
ctagttttgc aatacaggac atgctataaa aatggaaaga tgttgctttc tgagaga 477

<210> SEQ ID NO 10
<211> LENGTH: 218
<212> TYPE: DNA
<213> ORGANISM: Artificial Sequence
<220> FEATURE:
<223> OTHER INFORMATION: constructed sequence

<400> SEQUENCE: 10
tggacacagg acgctgtggt ttctgagcca gggggcgact cagatcccag ccagtggact 60
tagcccctgt ttgctcctcc gataactggg gtgaccttgg ttaatattca ccagcagcct 120
cccccgttgc ccctctggat ccactgctta aatacggacg aggacagggc cctgtctcct 180
cagcttcagg caccaccact gacctgggac agtgaata 218

<210> SEQ ID NO 11
<211> LENGTH: 190
<212> TYPE: DNA
<213> ORGANISM: Artificial Sequence
<220> FEATURE:
<223> OTHER INFORMATION: constructed sequence

<400> SEQUENCE: 11
atttcataga acgaatgttc cgatgctcta atctctctag acaaggttca tatttgtatg 60
ggttacttat tctctctttg ttgactaagt caataatcag aatcagcagg tttgcagtca 120
gattggcagg gataagcagc ctagctcagg agaagtgagt ataaaagccc caggctggga 180
gcagccatca 190

<210> SEQ ID NO 12
<211> LENGTH: 215
<212> TYPE: DNA
<213> ORGANISM: Artificial Sequence
<220> FEATURE:
<223> OTHER INFORMATION: constructed sequence

<400> SEQUENCE: 12
gcctcgactg tgccttctag ttgccagcca tctgttgttt gcccctcccc cgtgccttcc 60
ttgaccctgg aaggtgccac tcccactgtc ctttcctaat aaaatgagga aattgcatcg 120
cattgtctga gtaggtgtca ttctattctg gggggtgggg tggggcagga cagcaagggg 180
gaggattggg aagacaatag caggcatgct gggga 215

<210> SEQ ID NO 13
<211> LENGTH: 572
<212> TYPE: DNA
<213> ORGANISM: Artificial Sequence
<220> FEATURE:
<223> OTHER INFORMATION: constructed sequence

<400> SEQUENCE: 13
agcttacttg tggtaccgag ctcggatcct gagaacttca gggtgagtct atgggaccct 60
tgatgttttc tttccccttc ttttctatgg ttaagttcat gtcataggaa ggggagaagt 120
aacagggtac acatattgac caaatcaggg taattttgca tttgtaattt taaaaaatgc 180
tttcttcttt taatatactt ttttgtttat cttatttcta atactttccc taatctcttt 240

-continued

```
ctttcagggc aataatgata caatgtatca tgcctctttg caccattcta aagaataaca    300

gtgataattt ctgggttaag gcaatagcaa tatttctgca tataaatatt tctgcatata    360

aattgtaact gatgtaagag gtttcatatt gctaatagca gctacaatcc agctaccatt    420

ctgcttttat tttatggttg ggataaggct ggattattct gagtccaagc taggcccttt    480

tgctaatcat gttcatacct cttatcttcc tcccacagct cctgggcaac gtgctggtct    540

gtgtgctggc ccatcacttt ggcaaagaat tg                                  572


<210> SEQ ID NO 14
<211> LENGTH: 133
<212> TYPE: DNA
<213> ORGANISM: Artificial Sequence
<220> FEATURE:
<223> OTHER INFORMATION: constructed sequence

<400> SEQUENCE: 14

gtaagtatca aggttacaag acaggtttaa ggagaccaat agaaactggg cttgtcgaga     60

cagagaagac tcttgcgttt ctgataggca cctattggtc ttactgacat ccactttgcc    120

tttctctcca cag                                                       133


<210> SEQ ID NO 15
<211> LENGTH: 542
<212> TYPE: DNA
<213> ORGANISM: Artificial Sequence
<220> FEATURE:
<223> OTHER INFORMATION: constructed sequence

<400> SEQUENCE: 15

aatcaacctc tggattacaa aatttgtgaa agattgactg gtattcttaa ctatgttgct     60

ccttttacgc tatgtggata cgctgcttta atgcctttgt atcatgctat tgcttcccgt    120

atggctttca ttttctcctc cttgtataaa tcctggttgc tgtctcttta tgaggagttg    180

tggcccgttg tcaggcaacg tggcgtggtg tgcactgtgt ttgctgacgc aacccccact    240

ggttggggca ttgccaccac ctgtcagctc ctttccggga ctttcgcttt ccccctccct    300

attgccacgg cggaactcat cgccgcctgc cttgcccgct gctggacagg ggctcggctg    360

ttgggcactg acaattccgt ggtgttgtcg gggaaatcat cgtcctttcc ttggctgctc    420

gcctgtgttg ccacctggat tctgcgcggg acgtccttct gctacgtccc ttcggccctc    480

aatccagcgg accttccttc ccgcggcctg ctgccggctc tgcggcctct tccgcgtctt    540

cg                                                                   542


<210> SEQ ID NO 16
<211> LENGTH: 168
<212> TYPE: DNA
<213> ORGANISM: Artificial Sequence
<220> FEATURE:
<223> OTHER INFORMATION: constructed sequence

<400> SEQUENCE: 16

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacg                 168


<210> SEQ ID NO 17
<211> LENGTH: 168
<212> TYPE: DNA
<213> ORGANISM: Artificial Sequence
```

<220> FEATURE:
<223> OTHER INFORMATION: constructed sequence

<400> SEQUENCE: 17
cgtagataag tagcatggcg ggttaatcat taactacaag gaacccctag tgatggagtt 60
ggccactccc tctctgcgcg ctcgctcgct cactgaggcc gggcgaccaa aggtcgcccg 120
acgcccgggc tttgcccggg cggcctcagt gagcgagcga gcgcgcag 168

<210> SEQ ID NO 18
<211> LENGTH: 1421
<212> TYPE: DNA
<213> ORGANISM: Artificial Sequence
<220> FEATURE:
<223> OTHER INFORMATION: constructed sequence

<400> SEQUENCE: 18
gtttgtttcc ttttttaaaa tacattgagt atgcttgcct tttagatata gaaatatctg 60
atgctgtctt cttcactaaa ttttgattac atgatttgac agcaatattg aagagtctaa 120
cagccagcac gcaggttggt aagtactggt tctttgttag ctaggttttc ttcttcttca 180
tttttaaaac taaatagatc gacaatgctt atgatgcatt tatgtttaat aaacactgtt 240
cagttcatga tttggtcatg taattcctgt tagaaaacat tcatctcctt ggtttaaaaa 300
aattaaaagt gggaaaacaa agaaatagca gaatatagtg aaaaaaaata accacattat 360
ttttgtttgg acttaccact ttgaaatcaa aatgggaaac aaaagcacaa acaatggcct 420
tatttacaca aaaagtctga ttttaagata tatgacattt caaggtttca gaagtatgta 480
atgaggtgtg tctctaattt tttaaattat atatcttcaa tttaaagttt tagttaaaac 540
ataaagatta acctttcatt agcaagctgt tagttatcac caaagctttt catggattag 600
gaaaaaatca ttttgtctct atgtcaaaca tcttggagtt gatatttggg gaaacacaat 660
actcagttga gttccctagg ggagaaaagc aagcttaaga attgacataa agagtaggaa 720
gttagctaat gcaacatata tcactttgtt ttttcacaac tacagtgact ttatgtattt 780
cccagaggaa ggcatacagg gaagaaatta tcccatttgg acaaacagca tgttctcaca 840
ggaagcattt atcacactta cttgtcaact ttctagaatc aaatctagta gctgacagta 900
ccaggatcag ggtgccaac cctaagcacc cccagaaagc tgactggccc tgtggttccc 960
actccagaca tgatgtcagc tggaccataa ttaggcttct gttcttcagg agacatttgt 1020
tcaaagtcat ttgggcaacc atattctgaa aacagcccag ccagggtgat ggatcacttt 1080
gcaaagatcc tcaatgagct attttcaagt gatgacaaag tgtgaagtta accgctcatt 1140
tgagaacttt ctttttcatc caaagtaaat tcaaatatga ttagaaatct gaccttttat 1200
tactggaatt ctcttgacta aaagtaaaat tgaattttaa ttcctaaatc tccatgtgta 1260
tacagtactg tgggaacatc acagattttg gctccatgcc ctaaagagaa attggctttc 1320
agattatttg gattaaaaac aaagactttc ttaagagatg taaaattttc atgatgtttt 1380
cttttttgct aaaactaaag aattattctt ttacatttca g 1421

<210> SEQ ID NO 19
<211> LENGTH: 738
<212> TYPE: PRT
<213> ORGANISM: Unknown
<220> FEATURE:
<223> OTHER INFORMATION: AAV8

<400> SEQUENCE: 19

-continued

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
```

-continued

```
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 20
<211> LENGTH: 735
<212> TYPE: DNA
<213> ORGANISM: Artificial Sequence
<220> FEATURE:
<223> OTHER INFORMATION: constructed sequence

<400> SEQUENCE: 20

```
gctcagaggc acacaggagt ttctgggctc accctgcccc cttccaaccc ctcagttccc      60

atcctccagc agctgtttgt gtgctgcctc tgaagtccac actgaacaaa cttcagccta     120

ctcatgtccc taaaatgggc aaacattgca agcagcaaac agcaaacaca cagccctccc     180

tgcctgctga ccttggagct ggggcagagg tcagagacct ctctgggccc atgccacctc     240
```

-continued caacatccac tcgacccctt ggaatttcgg tggagaggag cagaggttgt cctggcgtgg 300
tttaggtagt gtgagagggc gcgccgatct tgctaccagt ggaacagcca ctaaggattc 360
tgcagtgaga gcagagggcc agctaagtgg tactctccca gagactgtct gactcacgcc 420
accccctcca ccttggacac aggacgctgt ggtttctgag ccaggtacaa tgactccttt 480
cggtaagtgc agtggaagct gtacactgcc caggcaaagc gtccgggcag cgtaggcggg 540
cgactcagat cccagccagt ggacttagcc cctgtttgct cctccgataa ctggggtgac 600
cttggttaat attcaccagc agcctccccc gttgcccctc tggatccact gcttaaatac 660
ggacgaggac agggccctgt ctcctcagct tcaggcacca ccactgacct gggacagtag 720
atctagctta cttgt 735

<210> SEQ ID NO 21
<211> LENGTH: 727
<212> TYPE: DNA
<213> ORGANISM: Artificial Sequence
<220> FEATURE:
<223> OTHER INFORMATION: constructed sequence

<400> SEQUENCE: 21
agttaatttt taaaaagcag tcaaaagtcc aagtgccctt gcgagcattt actctctctg 60
tttgctctgg ttaataatct caggagcaca aacattcctt actagttcta ggagttaatt 120
tttaaaaagc agtcaaaagt ccaagtgccc ttgcgagcat ttactctctc tgtttgctct 180
ggttaataat ctcaggagca caaacattcc ttactagttc tagagcggcc gccagtgtgc 240
tggaattcgg ctttttttagg gctggaagct acctttgaca tcatttcctc tgcgaatgca 300
tgtataattt ctacagaacc tattagaaag gatcacccag cctctgcttt tgtacaactt 360
tcccttaaaa aactgccaat cccactgctg tttggcccaa tagtgagaac tttttcctgc 420
tgcctcttgg tgcttttgcc tatggcccct attctgcctg ctgaagacac tcttgccagc 480
atggacttaa acccctccag ctctgacaat cctctttctc ttttgtttta catgaagggt 540
ctggcagcca aagcaatcac tcaaagttca aaccttatca ttttttgctt tgttcctctt 600
ggccttggtt ttgtacatca gctttgaaaa taccatccca gggttaatgc tggggttaat 660
ttataactga gagtgctcta gttctgcaat acaggacatg ctataaaaat ggaaagatgt 720
tgctttc 727

<210> SEQ ID NO 22
<211> LENGTH: 6026
<212> TYPE: DNA
<213> ORGANISM: Artificial Sequence
<220> FEATURE:
<223> OTHER INFORMATION: constructed sequence

<400> SEQUENCE: 22
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaaggctca gaggcacaca ggagtttctg ggctcaccct 240 gccccccttcc aacccctcag ttcccatcct ccagcagctg tttgtgtgct gcctctgaag 300
tccacactga acaaacttca gcctactcat gtccctaaaa tgggcaaaca ttgcaagcag 360
caaacagcaa acacacagcc ctccctgcct gctgaccttg gagctggggc agaggtcaga 420
gacctctctg ggcccatgcc acctccaaca tccactcgac cccttggaat ttcggtggag 480

-continued

```
aggagcagag gttgtcctgg cgtggtttag gtagtgtgag agggcgcgcc gatcttgcta    540
ccagtggaac agccactaag gattctgcag tgagagcaga gggccagcta agtggtactc    600
tcccagagac tgtctgactc acgccacccc ctccaccttg gacacaggac gctgtggttt    660
ctgagccagg tacaatgact cctttcggta agtgcagtgg aagctgtaca ctgcccaggc    720
aaagcgtccg ggcagcgtag gcgggcgact cagatcccag ccagtggact tagcccctgt    780
ttgctcctcc gataactggg gtgaccttgg ttaatattca ccagcagcct cccccgttgc    840
ccctctggat ccactgctta aatacggacg aggacagggc cctgtctcct cagcttcagg    900
caccaccact gacctgggac agtagatcta gcttacttgt ggtaccgagc tcggatcctg    960
agaacttcag ggtgagtcta tgggaccctt gatgttttct ttccccttct tttctatggt   1020
taagttcatg tcataggaag gggagaagta acagggtaca catattgacc aaatcagggt   1080
aattttgcat ttgtaatttt aaaaaatgct ttcttctttt aatatacttt tttgtttatc   1140
ttatttctaa tactttccct aatctctttc tttcagggca ataatgatac aatgtatcat   1200
gcctctttgc accattctaa agaataacag tgataatttc tgggttaagg caatagcaat   1260
atttctgcat ataaatattt ctgcatataa attgtaactg atgtaagagg tttcatattg   1320
ctaatagcag ctacaatcca gctaccattc tgcttttatt ttatggttgg gataaggctg   1380
gattattctg agtccaagct aggccctttt gctaatcatg ttcatacctc ttatcttcct   1440
cccacagctc ctgggcaacg tgctggtctg tgtgctggcc catcactttg gcaaagaatt   1500
gatctcgagt aactgaaggc ggccgccacc atgagcagca agggctctgt ggtgctggcc   1560
tactctggcg gcctggacac cagctgtatc ctcgtgtggc tgaaagaaca gggctacgac   1620
gtgatcgcct acctggccaa catcggccag aaagaggact tcgaggaagc ccggaagaag   1680
gccctgaagc tgggcgccaa gaaggtgttc atcgaggacg tgtcccgcga gttcgtggaa   1740
gagttcatct ggcccgccat ccagagcagc gccctgtacg aggacagata cctgctgggc   1800
accagcctgg ccagaccctg tatcgcccgg aaacaggtgg aaatcgccca gcgcgagggc   1860
gccaaatacg tgtctcacgg cgccaccggc aagggcaacg accaggtgcg ctttgagctg   1920
agctgctact ccctggcccc ccagatcaaa gtgatcgccc cttggcggat gcccgagttc   1980
tacaaccggt tcaagggccg gaacgacctg atggaatacg ccaagcagca cggcatcccc   2040
atccccgtga cccccaagaa cccttggagc atggacgaga acctgatgca catcagctac   2100
gaggccggca tcctggaaaa ccccaagaat caggcccctc ccggcctgta cacaaagacc   2160
caggaccctg ccaaggcccc caacaccccc gacattctgg aaatcgagtt caagaaaggc   2220
gtgcccgtga aagtgaccaa cgtgaaggac ggcaccaccc accagacctc cctggaactg   2280
ttcatgtacc tgaacgaggt ggccggcaag cacggcgtgg gcagaatcga catcgtggaa   2340
aacagattca tcggcatgaa gtcccggggc atctacgaga caccagccgg caccatcctg   2400
taccacgccc acctggatat cgaggccttc accatggacc gggaagtgcg gaagatcaag   2460
cagggcctgg gcctgaagtt cgccgagctg gtgtacacag gcttttggca cagccccgag   2520
tgcgagtttg tgcggcactg cattgccaag agccaggaac gggtggaagg caaggtgcag   2580
gtgtccgtgc tgaagggcca ggtgtacatt ctgggcagag agagccccct gagcctgtac   2640
aacgaggaac tggtgtctat gaacgtgcag ggcgactacg agcccaccga cgccaccggc   2700
ttcatcaaca tcaacagcct gagactgaaa gagtaccacc ggctgcagtc caaagtgacc   2760
gccaagtgat aagcatgcgg atctgcctcg actgtgcctt ctagttgcca gccatctgtt   2820
```

-continued

```
gtttgcccct cccccgtgcc ttccttgacc ctggaaggtg ccactcccac tgtcctttcc   2880

taataaaatg aggaaattgc atcgcattgt ctgagtaggt gtcattctat tctggggggt   2940

ggggtggggc aggacagcaa gggggaggat tgggaagaca atagcaggca tgctggggac   3000

tcgagttaag ggcgaattcc cgataaggat cttcctagag catggctacg tagataagta   3060

gcatggcggg ttaatcatta actacaagga acccctagtg atggagttgg ccactccctc   3120

tctgcgcgct cgctcgctca ctgaggccgg gcgaccaaag gtcgcccgac gcccgggctt   3180

tgcccgggcg gcctcagtga gcgagcgagc gcgcagcctt aattaaccta attcactggc   3240

cgtcgtttta caacgtcgtg actgggaaaa ccctggcgtt acccaactta atcgccttgc   3300

agcacatccc cctttcgcca gctggcgtaa tagcgaagag gcccgcaccg atcgcccttc   3360

ccaacagttg cgcagcctga atggcgaatg ggacgcgccc tgtagcggcg cattaagcgc   3420

ggcgggtgtg gtggttacgc gcagcgtgac cgctacactt gccagcgccc tagcgcccgc   3480

tcctttcgct ttcttccctt cctttctcgc cacgttcgcc ggctttcccc gtcaagctct   3540

aaatcggggg ctccctttag ggttccgatt tagtgcttta cggcacctcg accccaaaaa   3600

acttgattag ggtgatggtt cacgtagtgg gccatcgccc tgatagacgg tttttcgccc   3660

tttgacgttg gagtccacgt tctttaatag tggactcttg ttccaaactg gaacaacact   3720

caaccctatc tcggtctatt cttttgattt ataagggatt ttgccgattt cggcctattg   3780

gttaaaaaat gagctgattt aacaaaaatt taacgcgaat tttaacaaaa tattaacgct   3840

tacaatttag gtggcacttt tcggggaaat gtgcgcggaa cccctatttg tttatttttc   3900

taaatacatt caaatatgta tccgctcatg agacaataac cctgataaat gcttcaataa   3960

tattgaaaaa ggaagagtat gagtattcaa catttccgtg tcgcccttat tccctttttt   4020

gcggcatttt gccttcctgt ttttgctcac ccagaaacgc tggtgaaagt aaaagatgct   4080

gaagatcagt tgggtgcacg agtgggttac atcgaactgg atctcaacag cggtaagatc   4140

cttgagagtt ttcgccccga agaacgtttt ccaatgatga gcacttttaa agttctgcta   4200

tgtggcgcgg tattatcccg tattgacgcc gggcaagagc aactcggtcg ccgcatacac   4260

tattctcaga atgacttggt tgagtactca ccagtcacag aaaagcatct tacggatggc   4320

atgacagtaa gagaattatg cagtgctgcc ataaccatga gtgataacac tgcggccaac   4380

ttacttctga caacgatcgg aggaccgaag gagctaaccg cttttttgca caacatgggg   4440

gatcatgtaa ctcgccttga tcgttgggaa ccggagctga atgaagccat accaaacgac   4500

gagcgtgaca ccacgatgcc tgtagcaatg gcaacaacgt tgcgcaaact attaactggc   4560

gaactactta ctctagcttc ccggcaacaa ttaatagact ggatggaggc ggataaagtt   4620

gcaggaccac ttctgcgctc ggcccttccg gctggctggt ttattgctga taaatctgga   4680

gccggtgagc gtgggtctcg cggtatcatt gcagcactgg ggccagatgg taagccctcc   4740

cgtatcgtag ttatctacac gacggggagt caggcaacta tggatgaacg aaatagacag   4800

atcgctgaga taggtgcctc actgattaag cattggtaac tgtcagacca agtttactca   4860

tatatacttt agattgattt aaaacttcat ttttaattta aaaggatcta ggtgaagatc   4920

ctttttgata atctcatgac caaaatccct taacgtgagt tttcgttcca ctgagcgtca   4980

gaccccgtag aaaagatcaa aggatcttct tgagatcctt tttttctgcg cgtaatctgc   5040

tgcttgcaaa caaaaaaacc accgctacca gcggtggttt gtttgccgga tcaagagcta   5100

ccaactcttt ttccgaaggt aactggcttc agcagagcgc agataccaaa tactgttctt   5160

ctagtgtagc cgtagttagg ccaccacttc aagaactctg tagcaccgcc tacatacctc   5220
```

gctctgctaa tcctgttacc agtggctgct gccagtggcg ataagtcgtg tcttaccggg 5280
ttggactcaa gacgatagtt accggataag gcgcagcggt cgggctgaac ggggggttcg 5340
tgcacacagc ccagcttgga gcgaacgacc tacaccgaac tgagatacct acagcgtgag 5400
ctatgagaaa gcgccacgct tcccgaaggg agaaaggcgg acaggtatcc ggtaagcggc 5460
agggtcggaa caggagagcg cacgagggag cttccagggg gaaacgcctg gtatctttat 5520
agtcctgtcg ggtttcgcca cctctgactt gagcgtcgat ttttgtgatg ctcgtcaggg 5580
gggcggagcc tatggaaaaa cgccagcaac gcggcctttt tacggttcct ggccttttgc 5640
tggccttttg ctcacatgtt ctttcctgcg ttatcccctg attctgtgga taaccgtatt 5700
accgcctttg agtgagctga taccgctcgc cgcagccgaa cgaccgagcg cagcgagtca 5760
gtgagcgagg aagcggaaga gcgcccaata cgcaaaccgc ctctccccgc gcgttggccg 5820
attcattaat gcagctggca cgacaggttt cccgactgga aagcgggcag tgagcgcaac 5880
gcaattaatg tgagttagct cactcattag gcaccccagg ctttacactt tatgcttccg 5940
gctcgtatgt tgtgtggaat tgtgagcgga taacaatttc acacaggaaa cagctatgac 6000
catgattacg ccagatttaa ttaagg 6026

<210> SEQ ID NO 23
<211> LENGTH: 5141
<212> TYPE: DNA
<213> ORGANISM: Artificial Sequence
<220> FEATURE:
<223> OTHER INFORMATION: constructed sequence

<400> SEQUENCE: 23
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctagc tgtttgctgc ttgcaatgtt tgcccatttt 240
agggtggaca caggacgctg tggtttctga gccagggggc gactcagatc ccagccagtg 300
gacttagccc ctgtttgctc ctccgataac tggggtgacc ttggttaata ttcaccagca 360
gcctcccccg ttgcccctct ggatccactg cttaaatacg gacgaggaca gggccctgtc 420
tcctcagctt caggcaccac cactgacctg ggacagtgaa tctgcagaag ttggtcgtga 480
ggcactgggc aggtaagtat caaggttaca agacaggttt aaggagacca atagaaactg 540
ggcttgtcga gacagagaag actcttgcgt ttctgatagg cacctattgg tcttactgac 600
atccactttg cctttctctc cacaggtgtc caggcggccg ccaccatgag cagcaagggc 660
tctgtggtgc tggcctactc tggcggcctg gacaccagct gtatcctcgt gtggctgaaa 720
gaacagggct acgacgtgat cgcctacctg gccaacatcg gccagaaaga ggacttcgag 780
gaagcccgga agaaggccct gaagctgggc gccaagaagg tgttcatcga ggacgtgtcc 840
cgcgagttcg tggaagagtt catctggccc gccatccaga gcagcgccct gtacgaggac 900
agatacctgc tgggcaccag cctggccaga ccctgtatcg cccggaaaca ggtggaaatc 960
gcccagcgcg agggcgccaa atacgtgtct cacggcgcca ccggcaaggg caacgaccag 1020
gtgcgctttg agctgagctg ctactccctg gccccccaga tcaaagtgat cgccccttgg 1080
cggatgcccg agttctacaa ccggttcaag ggccggaacg acctgatgga atacgccaag 1140
cagcacggca tccccatccc cgtgaccccc aagaaccctt ggagcatgga cgagaacctg 1200

-continued atgcacatca gctacgaggc cggcatcctg gaaaacccca agaatcaggc ccctcccggc 1260
ctgtacacaa agacccagga ccctgccaag gcccccaaca cccccgacat tctggaaatc 1320
gagttcaaga aaggcgtgcc cgtgaaagtg accaacgtga aggacggcac cacccaccag 1380
acctccctgg aactgttcat gtacctgaac gaggtggccg gcaagcacgg cgtgggcaga 1440
atcgacatcg tggaaaacag attcatcggc atgaagtccc ggggcatcta cgagacacca 1500
gccggcacca tcctgtacca cgcccacctg gatatcgagg ccttcaccat ggaccgggaa 1560
gtgcggaaga tcaagcaggg cctgggcctg aagttcgccg agctggtgta cacaggcttt 1620
tggcacagcc ccgagtgcga gtttgtgcgg cactgcattg ccaagagcca ggaacgggtg 1680
gaaggcaagg tgcaggtgtc cgtgctgaag ggccaggtgt acattctggg cagagagagc 1740
cccctgagcc tgtacaacga ggaactggtg tctatgaacg tgcagggcga ctacgagccc 1800
accgacgcca ccggcttcat caacatcaac agcctgagac tgaaagagta ccaccggctg 1860
cagtccaaag tgaccgccaa gtgataagca tgcggatctg cctcgactgt gccttctagt 1920
tgccagccat ctgttgtttg cccctccccc gtgccttcct tgaccctgga aggtgccact 1980
cccactgtcc tttcctaata aaatgaggaa attgcatcgc attgtctgag taggtgtcat 2040
tctattctgg ggggtggggt ggggcaggac agcaaggggg aggattggga agacaatagc 2100
aggcatgctg gggactcgag ttaagggcga attcccgatt aggatcttcc tagagcatgg 2160
ctacgtagat aagtagcatg gcgggttaat cattaactac aaggaacccc tagtgatgga 2220
gttggccact ccctctctgc gcgctcgctc gctcactgag gccgggcgac caaaggtcgc 2280
ccgacgcccg ggctttgccc gggcggcctc agtgagcgag cgagcgcgca gccttaatta 2340
acctaattca ctggccgtcg ttttacaacg tcgtgactgg gaaaaccctg gcgttaccca 2400
acttaatcgc cttgcagcac atcccccttt cgccagctgg cgtaatagcg aagaggcccg 2460
caccgatcgc ccttcccaac agttgcgcag cctgaatggc gaatgggacg cgccctgtag 2520
cggcgcatta agcgcggcgg gtgtggtggt tacgcgcagc gtgaccgcta cacttgccag 2580
cgccctagcg cccgctcctt tcgctttctt cccttccttt ctcgccacgt tcgccggctt 2640
tccccgtcaa gctctaaatc gggggctccc tttagggttc cgatttagtg ctttacggca 2700
cctcgacccc aaaaaacttg attagggtga tggttcacgt agtgggccat cgccctgata 2760
gacggttttt cgccctttga cgttggagtc cacgttcttt aatagtggac tcttgttcca 2820
aactggaaca acactcaacc ctatctcggt ctattctttt gatttataag ggattttgcc 2880
gatttcggcc tattggttaa aaaatgagct gatttaacaa aaatttaacg cgaattttaa 2940
caaaatatta acgcttacaa tttaggtggc acttttcggg gaaatgtgcg cggaacccct 3000
atttgtttat ttttctaaat acattcaaat atgtatccgc tcatgagaca ataaccctga 3060
taaatgcttc aataatattg aaaaaggaag agtatgagta ttcaacattt ccgtgtcgcc 3120
cttattccct tttttgcggc attttgcctt cctgtttttg ctcacccaga aacgctggtg 3180
aaagtaaaag atgctgaaga tcagttgggt gcacgagtgg gttacatcga actggatctc 3240
aacagcggta agatccttga gagttttcgc cccgaagaac gttttccaat gatgagcact 3300
tttaaagttc tgctatgtgg cgcggtatta tcccgtattg acgccgggca agagcaactc 3360
ggtcgccgca tacactattc tcagaatgac ttggttgagt actcaccagt cacagaaaag 3420
catcttacgg atggcatgac agtaagagaa ttatgcagtg ctgccataac catgagtgat 3480
aacactgcgg ccaacttact tctgacaacg atcggaggac cgaaggagct aaccgctttt 3540
ttgcacaaca tgggggatca tgtaactcgc cttgatcgtt gggaaccgga gctgaatgaa 3600

-continued gccataccaa acgacgagcg tgacaccacg atgcctgtag caatggcaac aacgttgcgc 3660
aaactattaa ctggcgaact acttactcta gcttcccggc aacaattaat agactggatg 3720
gaggcggata aagttgcagg accacttctg cgctcggccc ttccggctgg ctggtttatt 3780
gctgataaat ctggagccgg tgagcgtggg tctcgcggta tcattgcagc actggggcca 3840
gatggtaagc cctcccgtat cgtagttatc tacacgacgg ggagtcaggc aactatggat 3900
gaacgaaata gacagatcgc tgagataggt gcctcactga ttaagcattg gtaactgtca 3960
gaccaagttt actcatatat actttagatt gatttaaaac ttcattttta atttaaaagg 4020
atctaggtga agatcctttt tgataatctc atgaccaaaa tcccttaacg tgagttttcg 4080
ttccactgag cgtcagaccc cgtagaaaag atcaaaggat cttcttgaga tccttttttt 4140
ctgcgcgtaa tctgctgctt gcaaacaaaa aaaccaccgc taccagcggt ggtttgtttg 4200
ccggatcaag agctaccaac tctttttccg aaggtaactg gcttcagcag agcgcagata 4260
ccaaatactg ttcttctagt gtagccgtag ttaggccacc acttcaagaa ctctgtagca 4320
ccgcctacat acctcgctct gctaatcctg ttaccagtgg ctgctgccag tggcgataag 4380
tcgtgtctta ccgggttgga ctcaagacga tagttaccgg ataaggcgca gcggtcgggc 4440
tgaacggggg gttcgtgcac acagcccagc ttggagcgaa cgacctacac cgaactgaga 4500
tacctacagc gtgagctatg agaaagcgcc acgcttcccg aagggagaaa ggcggacagg 4560
tatccggtaa gcggcagggt cggaacagga gagcgcacga gggagcttcc agggggaaac 4620
gcctggtatc tttatagtcc tgtcgggttt cgccacctct gacttgagcg tcgatttttg 4680
tgatgctcgt caggggggcg gagcctatgg aaaaacgcca gcaacgcggc ctttttacgg 4740
ttcctggcct tttgctggcc ttttgctcac atgttctttc ctgcgttatc ccctgattct 4800
gtggataacc gtattaccgc ctttgagtga gctgataccg ctcgccgcag ccgaacgacc 4860
gagcgcagcg agtcagtgag cgaggaagcg gaagagcgcc caatacgcaa accgcctctc 4920
cccgcgcgtt ggccgattca ttaatgcagc tggcacgaca ggtttcccga ctggaaagcg 4980
ggcagtgagc gcaacgcaat taatgtgagt tagctcactc attaggcacc ccaggcttta 5040
cactttatgc ttccggctcg tatgttgtgt ggaattgtga gcggataaca atttcacaca 5100
ggaaacagct atgaccatga ttacgccaga tttaattaag g 5141

<210> SEQ ID NO 24
<211> LENGTH: 6071
<212> TYPE: DNA
<213> ORGANISM: Artificial Sequence
<220> FEATURE:
<223> OTHER INFORMATION: constructed sequence

<400> SEQUENCE: 24
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctagg ggggatccac tagtactcga gacctaggag 240
ttaattttta aaaagcagtc aaaagtccaa gtgcccttgc gagcatttac tctctctgtt 300
tgctctggtt aataatctca ggagcacaaa cattccttac tagttctagg agttaatttt 360
taaaaagcag tcaaaagtcc aagtgccctt gcgagcattt actctctctg tttgctctgg 420
ttaataatct caggagcaca aacattcctt actagttcta gagcggccgc cagtgtgctg 480

```
gaattcggct tttttagggc tggaagctac ctttgacatc atttcctctg cgaatgcatg    540
tataatttct acagaaccta ttagaaagga tcacccagcc tctgcttttg tacaactttc    600
ccttaaaaaa ctgccaatcc cactgctgtt tggcccaata gtgagaactt tttcctgctg    660
cctcttggtg cttttgccta tggcccctat tctgcctgct gaagacactc ttgccagcat    720
ggacttaaac ccctccagct ctgacaatcc tctttctctt ttgttttaca tgaagggtct    780
ggcagccaaa gcaatcactc aaagttcaaa ccttatcatt ttttgctttg ttcctcttgg    840
ccttggtttt gtacatcagc tttgaaaata ccatcccagg gttaatgctg gggttaattt    900
ataactgaga gtgctctagt tctgcaatac aggacatgct ataaaaatgg aaagatgttg    960
ctttctgaga gatcagctta cttgtggtac cgagctcgga tcctgagaac ttcagggtga   1020
gtctatggga cccttgatgt tttctttccc cttcttttct atggttaagt tcatgtcata   1080
ggaaggggag aagtaacagg gtacacatat tgaccaaatc agggtaattt tgcatttgta   1140
attttaaaaa atgctttctt cttttaatat acttttttgt ttatcttatt tctaatactt   1200
tccctaatct ctttctttca gggcaataat gatacaatgt atcatgcctc tttgcaccat   1260
tctaaagaat aacagtgata atttctgggt taaggcaata gcaatatttc tgcatataaa   1320
tatttctgca tataaattgt aactgatgta agaggtttca tattgctaat agcagctaca   1380
atccagctac cattctgctt ttattttatg gttgggataa ggctggatta ttctgagtcc   1440
aagctaggcc cttttgctaa tcatgttcat acctcttatc ttcctcccac agctcctggg   1500
caacgtgctg gtctgtgtgc tggcccatca ctttggcaaa gaattgatct cgagtaactg   1560
aaggcggccg ccaccatgag cagcaagggc tctgtggtgc tggcctactc tggcggcctg   1620
gacaccagct gtatcctcgt gtggctgaaa gaacagggct acgacgtgat cgcctacctg   1680
gccaacatcg gccagaaaga ggacttcgag gaagcccgga agaaggccct gaagctgggc   1740
gccaagaagg tgttcatcga ggacgtgtcc cgcgagttcg tggaagagtt catctggccc   1800
gccatccaga gcagcgccct gtacgaggac agatacctgc tgggcaccag cctggccaga   1860
ccctgtatcg cccggaaaca ggtggaaatc gcccagcgcg agggcgccaa atacgtgtct   1920
cacggcgcca ccggcaaggg caacgaccag gtgcgctttg agctgagctg ctactccctg   1980
gccccccaga tcaaagtgat cgccccttgg cggatgcccg agttctacaa ccggttcaag   2040
ggccggaacg acctgatgga atacgccaag cagcacggca tccccatccc cgtgaccccc   2100
aagaaccctt ggagcatgga cgagaacctg atgcacatca gctacgaggc cggcatcctg   2160
gaaaacccca agaatcaggc ccctcccggc ctgtacacaa agacccagga ccctgccaag   2220
gcccccaaca cccccgacat tctggaaatc gagttcaaga aaggcgtgcc cgtgaaagtg   2280
accaacgtga aggacggcac cacccaccag acctccctgg aactgttcat gtacctgaac   2340
gaggtggccg gcaagcacgg cgtgggcaga atcgacatcg tggaaaacag attcatcggc   2400
atgaagtccc ggggcatcta cgagacacca gccggcacca tcctgtacca cgcccacctg   2460
gatatcgagg ccttcaccat ggaccgggaa gtgcggaaga tcaagcaggg cctgggcctg   2520
aagttcgccg agctggtgta cacaggcttt tggcacagcc ccgagtgcga gtttgtgcgg   2580
cactgcattg ccaagagcca ggaacgggtg gaaggcaagg tgcaggtgtc cgtgctgaag   2640
ggccaggtgt acattctggg cagagagagc cccctgagcc tgtacaacga ggaactggtg   2700
tctatgaacg tgcagggcga ctacgagccc accgacgcca ccggcttcat caacatcaac   2760
agcctgagac tgaaagagta ccaccggctg cagtccaaag tgaccgccaa gtgataagca   2820
tgcggatctg cctcgactgt gccttctagt tgccagccat ctgttgtttg cccctccccc   2880
```

gtgccttcct tgaccctgga aggtgccact cccactgtcc tttcctaata aaatgaggaa 2940
attgcatcgc attgtctgag taggtgtcat tctattctgg ggggtggggt ggggcaggac 3000
agcaaggggg aggattggga agacaatagc aggcatgctg gggactcgag ttaagggcga 3060
attcccgatt aggatcttcc tagagcatgg ctacgtagat aagtagcatg gcgggttaat 3120
cattaactac aaggaacccc tagtgatgga gttggccact ccctctctgc gcgctcgctc 3180
gctcactgag gccgggcgac caaaggtcgc ccgacgcccg ggctttgccc gggcggcctc 3240
agtgagcgag cgagcgcgca gccttaatta acctaattca ctggccgtcg ttttacaacg 3300
tcgtgactgg gaaaaccctg gcgttaccca acttaatcgc cttgcagcac atcccccttt 3360
cgccagctgg cgtaatagcg aagaggcccg caccgatcgc ccttcccaac agttgcgcag 3420
cctgaatggc gaatgggacg cgccctgtag cggcgcatta agcgcggcgg gtgtggtggt 3480
tacgcgcagc gtgaccgcta cacttgccag cgccctagcg cccgctcctt tcgctttctt 3540
cccttccttt ctcgccacgt tcgccggctt tccccgtcaa gctctaaatc gggggctccc 3600
tttagggttc cgatttagtg ctttacggca cctcgacccc aaaaaacttg attagggtga 3660
tggttcacgt agtgggccat cgccctgata gacggttttt cgccctttga cgttggagtc 3720
cacgttcttt aatagtggac tcttgttcca aactggaaca acactcaacc ctatctcggt 3780
ctattctttt gatttataag ggattttgcc gatttcggcc tattggttaa aaaatgagct 3840
gatttaacaa aaatttaacg cgaattttaa caaaatatta acgcttacaa tttaggtggc 3900
acttttcggg gaaatgtgcg cggaacccct atttgtttat ttttctaaat acattcaaat 3960
atgtatccgc tcatgagaca ataaccctga taaatgcttc aataatattg aaaaaggaag 4020
agtatgagta ttcaacattt ccgtgtcgcc cttattccct tttttgcggc attttgcctt 4080
cctgtttttg ctcacccaga aacgctggtg aaagtaaaag atgctgaaga tcagttgggt 4140
gcacgagtgg gttacatcga actggatctc aacagcggta agatccttga gagttttcgc 4200
cccgaagaac gttttccaat gatgagcact tttaaagttc tgctatgtgg cgcggtatta 4260
tcccgtattg acgccgggca agagcaactc ggtcgccgca tacactattc tcagaatgac 4320
ttggttgagt actcaccagt cacagaaaag catcttacgg atggcatgac agtaagagaa 4380
ttatgcagtg ctgccataac catgagtgat aacactgcgg ccaacttact tctgacaacg 4440
atcggaggac cgaaggagct aaccgctttt ttgcacaaca tgggggatca tgtaactcgc 4500
cttgatcgtt gggaaccgga gctgaatgaa gccataccaa acgacgagcg tgacaccacg 4560
atgcctgtag caatggcaac aacgttgcgc aaactattaa ctggcgaact acttactcta 4620
gcttcccggc aacaattaat agactggatg gaggcggata aagttgcagg accacttctg 4680
cgctcggccc ttccggctgg ctggtttatt gctgataaat ctggagccgg tgagcgtggg 4740
tctcgcggta tcattgcagc actggggcca gatggtaagc cctcccgtat cgtagttatc 4800
tacacgacgg ggagtcaggc aactatggat gaacgaaata gacagatcgc tgagataggt 4860
gcctcactga ttaagcattg gtaactgtca gaccaagttt actcatatat actttagatt 4920
gatttaaaac ttcattttta atttaaaagg atctaggtga agatcctttt tgataatctc 4980
atgaccaaaa tcccttaacg tgagttttcg ttccactgag cgtcagaccc cgtagaaaag 5040
atcaaaggat cttcttgaga tccttttttt ctgcgcgtaa tctgctgctt gcaaacaaaa 5100
aaaccaccgc taccagcggt ggtttgtttg ccggatcaag agctaccaac tctttttccg 5160
aaggtaactg gcttcagcag agcgcagata ccaaatactg ttcttctagt gtagccgtag 5220
ttaggccacc acttcaagaa ctctgtagca ccgcctacat acctcgctct gctaatcctg 5280
ttaccagtgg ctgctgccag tggcgataag tcgtgtctta ccgggttgga ctcaagacga 5340
tagttaccgg ataaggcgca gcggtcgggc tgaacggggg gttcgtgcac acagcccagc 5400
ttggagcgaa cgacctacac cgaactgaga tacctacagc gtgagctatg agaaagcgcc 5460
acgcttcccg aagggagaaa ggcggacagg tatccggtaa gcggcagggt cggaacagga 5520
gagcgcacga gggagcttcc agggggaaac gcctggtatc tttatagtcc tgtcgggttt 5580
cgccacctct gacttgagcg tcgatttttg tgatgctcgt caggggggcg gagcctatgg 5640
aaaaacgcca gcaacgcggc ctttttacgg ttcctggcct tttgctggcc ttttgctcac 5700
atgttctttc ctgcgttatc ccctgattct gtggataacc gtattaccgc ctttgagtga 5760
gctgataccg ctcgccgcag ccgaacgacc gagcgcagcg agtcagtgag cgaggaagcg 5820
gaagagcgcc caatacgcaa accgcctctc cccgcgcgtt ggccgattca ttaatgcagc 5880
tggcacgaca ggtttcccga ctggaaagcg ggcagtgagc gcaacgcaat taatgtgagt 5940
tagctcactc attaggcacc ccaggcttta cactttatgc ttccggctcg tatgttgtgt 6000
ggaattgtga gcggataaca atttcacaca ggaaacagct atgaccatga ttacgccaga 6060
tttaattaag g 6071

<210> SEQ ID NO 25
<211> LENGTH: 6135
<212> TYPE: DNA
<213> ORGANISM: Artificial Sequence
<220> FEATURE:
<223> OTHER INFORMATION: constructed sequence

<400> SEQUENCE: 25
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctagc aggttaattt ttaaaaagca gtcaaaagtc 240
caagtggccc ttggcagcat ttactctctc tgtttgctct ggttaataat ctcaggagca 300
caaacattcc agatccaggt taatttttaa aaagcagtca aaagtccaag tggcccttgg 360
cagcatttac tctctctgtt tgctctggtt aataatctca ggagcacaaa cattccagat 420
ccggcgcgcc agggctggaa gctacctttg acatcatttc ctctgcgaat gcatgtataa 480
tttctacaga acctattaga aaggatcacc cagcctctgc ttttgtacaa ctttccctta 540
aaaaactgcc aattccactg ctgtttggcc caatagtgag aactttttcc tgctgcctct 600
tggtgctttt gcctatggcc cctattctgc ctgctgaaga cactcttgcc agcatggact 660
taaacccctc cagctctgac aatcctcttt ctcttttgtt ttacatgaag ggtctggcag 720
ccaaagcaat cactcaaagt tcaaacctta tcattttttg ctttgttcct cttggccttg 780
gttttgtaca tcagctttga aaataccatc ccagggttaa tgctggggtt aatttataac 840
taagagtgct ctagttttgc aatacaggac atgctataaa aatggaaaga tgttgctttc 900
tgagagactg cagaagttgg tcgtgaggca ctgggcaggt aagtatcaag gttacaagac 960
aggtttaagg agaccaatag aaactgggct tgtcgagaca gagaagactc ttgcgtttct 1020
gataggcacc tattggtctt actgacatcc actttgcctt tctctccaca ggtgtccagg 1080
cggccgccac catgagcagc aagggctctg tggtgctggc ctactctggc ggcctggaca 1140
ccagctgtat cctcgtgtgg ctgaaagaac agggctacga cgtgatcgcc tacctggcca 1200

-continued acatcggcca gaaagaggac ttcgaggaag cccggaagaa ggccctgaag ctgggcgcca 1260
agaaggtgtt catcgaggac gtgtcccgcg agttcgtgga agagttcatc tggcccgcca 1320
tccagagcag cgccctgtac gaggacagat acctgctggg caccagcctg gccagaccct 1380
gtatcgcccg gaaacaggtg gaaatcgccc agcgcgaggg cgccaaatac gtgtctcacg 1440
gcgccaccgg caagggcaac gaccaggtgc gctttgagct gagctgctac tccctggccc 1500
cccagatcaa agtgatcgcc ccttggcgga tgcccgagtt ctacaaccgg ttcaagggcc 1560
ggaacgacct gatggaatac gccaagcagc acggcatccc catccccgtg acccccaaga 1620
acccttggag catggacgag aacctgatgc acatcagcta cgaggccggc atcctggaaa 1680
accccaagaa tcaggcccct cccggcctgt acacaaagac ccaggaccct gccaaggccc 1740
ccaacacccc cgacattctg gaaatcgagt tcaagaaagg cgtgcccgtg aaagtgacca 1800
acgtgaagga cggcaccacc caccagacct ccctggaact gttcatgtac ctgaacgagg 1860
tggccggcaa gcacggcgtg ggcagaatcg acatcgtgga aaacagattc atcggcatga 1920
agtcccgggg catctacgag acaccagccg gcaccatcct gtaccacgcc cacctggata 1980
tcgaggcctt caccatggac cgggaagtgc ggaagatcaa gcagggcctg ggcctgaagt 2040
tcgccgagct ggtgtacaca ggcttttggc acagccccga gtgcgagttt gtgcggcact 2100
gcattgccaa gagccaggaa cgggtggaag gcaaggtgca ggtgtccgtg ctgaagggcc 2160
aggtgtacat tctgggcaga gagagccccc tgagcctgta caacgaggaa ctggtgtcta 2220
tgaacgtgca gggcgactac gagcccaccg acgccaccgg cttcatcaac atcaacagcc 2280
tgagactgaa agagtaccac cggctgcagt ccaaagtgac cgccaagtga taagcatgcg 2340
gatccaatca acctctggat tacaaaattt gtgaaagatt gactggtatt cttaactatg 2400
ttgctccttt tacgctatgt ggatacgctg ctttaatgcc tttgtatcat gctattgctt 2460
cccgtatggc tttcattttc tcctccttgt ataaatcctg gttgctgtct ctttatgagg 2520
agttgtggcc cgttgtcagg caacgtggcg tggtgtgcac tgtgtttgct gacgcaaccc 2580
ccactggttg gggcattgcc accacctgtc agctcctttc cgggactttc gctttccccc 2640
tccctattgc cacggcggaa ctcatcgccg cctgccttgc ccgctgctgg acaggggctc 2700
ggctgttggg cactgacaat tccgtggtgt tgtcggggaa gctgacgtcc tttccatggc 2760
tgctcgcctg tgttgccacc tggattctgc gcgggacgtc cttctgctac gtcccttcgg 2820
ccctcaatcc agcggacctt ccttcccgcg gcctgctgcc ggctctgcgg cctcttccgc 2880
gtcttcgaga tctgcctcga ctgtgccttc tagttgccag ccatctgttg tttgcccctc 2940
ccccgtgcct tccttgaccc tggaaggtgc cactcccact gtcctttcct aataaaatga 3000
ggaaattgca tcgcattgtc tgagtaggtg tcattctatt ctggggggtg gggtggggca 3060
ggacagcaag ggggaggatt gggaagacaa tagcaggcat gctggggact cgagttaagg 3120
gcgaattccc gattaggatc ttcctagagc atggctacgt agataagtag catggcgggt 3180
taatcattaa ctacaaggaa cccctagtga tggagttggc cactccctct ctgcgcgctc 3240
gctcgctcac tgaggccggg cgaccaaagg tcgcccgacg cccgggcttt gcccgggcgg 3300
cctcagtgag cgagcgagcg cgcagcctta attaacctaa ttcactggcc gtcgttttac 3360
aacgtcgtga ctgggaaaac cctggcgtta cccaacttaa tcgccttgca gcacatcccc 3420
ctttcgccag ctggcgtaat agcgaagagg cccgcaccga tcgcccttcc caacagttgc 3480
gcagcctgaa tggcgaatgg gacgcgccct gtagcggcgc attaagcgcg gcgggtgtgg 3540

-continued

```
tggttacgcg cagcgtgacc gctacacttg ccagcgccct agcgcccgct cctttcgctt   3600
tcttcccttc ctttctcgcc acgttcgccg gctttccccg tcaagctcta aatcgggggc   3660
tccctttagg gttccgattt agtgctttac ggcacctcga ccccaaaaaa cttgattagg   3720
gtgatggttc acgtagtggg ccatcgccct gatagacggt ttttcgccct ttgacgttgg   3780
agtccacgtt ctttaatagt ggactcttgt tccaaactgg aacaacactc aaccctatct   3840
cggtctattc ttttgattta taagggattt tgccgatttc ggcctattgg ttaaaaaatg   3900
agctgattta acaaaaattt aacgcgaatt ttaacaaaat attaacgctt acaatttagg   3960
tggcactttt cggggaaatg tgcgcggaac ccctatttgt ttatttttct aaatacattc   4020
aaatatgtat ccgctcatga gacaataacc ctgataaatg cttcaataat attgaaaaag   4080
gaagagtatg agtattcaac atttccgtgt cgcccttatt cccttttttg cggcattttg   4140
ccttcctgtt tttgctcacc cagaaacgct ggtgaaagta aaagatgctg aagatcagtt   4200
gggtgcacga gtgggttaca tcgaactgga tctcaacagc ggtaagatcc ttgagagttt   4260
tcgccccgaa gaacgttttc caatgatgag cacttttaaa gttctgctat gtggcgcggt   4320
attatcccgt attgacgccg ggcaagagca actcggtcgc cgcatacact attctcagaa   4380
tgacttggtt gagtactcac cagtcacaga aaagcatctt acggatggca tgacagtaag   4440
agaattatgc agtgctgcca taaccatgag tgataacact gcggccaact tacttctgac   4500
aacgatcgga ggaccgaagg agctaaccgc ttttttgcac aacatggggg atcatgtaac   4560
tcgccttgat cgttgggaac cggagctgaa tgaagccata ccaaacgacg agcgtgacac   4620
cacgatgcct gtagcaatgg caacaacgtt gcgcaaacta ttaactggcg aactacttac   4680
tctagcttcc cggcaacaat taatagactg gatggaggcg gataaagttg caggaccact   4740
tctgcgctcg gcccttccgg ctggctggtt tattgctgat aaatctggag ccggtgagcg   4800
tgggtctcgc ggtatcattg cagcactggg gccagatggt aagccctccc gtatcgtagt   4860
tatctacacg acggggagtc aggcaactat ggatgaacga aatagacaga tcgctgagat   4920
aggtgcctca ctgattaagc attggtaact gtcagaccaa gtttactcat atatacttta   4980
gattgattta aaacttcatt tttaatttaa aaggatctag gtgaagatcc tttttgataa   5040
tctcatgacc aaaatccctt aacgtgagtt ttcgttccac tgagcgtcag accccgtaga   5100
aaagatcaaa ggatcttctt gagatccttt ttttctgcgc gtaatctgct gcttgcaaac   5160
aaaaaaacca ccgctaccag cggtggtttg tttgccggat caagagctac caactctttt   5220
tccgaaggta actggcttca gcagagcgca gataccaaat actgttcttc tagtgtagcc   5280
gtagttaggc caccacttca agaactctgt agcaccgcct acatacctcg ctctgctaat   5340
cctgttacca gtggctgctg ccagtggcga taagtcgtgt cttaccgggt tggactcaag   5400
acgatagtta ccggataagg cgcagcggtc gggctgaacg gggggttcgt gcacacagcc   5460
cagcttggag cgaacgacct acaccgaact gagataccta cagcgtgagc tatgagaaag   5520
cgccacgctt cccgaaggga gaaaggcgga caggtatccg gtaagcggca gggtcggaac   5580
aggagagcgc acgagggagc ttccaggggg aaacgcctgg tatctttata gtcctgtcgg   5640
gtttcgccac ctctgacttg agcgtcgatt tttgtgatgc tcgtcagggg ggcggagcct   5700
atggaaaaac gccagcaacg cggccttttt acggttcctg gccttttgct ggccttttgc   5760
tcacatgttc tttcctgcgt tatcccctga ttctgtggat aaccgtatta ccgcctttga   5820
gtgagctgat accgctcgcc gcagccgaac gaccgagcgc agcgagtcag tgagcgagga   5880
agcggaagag cgcccaatac gcaaaccgcc tctccccgcg cgttggccga ttcattaatg   5940
```

cagctggcac gacaggtttc ccgactggaa agcgggcagt gagcgcaacg caattaatgt 6000
gagttagctc actcattagg caccccaggc tttacacttt atgcttccgg ctcgtatgtt 6060
gtgtggaatt gtgagcggat aacaatttca cacaggaaac agctatgacc atgattacgc 6120
cagatttaat taagg 6135

<210> SEQ ID NO 26
<211> LENGTH: 5587
<212> TYPE: DNA
<213> ORGANISM: Artificial Sequence
<220> FEATURE:
<223> OTHER INFORMATION: constructed sequence

<400> SEQUENCE: 26
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctagc aggttaattt ttaaaaagca gtcaaaagtc 240
caagtggccc ttggcagcat ttactctctc tgtttgctct ggttaataat ctcaggagca 300
caaacattcc agatccaggt taatttttaa aaagcagtca aaagtccaag tggcccttgg 360
cagcatttac tctctctgtt tgctctggtt aataatctca ggagcacaaa cattccagat 420
ccggcgcgcc agggctggaa gctacctttg acatcatttc ctctgcgaat gcatgtataa 480
tttctacaga acctattaga aaggatcacc cagcctctgc ttttgtacaa ctttccctta 540
aaaaactgcc aattccactg ctgtttggcc caatagtgag aactttttcc tgctgcctct 600
tggtgctttt gcctatggcc cctattctgc ctgctgaaga cactcttgcc agcatggact 660
taaacccctc cagctctgac aatcctcttt ctcttttgtt ttacatgaag ggtctggcag 720
ccaaagcaat cactcaaagt tcaaacctta tcatttttg ctttgttcct cttggccttg 780
gttttgtaca tcagctttga aaataccatc ccagggttaa tgctggggtt aatttataac 840
taagagtgct ctagttttgc aatacaggac atgctataaa aatggaaaga tgttgctttc 900
tgagagactg cagaagttgg tcgtgaggca ctgggcaggt aagtatcaag gttacaagac 960
aggtttaagg agaccaatag aaactgggct tgtcgagaca gagaagactc ttgcgtttct 1020
gataggcacc tattggtctt actgacatcc actttgcctt tctctccaca ggtgtccagg 1080
cggccgccac catgagcagc aagggctctg tggtgctggc ctactctggc ggcctggaca 1140
ccagctgtat cctcgtgtgg ctgaaagaac agggctacga cgtgatcgcc tacctggcca 1200
acatcggcca gaaagaggac ttcgaggaag cccggaagaa ggccctgaag ctgggcgcca 1260
agaaggtgtt catcgaggac gtgtcccgcg agttcgtgga agagttcatc tggcccgcca 1320
tccagagcag cgccctgtac gaggacagat acctgctggg caccagcctg gccagaccct 1380
gtatcgcccg gaaacaggtg gaaatcgccc agcgcgaggg cgccaaatac gtgtctcacg 1440
gcgccaccgg caagggcaac gaccaggtgc gctttgagct gagctgctac tccctggccc 1500
cccagatcaa agtgatcgcc ccttggcgga tgcccgagtt ctacaaccgg ttcaagggcc 1560
ggaacgacct gatggaatac gccaagcagc acggcatccc catccccgtg acccccaaga 1620
acccttggag catggacgag aacctgatgc acatcagcta cgaggccggc atcctggaaa 1680
accccaagaa tcaggcccct cccggcctgt acacaaagac ccaggaccct gccaaggccc 1740
ccaacacccc cgacattctg gaaatcgagt tcaagaaagg cgtgcccgtg aaagtgacca 1800

-continued acgtgaagga cggcaccacc caccagacct ccctggaact gttcatgtac ctgaacgagg 1860
tggccggcaa gcacggcgtg ggcagaatcg acatcgtgga aaacagattc atcggcatga 1920
agtcccgggg catctacgag acaccagccg gcaccatcct gtaccacgcc cacctggata 1980
tcgaggcctt caccatggac cgggaagtgc ggaagatcaa gcagggcctg ggcctgaagt 2040
tcgccgagct ggtgtacaca ggcttttggc acagccccga gtgcgagttt gtgcggcact 2100
gcattgccaa gagccaggaa cgggtggaag gcaaggtgca ggtgtccgtg ctgaagggcc 2160
aggtgtacat tctgggcaga gagagccccc tgagcctgta caacgaggaa ctggtgtcta 2220
tgaacgtgca gggcgactac gagcccaccg acgccaccgg cttcatcaac atcaacagcc 2280
tgagactgaa agagtaccac cggctgcagt ccaaagtgac cgccaagtga taagcatgcg 2340
gatctgcctc gactgtgcct tctagttgcc agccatctgt tgtttgcccc tcccccgtgc 2400
cttccttgac cctggaaggt gccactccca ctgtcctttc ctaataaaat gaggaaattg 2460
catcgcattg tctgagtagg tgtcattcta ttctgggggg tggggtgggg caggacagca 2520
agggggagga ttgggaagac aatagcaggc atgctgggga ctcgagttaa gggcgaattc 2580
ccgattagga tcttcctaga gcatggctac gtagataagt agcatggcgg gttaatcatt 2640
aactacaagg aacccctagt gatggagttg gccactccct ctctgcgcgc tcgctcgctc 2700
actgaggccg ggcgaccaaa ggtcgcccga cgcccgggct ttgcccgggc ggcctcagtg 2760
agcgagcgag cgcgcagcct taattaacct aattcactgg ccgtcgtttt acaacgtcgt 2820
gactgggaaa accctggcgt tacccaactt aatcgccttg cagcacatcc ccctttcgcc 2880
agctggcgta atagcgaaga ggcccgcacc gatcgccctt cccaacagtt gcgcagcctg 2940
aatggcgaat gggacgcgcc ctgtagcggc gcattaagcg cggcgggtgt ggtggttacg 3000
cgcagcgtga ccgctacact tgccagcgcc ctagcgcccg ctcctttcgc tttcttccct 3060
tcctttctcg ccacgttcgc cggctttccc cgtcaagctc taaatcgggg gctcccttta 3120
gggttccgat ttagtgcttt acggcacctc gaccccaaaa aacttgatta gggtgatggt 3180
tcacgtagtg ggccatcgcc ctgatagacg gtttttcgcc ctttgacgtt ggagtccacg 3240
ttctttaata gtggactctt gttccaaact ggaacaacac tcaaccctat ctcggtctat 3300
tcttttgatt tataagggat tttgccgatt tcggcctatt ggttaaaaaa tgagctgatt 3360
taacaaaaat ttaacgcgaa ttttaacaaa atattaacgc ttacaattta ggtggcactt 3420
ttcggggaaa tgtgcgcgga acccctattt gtttattttt ctaaatacat tcaaatatgt 3480
atccgctcat gagacaataa ccctgataaa tgcttcaata atattgaaaa aggaagagta 3540
tgagtattca acatttccgt gtcgccctta ttcccttttt tgcggcattt tgccttcctg 3600
tttttgctca cccagaaacg ctggtgaaag taaaagatgc tgaagatcag ttgggtgcac 3660
gagtgggtta catcgaactg gatctcaaca gcggtaagat ccttgagagt tttcgccccg 3720
aagaacgttt tccaatgatg agcactttta aagttctgct atgtggcgcg gtattatccc 3780
gtattgacgc cgggcaagag caactcggtc gccgcataca ctattctcag aatgacttgg 3840
ttgagtactc accagtcaca gaaaagcatc ttacggatgg catgacagta agagaattat 3900
gcagtgctgc cataaccatg agtgataaca ctgcggccaa cttacttctg acaacgatcg 3960
gaggaccgaa ggagctaacc gcttttttgc acaacatggg ggatcatgta actcgccttg 4020
atcgttggga accggagctg aatgaagcca taccaaacga cgagcgtgac accacgatgc 4080
ctgtagcaat ggcaacaacg ttgcgcaaac tattaactgg cgaactactt actctagctt 4140
cccggcaaca attaatagac tggatggagg cggataaagt tgcaggacca cttctgcgct 4200
cggcccttcc ggctggctgg tttattgctg ataaatctgg agccggtgag cgtgggtctc 4260
gcggtatcat tgcagcactg gggccagatg gtaagccctc ccgtatcgta gttatctaca 4320
cgacggggag tcaggcaact atggatgaac gaaatagaca gatcgctgag ataggtgcct 4380
cactgattaa gcattggtaa ctgtcagacc aagtttactc atatatactt tagattgatt 4440
taaaacttca tttttaattt aaaaggatct aggtgaagat cctttttgat aatctcatga 4500
ccaaaatccc ttaacgtgag ttttcgttcc actgagcgtc agaccccgta gaaaagatca 4560
aaggatcttc ttgagatcct ttttttctgc gcgtaatctg ctgcttgcaa acaaaaaaac 4620
caccgctacc agcggtggtt tgtttgccgg atcaagagct accaactctt tttccgaagg 4680
taactggctt cagcagagcg cagataccaa atactgttct tctagtgtag ccgtagttag 4740
gccaccactt caagaactct gtagcaccgc ctacatacct cgctctgcta atcctgttac 4800
cagtggctgc tgccagtggc gataagtcgt gtcttaccgg gttggactca agacgatagt 4860
taccggataa ggcgcagcgg tcgggctgaa cggggggttc gtgcacacag cccagcttgg 4920
agcgaacgac ctacaccgaa ctgagatacc tacagcgtga gctatgagaa agcgccacgc 4980
ttcccgaagg gagaaaggcg gacaggtatc cggtaagcgg cagggtcgga acaggagagc 5040
gcacgaggga gcttccaggg ggaaacgcct ggtatcttta tagtcctgtc gggtttcgcc 5100
acctctgact tgagcgtcga tttttgtgat gctcgtcagg ggggcggagc ctatggaaaa 5160
acgccagcaa cgcggccttt ttacggttcc tggccttttg ctggcctttt gctcacatgt 5220
tctttcctgc gttatcccct gattctgtgg ataaccgtat taccgccttt gagtgagctg 5280
ataccgctcg ccgcagccga acgaccgagc gcagcgagtc agtgagcgag gaagcggaag 5340
agcgcccaat acgcaaaccg cctctccccg cgcgttggcc gattcattaa tgcagctggc 5400
acgacaggtt tcccgactgg aaagcgggca gtgagcgcaa cgcaattaat gtgagttagc 5460
tcactcatta ggcaccccag gctttacact ttatgcttcc ggctcgtatg ttgtgtggaa 5520
ttgtgagcgg ataacaattt cacacaggaa acagctatga ccatgattac gccagattta 5580
attaagg 5587

<210> SEQ ID NO 27
<211> LENGTH: 5587
<212> TYPE: DNA
<213> ORGANISM: Artificial Sequence
<220> FEATURE:
<223> OTHER INFORMATION: constructed sequence

<400> SEQUENCE: 27
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctagc aggttaattt ttaaaaagca gtcaaaagtc 240
caagtggccc ttggcagcat ttactctctc tgtttgctct ggttaataat ctcaggagca 300
caaacattcc agatccaggt taatttttaa aaagcagtca aaagtccaag tggcccttgg 360
cagcatttac tctctctgtt tgctctggtt aataatctca ggagcacaaa cattccagat 420
ccggcgcgcc agggctggaa gctacctttg acatcatttc ctctgcgaat gcatgtataa 480
tttctacaga acctattaga aaggatcacc cagcctctgc ttttgtacaa ctttccctta 540
aaaaactgcc aattccactg ctgtttggcc caatagtgag aactttttcc tgctgcctct 600

-continued

```
tggtgctttt gcctatggcc cctattctgc ctgctgaaga cactcttgcc agcatggact    660
taaacccctc cagctctgac aatcctcttt ctcttttgtt ttacatgaag ggtctggcag    720
ccaaagcaat cactcaaagt tcaaacctta tcattttttg ctttgttcct cttggccttg    780
gttttgtaca tcagctttga aaataccatc ccagggttaa tgctggggtt aatttataac    840
taagagtgct ctagttttgc aatacaggac atgctataaa aatggaaaga tgttgctttc    900
tgagagactg cagaagttgg tcgtgaggca ctgggcaggt aagtatcaag gttacaagac    960
aggtttaagg agaccaatag aaactgggct tgtcgagaca gagaagactc ttgcgtttct   1020
gataggcacc tattggtctt actgacatcc actttgcctt tctctccaca ggtgtccagg   1080
cggccgccac catgtccagc aaaggctccg tggttctggc ctacagtggc ggcctggaca   1140
cctcgtgcat cctcgtgtgg ctgaaggaac aaggctatga cgtcattgcc tatctggcca   1200
acattggcca gaaggaagac ttcgaggaag ccaggaagaa ggcactgaag cttggggcca   1260
aaaaggtgtt cattgaggat gtcagcaggg agtttgtgga ggagttcatc tggccggcca   1320
tccagtccag cgcactgtat gaggaccgct acctcctggg cacctctctt gccaggccct   1380
gcatcgcccg caaacaagtg gaaatcgccc agcgggaggg ggccaagtat gtgtcccacg   1440
gcgccacagg aaaggggaac gatcaggtcc ggtttgagct cagctgctac tcactggccc   1500
cccagataaa ggtcattgct ccctggagga tgcctgaatt ctacaaccgg ttcaagggcc   1560
gcaatgacct gatggagtac gcaaagcaac acgggattcc catcccggtc actcccaaga   1620
acccgtggag catggatgag aacctcatgc acatcagcta cgaggctgga atcctggaga   1680
accccaagaa ccaagcgcct ccaggtctct acacgaagac ccaggaccca gccaaagccc   1740
ccaacacccc tgacattctc gagatcgagt tcaaaaaagg ggtccctgtg aaggtgacca   1800
acgtcaagga tggcaccacc caccagacct ccttggagct cttcatgtac ctgaacgaag   1860
tcgcgggcaa gcatggcgtg ggccgtattg acatcgtgga gaaccgcttc attggaatga   1920
agtcccgagg tatctacgag accccagcag gcaccatcct ttaccacgct catttagaca   1980
tcgaggcctt caccatggac cgggaagtgc gcaaaatcaa acaaggcctg ggcttgaaat   2040
ttgctgagct ggtgtatacc ggtttctggc acagccctga gtgtgaattt gtccgccact   2100
gcatcgccaa gtcccaggag cgagtggaag ggaaagtgca ggtgtccgtc ctcaagggcc   2160
aggtgtacat cctcggccgg gagtccccac tgtctctcta caatgaggag ctggtgagca   2220
tgaacgtgca gggtgattat gagccaactg atgccaccgg gttcatcaac atcaattccc   2280
tcaggctgaa ggaatatcat cgtctccaga gcaaggtcac tgccaaatga taagcatgcg   2340
gatctgcctc gactgtgcct tctagttgcc agccatctgt tgtttgcccc tcccccgtgc   2400
cttccttgac cctggaaggt gccactccca ctgtcctttc ctaataaaat gaggaaattg   2460
catcgcattg tctgagtagg tgtcattcta ttctgggggg tggggtgggg caggacagca   2520
agggggagga ttgggaagac aatagcaggc atgctgggga ctcgagttaa gggcgaattc   2580
ccgattagga tcttcctaga gcatggctac gtagataagt agcatggcgg gttaatcatt   2640
aactacaagg aacccctagt gatggagttg gccactccct ctctgcgcgc tcgctcgctc   2700
actgaggccg ggcgaccaaa ggtcgcccga cgcccgggct ttgcccgggc ggcctcagtg   2760
agcgagcgag cgcgcagcct taattaacct aattcactgg ccgtcgtttt acaacgtcgt   2820
gactgggaaa accctggcgt tacccaactt aatcgccttg cagcacatcc ccctttcgcc   2880
agctggcgta atagcgaaga ggcccgcacc gatcgccctt cccaacagtt gcgcagcctg   2940
aatggcgaat gggacgcgcc ctgtagcggc gcattaagcg cggcgggtgt ggtggttacg   3000
```

-continued

```
cgcagcgtga ccgctacact tgccagcgcc ctagcgcccg ctcctttcgc tttcttccct   3060
tcctttctcg ccacgttcgc cggctttccc cgtcaagctc taaatcgggg gctcccttta   3120
gggttccgat ttagtgcttt acggcacctc gaccccaaaa aacttgatta gggtgatggt   3180
tcacgtagtg ggccatcgcc ctgatagacg gtttttcgcc ctttgacgtt ggagtccacg   3240
ttctttaata gtggactctt gttccaaact ggaacaacac tcaaccctat ctcggtctat   3300
tcttttgatt tataagggat tttgccgatt tcggcctatt ggttaaaaaa tgagctgatt   3360
taacaaaaat ttaacgcgaa ttttaacaaa atattaacgc ttacaattta ggtggcactt   3420
ttcggggaaa tgtgcgcgga acccctattt gtttattttt ctaaatacat tcaaatatgt   3480
atccgctcat gagacaataa ccctgataaa tgcttcaata atattgaaaa aggaagagta   3540
tgagtattca acatttccgt gtcgccctta ttcccttttt tgcggcattt tgccttcctg   3600
tttttgctca cccagaaacg ctggtgaaag taaaagatgc tgaagatcag ttgggtgcac   3660
gagtgggtta catcgaactg gatctcaaca gcggtaagat ccttgagagt tttcgccccg   3720
aagaacgttt tccaatgatg agcactttta aagttctgct atgtggcgcg gtattatccc   3780
gtattgacgc cgggcaagag caactcggtc gccgcataca ctattctcag aatgacttgg   3840
ttgagtactc accagtcaca gaaaagcatc ttacggatgg catgacagta agagaattat   3900
gcagtgctgc cataaccatg agtgataaca ctgcggccaa cttacttctg acaacgatcg   3960
gaggaccgaa ggagctaacc gcttttttgc acaacatggg ggatcatgta actcgccttg   4020
atcgttggga accggagctg aatgaagcca taccaaacga cgagcgtgac accacgatgc   4080
ctgtagcaat ggcaacaacg ttgcgcaaac tattaactgg cgaactactt actctagctt   4140
cccggcaaca attaatagac tggatggagg cggataaagt tgcaggacca cttctgcgct   4200
cggcccttcc ggctggctgg tttattgctg ataaatctgg agccggtgag cgtgggtctc   4260
gcggtatcat tgcagcactg gggccagatg gtaagccctc ccgtatcgta gttatctaca   4320
cgacggggag tcaggcaact atggatgaac gaaatagaca gatcgctgag ataggtgcct   4380
cactgattaa gcattggtaa ctgtcagacc aagtttactc atatatactt tagattgatt   4440
taaaacttca tttttaattt aaaaggatct aggtgaagat cctttttgat aatctcatga   4500
ccaaaatccc ttaacgtgag ttttcgttcc actgagcgtc agaccccgta gaaaagatca   4560
aaggatcttc ttgagatcct ttttttctgc gcgtaatctg ctgcttgcaa acaaaaaaac   4620
caccgctacc agcggtggtt tgtttgccgg atcaagagct accaactctt tttccgaagg   4680
taactggctt cagcagagcg cagataccaa atactgttct tctagtgtag ccgtagttag   4740
gccaccactt caagaactct gtagcaccgc ctacatacct cgctctgcta atcctgttac   4800
cagtggctgc tgccagtggc gataagtcgt gtcttaccgg gttggactca agacgatagt   4860
taccggataa ggcgcagcgg tcgggctgaa cggggggttc gtgcacacag cccagcttgg   4920
agcgaacgac ctacaccgaa ctgagatacc tacagcgtga gctatgagaa agcgccacgc   4980
ttcccgaagg gagaaaggcg gacaggtatc cggtaagcgg cagggtcgga acaggagagc   5040
gcacgaggga gcttccaggg ggaaacgcct ggtatcttta tagtcctgtc gggtttcgcc   5100
acctctgact tgagcgtcga tttttgtgat gctcgtcagg ggggcggagc ctatggaaaa   5160
acgccagcaa cgcggccttt ttacggttcc tggccttttg ctggcctttt gctcacatgt   5220
tctttcctgc gttatcccct gattctgtgg ataaccgtat taccgccttt gagtgagctg   5280
ataccgctcg ccgcagccga acgaccgagc gcagcgagtc agtgagcgag gaagcggaag   5340
```

agcgcccaat acgcaaaccg cctctccccg cgcgttggcc gattcattaa tgcagctggc 5400
acgacaggtt tcccgactgg aaagcgggca gtgagcgcaa cgcaattaat gtgagttagc 5460
tcactcatta ggcaccccag gctttacact ttatgcttcc ggctcgtatg ttgtgtggaa 5520
ttgtgagcgg ataacaattt cacacaggaa acagctatga ccatgattac gccagattta 5580
attaagg 5587

<210> SEQ ID NO 28
<211> LENGTH: 6026
<212> TYPE: DNA
<213> ORGANISM: Artificial Sequence
<220> FEATURE:
<223> OTHER INFORMATION: constructed sequence

<400> SEQUENCE: 28
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaaggctca gaggcacaca ggagtttctg ggctcaccct 240 gccccccttcc aacccctcag ttcccatcct ccagcagctg tttgtgtgct gcctctgaag 300
tccacactga acaaacttca gcctactcat gtccctaaaa tgggcaaaca ttgcaagcag 360
caaacagcaa acacacagcc ctccctgcct gctgaccttg gagctggggc agaggtcaga 420
gacctctctg ggcccatgcc acctccaaca tccactcgac cccttggaat ttcggtggag 480
aggagcagag gttgtcctgg cgtggtttag gtagtgtgag agggcgcgcc gatcttgcta 540
ccagtggaac agccactaag gattctgcag tgagagcaga gggccagcta agtggtactc 600
tcccagagac tgtctgactc acgccacccc ctccaccttg gacacaggac gctgtggttt 660
ctgagccagg tacaatgact cctttcggta agtgcagtgg aagctgtaca ctgcccaggc 720
aaagcgtccg ggcagcgtag gcgggcgact cagatcccag ccagtggact tagcccctgt 780
ttgctcctcc gataactggg gtgaccttgg ttaatattca ccagcagcct cccccgttgc 840
ccctctggat ccactgctta aatacggacg aggacagggc cctgtctcct cagcttcagg 900
caccaccact gacctgggac agtagatcta gcttacttgt ggtaccgagc tcggatcctg 960
agaacttcag ggtgagtcta tgggaccctt gatgttttct ttccccttct tttctatggt 1020
taagttcatg tcataggaag gggagaagta acagggtaca catattgacc aaatcagggt 1080
aattttgcat ttgtaatttt aaaaaatgct ttcttctttt aatatacttt tttgtttatc 1140
ttatttctaa tactttccct aatctctttc tttcagggca ataatgatac aatgtatcat 1200
gcctctttgc accattctaa agaataacag tgataatttc tgggttaagg caatagcaat 1260
atttctgcat ataaatattt ctgcatataa attgtaactg atgtaagagg tttcatattg 1320
ctaatagcag ctacaatcca gctaccattc tgcttttatt ttatggttgg gataaggctg 1380
gattattctg agtccaagct aggccctttt gctaatcatg ttcatacctc ttatcttcct 1440
cccacagctc ctgggcaacg tgctggtctg tgtgctggcc catcactttg gcaaagaatt 1500
gatctcgagt aactgaaggc ggccgccacc atgtccagca aaggctccgt ggttctggcc 1560
tacagtggcg gcctggacac ctcgtgcatc ctcgtgtggc tgaaggaaca aggctatgac 1620
gtcattgcct atctggccaa cattggccag aaggaagact tcgaggaagc caggaagaag 1680
gcactgaagc ttggggccaa aaaggtgttc attgaggatg tcagcaggga gtttgtggag 1740
gagttcatct ggccggccat ccagtccagc gcactgtatg aggaccgcta cctcctgggc 1800
acctctcttg ccaggccctg catcgcccgc aaacaagtgg aaatcgccca gcgggagggg 1860
gccaagtatg tgtcccacgg cgccacagga aaggggaacg atcaggtccg gtttgagctc 1920
agctgctact cactggcccc ccagataaag gtcattgctc cctggaggat gcctgaattc 1980
tacaaccggt tcaagggccg caatgacctg atggagtacg caaagcaaca cgggattccc 2040
atcccggtca ctcccaagaa cccgtggagc atggatgaga acctcatgca catcagctac 2100
gaggctggaa tcctggagaa ccccaagaac caagcgcctc caggtctcta cacgaagacc 2160
caggacccag ccaaagcccc caacacccct gacattctcg agatcgagtt caaaaaaggg 2220
gtccctgtga aggtgaccaa cgtcaaggat ggcaccaccc accagacctc cttggagctc 2280
ttcatgtacc tgaacgaagt cgcgggcaag catggcgtgg gccgtattga catcgtggag 2340
aaccgcttca ttggaatgaa gtcccgaggt atctacgaga ccccagcagg caccatcctt 2400
taccacgctc atttagacat cgaggccttc accatggacc gggaagtgcg caaaatcaaa 2460
caaggcctgg gcttgaaatt tgctgagctg gtgtataccg gtttctggca cagccctgag 2520
tgtgaatttg tccgccactg catcgccaag tcccaggagc gagtggaagg gaaagtgcag 2580
gtgtccgtcc tcaagggcca ggtgtacatc ctcggccggg agtccccact gtctctctac 2640
aatgaggagc tggtgagcat gaacgtgcag ggtgattatg agccaactga tgccaccggg 2700
ttcatcaaca tcaattccct caggctgaag gaatatcatc gtctccagag caaggtcact 2760
gccaaatgat aagcatgcgg atctgcctcg actgtgcctt ctagttgcca gccatctgtt 2820
gtttgcccct cccccgtgcc ttccttgacc ctggaaggtg ccactcccac tgtcctttcc 2880
taataaaatg aggaaattgc atcgcattgt ctgagtaggt gtcattctat tctggggggt 2940
ggggtggggc aggacagcaa gggggaggat tgggaagaca atagcaggca tgctggggac 3000
tcgagttaag ggcgaattcc cgataaggat cttcctagag catggctacg tagataagta 3060
gcatggcggg ttaatcatta actacaagga acccctagtg atggagttgg ccactccctc 3120
tctgcgcgct cgctcgctca ctgaggccgg gcgaccaaag gtcgcccgac gcccgggctt 3180
tgcccgggcg gcctcagtga gcgagcgagc gcgcagcctt aattaaccta attcactggc 3240
cgtcgtttta caacgtcgtg actgggaaaa ccctggcgtt acccaactta atcgccttgc 3300
agcacatccc cctttcgcca gctggcgtaa tagcgaagag gcccgcaccg atcgcccttc 3360
ccaacagttg cgcagcctga atggcgaatg ggacgcgccc tgtagcggcg cattaagcgc 3420
ggcgggtgtg gtggttacgc gcagcgtgac cgctacactt gccagcgccc tagcgcccgc 3480
tcctttcgct ttcttccctt cctttctcgc cacgttcgcc ggctttcccc gtcaagctct 3540
aaatcggggg ctccctttag ggttccgatt tagtgcttta cggcacctcg accccaaaaa 3600
acttgattag ggtgatggtt cacgtagtgg gccatcgccc tgatagacgg tttttcgccc 3660
tttgacgttg gagtccacgt tctttaatag tggactcttg ttccaaactg gaacaacact 3720
caaccctatc tcggtctatt cttttgattt ataagggatt ttgccgattt cggcctattg 3780
gttaaaaaat gagctgattt aacaaaaatt taacgcgaat tttaacaaaa tattaacgct 3840
tacaatttag gtggcacttt tcggggaaat gtgcgcggaa cccctatttg tttatttttc 3900
taaatacatt caaatatgta tccgctcatg agacaataac cctgataaat gcttcaataa 3960
tattgaaaaa ggaagagtat gagtattcaa catttccgtg tcgcccttat tccctttttt 4020
gcggcatttt gccttcctgt ttttgctcac ccagaaacgc tggtgaaagt aaaagatgct 4080
gaagatcagt tgggtgcacg agtgggttac atcgaactgg atctcaacag cggtaagatc 4140
cttgagagtt ttcgccccga agaacgtttt ccaatgatga gcacttttaa agttctgcta 4200
tgtggcgcgg tattatcccg tattgacgcc gggcaagagc aactcggtcg ccgcatacac 4260
tattctcaga atgacttggt tgagtactca ccagtcacag aaaagcatct tacggatggc 4320
atgacagtaa gagaattatg cagtgctgcc ataaccatga gtgataacac tgcggccaac 4380
ttacttctga caacgatcgg aggaccgaag gagctaaccg cttttttgca caacatgggg 4440
gatcatgtaa ctcgccttga tcgttgggaa ccggagctga atgaagccat accaaacgac 4500
gagcgtgaca ccacgatgcc tgtagcaatg gcaacaacgt tgcgcaaact attaactggc 4560
gaactactta ctctagcttc ccggcaacaa ttaatagact ggatggaggc ggataaagtt 4620
gcaggaccac ttctgcgctc ggcccttccg gctggctggt ttattgctga taaatctgga 4680
gccggtgagc gtgggtctcg cggtatcatt gcagcactgg ggccagatgg taagccctcc 4740
cgtatcgtag ttatctacac gacggggagt caggcaacta tggatgaacg aaatagacag 4800
atcgctgaga taggtgcctc actgattaag cattggtaac tgtcagacca agtttactca 4860
tatatacttt agattgattt aaaacttcat ttttaattta aaaggatcta ggtgaagatc 4920
ctttttgata atctcatgac caaaatccct taacgtgagt tttcgttcca ctgagcgtca 4980
gaccccgtag aaaagatcaa aggatcttct tgagatcctt tttttctgcg cgtaatctgc 5040
tgcttgcaaa caaaaaaacc accgctacca gcggtggttt gtttgccgga tcaagagcta 5100
ccaactcttt ttccgaaggt aactggcttc agcagagcgc agataccaaa tactgttctt 5160
ctagtgtagc cgtagttagg ccaccacttc aagaactctg tagcaccgcc tacatacctc 5220
gctctgctaa tcctgttacc agtggctgct gccagtggcg ataagtcgtg tcttaccggg 5280
ttggactcaa gacgatagtt accggataag gcgcagcggt cgggctgaac ggggggttcg 5340
tgcacacagc ccagcttgga gcgaacgacc tacaccgaac tgagatacct acagcgtgag 5400
ctatgagaaa gcgccacgct tcccgaaggg agaaaggcgg acaggtatcc ggtaagcggc 5460
agggtcggaa caggagagcg cacgagggag cttccagggg gaaacgcctg gtatctttat 5520
agtcctgtcg ggtttcgcca cctctgactt gagcgtcgat ttttgtgatg ctcgtcaggg 5580
gggcggagcc tatggaaaaa cgccagcaac gcggcctttt tacggttcct ggccttttgc 5640
tggccttttg ctcacatgtt ctttcctgcg ttatcccctg attctgtgga taaccgtatt 5700
accgcctttg agtgagctga taccgctcgc cgcagccgaa cgaccgagcg cagcgagtca 5760
gtgagcgagg aagcggaaga gcgcccaata cgcaaaccgc ctctccccgc gcgttggccg 5820
attcattaat gcagctggca cgacaggttt cccgactgga aagcgggcag tgagcgcaac 5880
gcaattaatg tgagttagct cactcattag gcaccccagg ctttacactt tatgcttccg 5940
gctcgtatgt tgtgtggaat tgtgagcgga taacaatttc acacaggaaa cagctatgac 6000
catgattacg ccagatttaa ttaagg 6026

<210> SEQ ID NO 29
<211> LENGTH: 5876
<212> TYPE: DNA
<213> ORGANISM: Artificial Sequence
<220> FEATURE:
<223> OTHER INFORMATION: constructed sequence

<400> SEQUENCE: 29
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180

```
aggaagatcg gaattcgccc ttaagctagc cgctgacaag gctcagaggc acacaggagt    240
ttctgggctc accctgcccc cttccaaccc ctcagttccc atcctccagc agctgtttgt    300
gtgctgcctc tgaagtccac actgaacaaa cttcagccta ctcatgtccc taaaatgggc    360
aaacattgca agcagcaaac agcaaacaca cagccctccc tgcctgctga ccttggagct    420
ggggcagagg tcagagacct ctctgggccc atgccacctc caacatccac tcgacccctt    480
ggaatttcgg tggagaggag cagaggttgt cctggcgtgg tttaggtagt gtgagaggga    540
gatccggcgc gcctggacac aggacgctgt ggtttctgag ccaggggggcg actcagatcc    600
cagccagtgg acttagcccc tgtttgctcc tccgataact ggggtgacct tggttaatat    660
tcaccagcag cctcccccgt tgcccctctg gatccactgc ttaaatacgg acgaggacag    720
ggccctgtct cctcagcttc aggcaccacc actgacctgg gacagtgaat agcgagatct    780
agcttacttg tggtaccagc tcggatcctg agaacttcag ggtgagtcta tgggaccctt    840
gatgttttct ttccccttct tttctatggt taagttcatg tcataggaag gggagaagta    900
acagggtaca catattgacc aaatcagggt aattttgcat ttgtaatttt aaaaaatgct    960
ttcttctttt aatatacttt tttgtttatc ttatttctaa tactttccct aatctctttc   1020
tttcagggca ataatgatac aatgtatcat gcctctttgc accattctaa agaataacag   1080
tgataatttc tgggttaagg caatagcaat atttctgcat ataaatattt ctgcatataa   1140
attgtaactg atgtaagagg tttcatattg ctaatagcag ctacaatcca gctaccattc   1200
tgcttttatt ttatggttgg gataaggctg gattattctg agtccaagct aggccctttt   1260
gctaatcatg ttcatacctc ttatcttcct cccacagctc ctgggcaacg tgctggtctg   1320
tgtgctggcc catcactttg gcaaagaatt gatctcgagt aactgaaggc ggccgccacc   1380
atgagcagca agggctctgt ggtgctggcc tactctggcg gcctggacac cagctgtatc   1440
ctcgtgtggc tgaaagaaca gggctacgac gtgatcgcct acctggccaa catcggccag   1500
aaagaggact tcgaggaagc ccggaagaag gccctgaagc tgggcgccaa gaaggtgttc   1560
atcgaggacg tgtcccgcga gttcgtggaa gagttcatct ggcccgccat ccagagcagc   1620
gccctgtacg aggacagata cctgctgggc accagcctgg ccagaccctg tatcgcccgg   1680
aaacaggtgg aaatcgccca gcgcgagggc gccaaatacg tgtctcacgg cgccaccggc   1740
aagggcaacg accaggtgcg ctttgagctg agctgctact ccctggcccc ccagatcaaa   1800
gtgatcgccc cttggcggat gcccgagttc tacaaccggt tcaagggccg gaacgacctg   1860
atggaatacg ccaagcagca cggcatcccc atccccgtga cccccaagaa cccttggagc   1920
atggacgaga acctgatgca catcagctac gaggccggca tcctggaaaa ccccaagaat   1980
caggcccctc ccggcctgta cacaaagacc caggaccctg ccaaggcccc caacaccccc   2040
gacattctgg aaatcgagtt caagaaaggc gtgcccgtga aagtgaccaa cgtgaaggac   2100
ggcaccaccc accagacctc cctggaactg ttcatgtacc tgaacgaggt ggccggcaag   2160
cacggcgtgg gcagaatcga catcgtggaa aacagattca tcggcatgaa gtcccggggc   2220
atctacgaga caccagccgg caccatcctg taccacgccc acctggatat cgaggccttc   2280
accatggacc gggaagtgcg gaagatcaag cagggcctgg gcctgaagtt cgccgagctg   2340
gtgtacacag gcttttggca cagccccgag tgcgagtttg tgcggcactg cattgccaag   2400
agccaggaac gggtggaagg caaggtgcag gtgtccgtgc tgaagggcca ggtgtacatt   2460
ctgggcagag agagcccccct gagcctgtac aacgaggaac tggtgtctat gaacgtgcag   2520
```

-continued

```
ggcgactacg agcccaccga cgccaccggc ttcatcaaca tcaacagcct gagactgaaa   2580
gagtaccacc ggctgcagtc caaagtgacc gccaagtgat aagcatgcgg atctgcctcg   2640
actgtgcctt ctagttgcca gccatctgtt gtttgcccct cccccgtgcc ttccttgacc   2700
ctggaaggtg ccactcccac tgtcctttcc taataaaatg aggaaattgc atcgcattgt   2760
ctgagtaggt gtcattctat tctggggggt ggggtggggc aggacagcaa gggggaggat   2820
tgggaagaca atagcaggca tgctggggac tcgagttaag ggcgaattcc cgataaggat   2880
cttcctagag catggctacg tagataagta gcatggcggg ttaatcatta actacaagga   2940
acccctagtg atggagttgg ccactccctc tctgcgcgct cgctcgctca ctgaggccgg   3000
gcgaccaaag gtcgcccgac gcccgggctt tgcccgggcg gcctcagtga gcgagcgagc   3060
gcgcagcctt aattaaccta attcactggc cgtcgtttta caacgtcgtg actgggaaaa   3120
ccctggcgtt acccaactta atcgccttgc agcacatccc cctttcgcca gctggcgtaa   3180
tagcgaagag gcccgcaccg atcgcccttc ccaacagttg cgcagcctga atggcgaatg   3240
ggacgcgccc tgtagcggcg cattaagcgc ggcgggtgtg gtggttacgc gcagcgtgac   3300
cgctacactt gccagcgccc tagcgcccgc tcctttcgct ttcttccctt cctttctcgc   3360
cacgttcgcc ggctttcccc gtcaagctct aaatcggggg ctccctttag ggttccgatt   3420
tagtgcttta cggcacctcg accccaaaaa acttgattag ggtgatggtt cacgtagtgg   3480
gccatcgccc tgatagacgg tttttcgccc tttgacgttg gagtccacgt tctttaatag   3540
tggactcttg ttccaaactg gaacaacact caaccctatc tcggtctatt cttttgattt   3600
ataagggatt ttgccgattt cggcctattg gttaaaaaat gagctgattt aacaaaaatt   3660
taacgcgaat tttaacaaaa tattaacgct tacaatttag gtggcacttt tcggggaaat   3720
gtgcgcggaa cccctatttg tttatttttc taaatacatt caaatatgta tccgctcatg   3780
agacaataac cctgataaat gcttcaataa tattgaaaaa ggaagagtat gagtattcaa   3840
catttccgtg tcgcccttat tccctttttt gcggcatttt gccttcctgt ttttgctcac   3900
ccagaaacgc tggtgaaagt aaaagatgct gaagatcagt tgggtgcacg agtgggttac   3960
atcgaactgg atctcaacag cggtaagatc cttgagagtt ttcgccccga agaacgtttt   4020
ccaatgatga gcacttttaa agttctgcta tgtggcgcgg tattatcccg tattgacgcc   4080
gggcaagagc aactcggtcg ccgcatacac tattctcaga atgacttggt tgagtactca   4140
ccagtcacag aaaagcatct tacggatggc atgacagtaa gagaattatg cagtgctgcc   4200
ataaccatga gtgataacac tgcggccaac ttacttctga caacgatcgg aggaccgaag   4260
gagctaaccg cttttttgca caacatgggg gatcatgtaa ctcgccttga tcgttgggaa   4320
ccggagctga atgaagccat accaaacgac gagcgtgaca ccacgatgcc tgtagcaatg   4380
gcaacaacgt tgcgcaaact attaactggc gaactactta ctctagcttc ccggcaacaa   4440
ttaatagact ggatggaggc ggataaagtt gcaggaccac ttctgcgctc ggcccttccg   4500
gctggctggt ttattgctga taaatctgga gccggtgagc gtgggtctcg cggtatcatt   4560
gcagcactgg ggccagatgg taagccctcc cgtatcgtag ttatctacac gacggggagt   4620
caggcaacta tggatgaacg aaatagacag atcgctgaga taggtgcctc actgattaag   4680
cattggtaac tgtcagacca agtttactca tatatacttt agattgattt aaaacttcat   4740
ttttaattta aaaggatcta ggtgaagatc ctttttgata atctcatgac caaaatccct   4800
taacgtgagt tttcgttcca ctgagcgtca gaccccgtag aaaagatcaa aggatcttct   4860
tgagatcctt tttttctgcg cgtaatctgc tgcttgcaaa caaaaaaacc accgctacca   4920
```

gcggtggttt gtttgccgga tcaagagcta ccaactcttt ttccgaaggt aactggcttc 4980
agcagagcgc agataccaaa tactgttctt ctagtgtagc cgtagttagg ccaccacttc 5040
aagaactctg tagcaccgcc tacatacctc gctctgctaa tcctgttacc agtggctgct 5100
gccagtggcg ataagtcgtg tcttaccggg ttggactcaa gacgatagtt accggataag 5160
gcgcagcggt cgggctgaac ggggggttcg tgcacacagc ccagcttgga gcgaacgacc 5220
tacaccgaac tgagatacct acagcgtgag ctatgagaaa gcgccacgct tcccgaaggg 5280
agaaaggcgg acaggtatcc ggtaagcggc agggtcggaa caggagagcg cacgagggag 5340
cttccagggg gaaacgcctg gtatctttat agtcctgtcg ggtttcgcca cctctgactt 5400
gagcgtcgat ttttgtgatg ctcgtcaggg gggcggagcc tatggaaaaa cgccagcaac 5460
gcggcctttt tacggttcct ggccttttgc tggccttttg ctcacatgtt ctttcctgcg 5520
ttatcccctg attctgtgga taaccgtatt accgcctttg agtgagctga taccgctcgc 5580
cgcagccgaa cgaccgagcg cagcgagtca gtgagcgagg aagcggaaga gcgcccaata 5640
cgcaaaccgc ctctccccgc gcgttggccg attcattaat gcagctggca cgacaggttt 5700
cccgactgga aagcgggcag tgagcgcaac gcaattaatg tgagttagct cactcattag 5760
gcaccccagg ctttacactt tatgcttccg gctcgtatgt tgtgtggaat tgtgagcgga 5820
taacaatttc acacaggaaa cagctatgac catgattacg ccagatttaa ttaagg 5876

<210> SEQ ID NO 30
<211> LENGTH: 4893
<212> TYPE: DNA
<213> ORGANISM: Artificial Sequence
<220> FEATURE:
<223> OTHER INFORMATION: constructed sequence

<400> SEQUENCE: 30
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctactta agtgtttgct 180
gcttgcaatg tttgcccatt ttaggggaat tctggacaca ggacgctgtg gtttctgagc 240
cagggggcga ctcagatccc agccagtgga cttagcccct gtttgctcct ccgataactg 300
gggtgacctt ggttaatatt caccagcagc ctcccccgtt gcccctctgg atccactgct 360
taaatacgga cgaggacagg gccctgtctc ctcagcttca ggcaccacca ctgacctggg 420
acagtgaata gcggccgcca ccatgagcag caagggctct gtggtgctgg cctactctgg 480
cggcctggac accagctgta tcctcgtgtg gctgaaagaa cagggctacg acgtgatcgc 540
ctacctggcc aacatcggcc agaaagagga cttcgaggaa gcccggaaga aggccctgaa 600
gctgggcgcc aagaaggtgt tcatcgagga cgtgtcccgc gagttcgtgg aagagttcat 660
ctggcccgcc atccagagca gcgccctgta cgaggacaga tacctgctgg gcaccagcct 720
ggccagaccc tgtatcgccc ggaaacaggt ggaaatcgcc cagcgcgagg gcgccaaata 780
cgtgtctcac ggcgccaccg gcaagggcaa cgaccaggtg cgctttgagc tgagctgcta 840
ctccctggcc ccccagatca aagtgatcgc cccttggcgg atgcccgagt tctacaaccg 900
gttcaagggc cggaacgacc tgatggaata cgccaagcag cacggcatcc ccatccccgt 960
gacccccaag aacccttgga gcatggacga gaacctgatg cacatcagct acgaggccgg 1020
catcctggaa aaccccaaga atcaggcccc tcccggcctg tacacaaaga cccaggaccc 1080

-continued

```
tgccaaggcc cccaacaccc ccgacattct ggaaatcgag ttcaagaaag gcgtgcccgt   1140
gaaagtgacc aacgtgaagg acggcaccac ccaccagacc tccctggaac tgttcatgta   1200
cctgaacgag gtggccggca agcacggcgt gggcagaatc gacatcgtgg aaaacagatt   1260
catcggcatg aagtcccggg gcatctacga gacaccagcc ggcaccatcc tgtaccacgc   1320
ccacctggat atcgaggcct tcaccatgga ccgggaagtg cggaagatca agcagggcct   1380
gggcctgaag ttcgccgagc tggtgtacac aggcttttgg cacagccccg agtgcgagtt   1440
tgtgcggcac tgcattgcca agagccagga acgggtggaa ggcaaggtgc aggtgtccgt   1500
gctgaagggc caggtgtaca ttctgggcag agagagcccc ctgagcctgt acaacgagga   1560
actggtgtct atgaacgtgc agggcgacta cgagcccacc gacgccaccg gcttcatcaa   1620
catcaacagc ctgagactga aagagtacca ccggctgcag tccaaagtga ccgccaagtg   1680
ataagcatgc ggatctgcct cgactgtgcc ttctagttgc cagccatctg ttgtttgccc   1740
ctcccccgtg ccttccttga ccctggaagg tgccactccc actgtccttt cctaataaaa   1800
tgaggaaatt gcatcgcatt gtctgagtag gtgtcattct attctggggg gtggggtggg   1860
gcaggacagc aagggggagg attgggaaga caatagcagg catgctgggg actcgagtag   1920
ataagtagca tggcgggtta atcattaact acaaggaacc cctagtgatg gagttggcca   1980
ctccctctct gcgcgctcgc tcgctcactg aggccgggcg accaaaggtc gcccgacgcc   2040
cgggctttgc ccgggcggcc tcagtgagcg agcgagcgcg cagccttaat taacctaatt   2100
cactggccgt cgttttacaa cgtcgtgact gggaaaaccc tggcgttacc caacttaatc   2160
gccttgcagc acatccccct ttcgccagct ggcgtaatag cgaagaggcc cgcaccgatc   2220
gcccttccca acagttgcgc agcctgaatg gcgaatggga cgcgccctgt agcggcgcat   2280
taagcgcggc gggtgtggtg gttacgcgca gcgtgaccgc tacacttgcc agcgccctag   2340
cgcccgctcc tttcgctttc ttcccttcct ttctcgccac gttcgccggc tttccccgtc   2400
aagctctaaa tcgggggctc cctttagggt tccgatttag tgctttacgg cacctcgacc   2460
ccaaaaaact tgattagggt gatggttcac gtagtgggcc atcgccctga tagacggttt   2520
ttcgcccttt gacgttggag tccacgttct ttaatagtgg actcttgttc caaactggaa   2580
caacactcaa ccctatctcg gtctattctt ttgatttata agggattttg ccgatttcgg   2640
cctattggtt aaaaaatgag ctgatttaac aaaaatttaa cgcgaatttt aacaaaatat   2700
taacgcttac aatttaggtg gcacttttcg gggaaatgtg cgcggaaccc ctatttgttt   2760
atttttctaa atacattcaa atatgtatcc gctcatgaga caataaccct gataaatgct   2820
tcaataatat tgaaaaagga agagtatgag tattcaacat ttccgtgtcg cccttattcc   2880
cttttttgcg gcattttgcc ttcctgtttt tgctcaccca gaaacgctgg tgaaagtaaa   2940
agatgctgaa gatcagttgg gtgcacgagt gggttacatc gaactggatc tcaacagcgg   3000
taagatcctt gagagttttc gccccgaaga acgttttcca atgatgagca cttttaaagt   3060
tctgctatgt ggcgcggtat tatcccgtat tgacgccggg caagagcaac tcggtcgccg   3120
catacactat tctcagaatg acttggttga gtactcacca gtcacagaaa agcatcttac   3180
ggatggcatg acagtaagag aattatgcag tgctgccata accatgagtg ataacactgc   3240
ggccaactta cttctgacaa cgatcggagg accgaaggag ctaaccgctt ttttgcacaa   3300
catgggggat catgtaactc gccttgatcg ttgggaaccg gagctgaatg aagccatacc   3360
aaacgacgag cgtgacacca cgatgcctgt agcaatggca acaacgttgc gcaaactatt   3420
aactggcgaa ctacttactc tagcttcccg gcaacaatta atagactgga tggaggcgga   3480
```

taaagttgca ggaccacttc tgcgctcggc ccttccggct ggctggttta ttgctgataa 3540
atctggagcc ggtgagcgtg ggtctcgcgg tatcattgca gcactggggc cagatggtaa 3600
gccctcccgt atcgtagtta tctacacgac ggggagtcag gcaactatgg atgaacgaaa 3660
tagacagatc gctgagatag gtgcctcact gattaagcat tggtaactgt cagaccaagt 3720
ttactcatat atactttaga ttgatttaaa acttcatttt taatttaaaa ggatctaggt 3780
gaagatcctt tttgataatc tcatgaccaa aatcccttaa cgtgagtttt cgttccactg 3840
agcgtcagac cccgtagaaa agatcaaagg atcttcttga gatccttttt ttctgcgcgt 3900
aatctgctgc ttgcaaacaa aaaaaccacc gctaccagcg gtggtttgtt tgccggatca 3960
agagctacca actctttttc cgaaggtaac tggcttcagc agagcgcaga taccaaatac 4020
tgttcttcta gtgtagccgt agttaggcca ccacttcaag aactctgtag caccgcctac 4080
atacctcgct ctgctaatcc tgttaccagt ggctgctgcc agtggcgata agtcgtgtct 4140
taccgggttg gactcaagac gatagttacc ggataaggcg cagcggtcgg gctgaacggg 4200
gggttcgtgc acacagccca gcttggagcg aacgacctac accgaactga gatacctaca 4260
gcgtgagcta tgagaaagcg ccacgcttcc cgaagggaga aaggcggaca ggtatccggt 4320
aagcggcagg gtcggaacag gagagcgcac gagggagctt ccagggggaa acgcctggta 4380
tctttatagt cctgtcgggt ttcgccacct ctgacttgag cgtcgatttt tgtgatgctc 4440
gtcagggggg cggagcctat ggaaaaacgc cagcaacgcg gcctttttac ggttcctggc 4500
cttttgctgg ccttttgctc acatgttctt tcctgcgtta tcccctgatt ctgtggataa 4560
ccgtattacc gcctttgagt gagctgatac cgctcgccgc agccgaacga ccgagcgcag 4620
cgagtcagtg agcgaggaag cggaagagcg cccaatacgc aaaccgcctc tccccgcgcg 4680
ttggccgatt cattaatgca gctggcacga caggtttccc gactggaaag cgggcagtga 4740
gcgcaacgca attaatgtga gttagctcac tcattaggca ccccaggctt tacactttat 4800
gcttccggct cgtatgttgt gtggaattgt gagcggataa caatttcaca caggaaacag 4860
ctatgaccat gattacgcca gatttaatta agg 4893

<210> SEQ ID NO 31
<211> LENGTH: 4931
<212> TYPE: DNA
<213> ORGANISM: Artificial Sequence
<220> FEATURE:
<223> OTHER INFORMATION: constructed sequence

<400> SEQUENCE: 31
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctactta agctacctcg 180
tgatcgcccg gcccctgttc aaacatgtcc taatactctg tctctgcaag ggtcatcagt 240
agttttccat cttactcaac atcctcccag tggaattcat ttcatagaac gaatgttccg 300
atgctctaat ctctctagac aaggttcata tttgtatggg ttacttattc tctctttgtt 360
gactaagtca ataatcagaa tcagcaggtt tgcagtcaga ttggcaggga taagcagcct 420
agctcaggag aagtgagtat aaaagcccca ggctgggagc agccatcagc ggccgccacc 480
atgagcagca agggctctgt ggtgctggcc tactctggcg gcctggacac cagctgtatc 540
ctcgtgtggc tgaaagaaca gggctacgac gtgatcgcct acctggccaa catcggccag 600

-continued

```
aaagaggact tcgaggaagc ccggaagaag gccctgaagc tgggcgccaa gaaggtgttc    660
atcgaggacg tgtcccgcga gttcgtggaa gagttcatct ggcccgccat ccagagcagc    720
gccctgtacg aggacagata cctgctgggc accagcctgg ccagaccctg tatcgcccgg    780
aaacaggtgg aaatcgccca gcgcgagggc gccaaatacg tgtctcacgg cgccaccggc    840
aagggcaacg accaggtgcg ctttgagctg agctgctact ccctggcccc ccagatcaaa    900
gtgatcgccc cttggcggat gcccgagttc tacaaccggt tcaagggccg gaacgacctg    960
atggaatacg ccaagcagca cggcatcccc atccccgtga cccccaagaa ccccttggagc   1020
atggacgaga acctgatgca catcagctac gaggccggca tcctggaaaa ccccaagaat   1080
caggcccctc ccggcctgta cacaaagacc caggaccctg ccaaggcccc caacaccccc   1140
gacattctgg aaatcgagtt caagaaaggc gtgcccgtga aagtgaccaa cgtgaaggac   1200
ggcaccaccc accagacctc cctggaactg ttcatgtacc tgaacgaggt ggccggcaag   1260
cacggcgtgg gcagaatcga catcgtggaa aacagattca tcggcatgaa gtcccggggc   1320
atctacgaga caccagccgg caccatcctg taccacgccc acctggatat cgaggccttc   1380
accatggacc gggaagtgcg gaagatcaag cagggcctgg gcctgaagtt cgccgagctg   1440
gtgtacacag gcttttggca cagccccgag tgcgagtttg tgcggcactg cattgccaag   1500
agccaggaac gggtggaagg caaggtgcag gtgtccgtgc tgaagggcca ggtgtacatt   1560
ctgggcagag agagcccccct gagcctgtac aacgaggaac tggtgtctat gaacgtgcag   1620
ggcgactacg agcccaccga cgccaccggc ttcatcaaca tcaacagcct gagactgaaa   1680
gagtaccacc ggctgcagtc caaagtgacc gccaagtgat aagcatgcgg atctgcctcg   1740
actgtgcctt ctagttgcca gccatctgtt gtttgcccct cccccgtgcc ttccttgacc   1800
ctggaaggtg ccactcccac tgtcctttcc taataaaatg aggaaattgc atcgcattgt   1860
ctgagtaggt gtcattctat tctggggggt ggggtggggc aggacagcaa gggggaggat   1920
tgggaagaca atagcaggca tgctggggac tcgagtagat aagtagcatg gcgggttaat   1980
cattaactac aaggaacccc tagtgatgga gttggccact ccctctctgc gcgctcgctc   2040
gctcactgag gccgggcgac caaaggtcgc ccgacgcccg ggctttgccc gggcggcctc   2100
agtgagcgag cgagcgcgca gccttaatta acctaattca ctggccgtcg ttttacaacg   2160
tcgtgactgg gaaaaccctg gcgttaccca acttaatcgc cttgcagcac atcccccttt   2220
cgccagctgg cgtaatagcg aagaggcccg caccgatcgc ccttcccaac agttgcgcag   2280
cctgaatggc gaatgggacg cgccctgtag cggcgcatta agcgcggcgg gtgtggtggt   2340
tacgcgcagc gtgaccgcta cacttgccag cgccctagcg cccgctcctt tcgctttctt   2400
cccttccttt ctcgccacgt tcgccggctt tccccgtcaa gctctaaatc gggggctccc   2460
tttagggttc cgatttagtg ctttacggca cctcgacccc aaaaaacttg attagggtga   2520
tggttcacgt agtgggccat cgccctgata gacggttttt cgccctttga cgttggagtc   2580
cacgttcttt aatagtggac tcttgttcca aactggaaca acactcaacc ctatctcggt   2640
ctattctttt gatttataag ggattttgcc gatttcggcc tattggttaa aaaatgagct   2700
gatttaacaa aaatttaacg cgaattttaa caaaatatta acgcttacaa tttaggtggc   2760
acttttcggg gaaatgtgcg cggaacccct atttgtttat ttttctaaat acattcaaat   2820
atgtatccgc tcatgagaca ataaccctga taaatgcttc aataatattg aaaaaggaag   2880
agtatgagta ttcaacattt ccgtgtcgcc cttattccct tttttgcggc attttgcctt   2940
cctgtttttg ctcacccaga aacgctggtg aaagtaaaag atgctgaaga tcagttgggt   3000
```

gcacgagtgg gttacatcga actggatctc aacagcggta agatccttga gagttttcgc 3060
cccgaagaac gttttccaat gatgagcact tttaaagttc tgctatgtgg cgcggtatta 3120
tcccgtattg acgccgggca agagcaactc ggtcgccgca tacactattc tcagaatgac 3180
ttggttgagt actcaccagt cacagaaaag catcttacgg atggcatgac agtaagagaa 3240
ttatgcagtg ctgccataac catgagtgat aacactgcgg ccaacttact tctgacaacg 3300
atcggaggac cgaaggagct aaccgctttt ttgcacaaca tgggggatca tgtaactcgc 3360
cttgatcgtt gggaaccgga gctgaatgaa gccataccaa acgacgagcg tgacaccacg 3420
atgcctgtag caatggcaac aacgttgcgc aaactattaa ctggcgaact acttactcta 3480
gcttcccggc aacaattaat agactggatg gaggcggata aagttgcagg accacttctg 3540
cgctcggccc ttccggctgg ctggtttatt gctgataaat ctggagccgg tgagcgtggg 3600
tctcgcggta tcattgcagc actggggcca gatggtaagc cctcccgtat cgtagttatc 3660
tacacgacgg ggagtcaggc aactatggat gaacgaaata gacagatcgc tgagataggt 3720
gcctcactga ttaagcattg gtaactgtca gaccaagttt actcatatat actttagatt 3780
gatttaaaac ttcattttta atttaaaagg atctaggtga agatcctttt tgataatctc 3840
atgaccaaaa tcccttaacg tgagttttcg ttccactgag cgtcagaccc cgtagaaaag 3900
atcaaaggat cttcttgaga tccttttttt ctgcgcgtaa tctgctgctt gcaaacaaaa 3960
aaaccaccgc taccagcggt ggtttgtttg ccggatcaag agctaccaac tctttttccg 4020
aaggtaactg gcttcagcag agcgcagata ccaaatactg ttcttctagt gtagccgtag 4080
ttaggccacc acttcaagaa ctctgtagca ccgcctacat acctcgctct gctaatcctg 4140
ttaccagtgg ctgctgccag tggcgataag tcgtgtctta ccgggttgga ctcaagacga 4200
tagttaccgg ataaggcgca gcggtcgggc tgaacggggg gttcgtgcac acagcccagc 4260
ttggagcgaa cgacctacac cgaactgaga tacctacagc gtgagctatg agaaagcgcc 4320
acgcttcccg aagggagaaa ggcggacagg tatccggtaa gcggcagggt cggaacagga 4380
gagcgcacga gggagcttcc agggggaaac gcctggtatc tttatagtcc tgtcgggttt 4440
cgccacctct gacttgagcg tcgatttttg tgatgctcgt caggggggcg gagcctatgg 4500
aaaaacgcca gcaacgcggc ctttttacgg ttcctggcct tttgctggcc ttttgctcac 4560
atgttctttc ctgcgttatc ccctgattct gtggataacc gtattaccgc ctttgagtga 4620
gctgataccg ctcgccgcag ccgaacgacc gagcgcagcg agtcagtgag cgaggaagcg 4680
gaagagcgcc caatacgcaa accgcctctc cccgcgcgtt ggccgattca ttaatgcagc 4740
tggcacgaca ggtttcccga ctggaaagcg ggcagtgagc gcaacgcaat taatgtgagt 4800
tagctcactc attaggcacc ccaggcttta cactttatgc ttccggctcg tatgttgtgt 4860
ggaattgtga gcggataaca atttcacaca ggaaacagct atgaccatga ttacgccaga 4920
tttaattaag g 4931

<210> SEQ ID NO 32
<211> LENGTH: 6031
<212> TYPE: DNA
<213> ORGANISM: Artificial Sequence
<220> FEATURE:
<223> OTHER INFORMATION: constructed sequence

<400> SEQUENCE: 32
ctgcgcgctc gctcgctcac tgaggccgcc cgggcaaagc ccgggcgtcg ggcgaccttt 60

-continued

```
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagctagg agttaatttt taaaaagcag tcaaaagtcc    240
aagtgccctt gcgagcattt actctctctg tttgctctgg ttaataatct caggagcaca    300
aacattcctt actagttcta ggagttaatt tttaaaaagc agtcaaaagt ccaagtgccc    360
ttgcgagcat ttactctctc tgtttgctct ggttaataat ctcaggagca caaacattcc    420
ttactagttc tagagcggcc gccagtgtgc tggaattcgg ctttttttagg gctggaagct    480
acctttgaca tcatttcctc tgcgaatgca tgtataattt ctacagaacc tattagaaag    540
gatcacccag cctctgcttt tgtacaactt tcccttaaaa aactgccaat cccactgctg    600
tttggcccaa tagtgagaac tttttcctgc tgcctcttgg tgcttttgcc tatggcccct    660
attctgcctg ctgaagacac tcttgccagc atggacttaa acccctccag ctctgacaat    720
cctctttctc ttttgtttta catgaagggt ctggcagcca aagcaatcac tcaaagttca    780
aaccttatca ttttttgctt tgttcctctt ggccttggtt ttgtacatca gctttgaaaa    840
taccatccca gggttaatgc tggggttaat ttataactga gagtgctcta gttctgcaat    900
acaggacatg ctataaaaat ggaaagatgt tgctttctga gagatcagct tacttgtggt    960
accgagctcg gatcctgaga acttcagggt gagtctatgg gacccttgat gttttctttc   1020
cccttctttt ctatggttaa gttcatgtca taggaagggg agaagtaaca gggtacacat   1080
attgaccaaa tcagggtaat tttgcatttg taattttaaa aaatgctttc ttcttttaat   1140
atactttttt gtttatctta tttctaatac tttccctaat ctctttcttt cagggcaata   1200
atgatacaat gtatcatgcc tctttgcacc attctaaaga ataacagtga taatttctgg   1260
gttaaggcaa tagcaatatt tctgcatata aatatttctg catataaatt gtaactgatg   1320
taagaggttt catattgcta atagcagcta caatccagct accattctgc ttttatttta   1380
tggttgggat aaggctggat tattctgagt ccaagctagg cccttttgct aatcatgttc   1440
atacctctta tcttcctccc acagctcctg ggcaacgtgc tggtctgtgt gctggcccat   1500
cactttggca aagaattgat ctcgaggccg ccaccatgtc cagcaaaggc tccgtggttc   1560
tggcctacag tggcggcctg gacacctcgt gcatcctcgt gtggctgaag gaacaaggct   1620
atgacgtcat tgcctatctg gccaacattg gccagaagga agacttcgag gaagccagga   1680
agaaggcact gaagcttggg gccaaaaagg tgttcattga ggatgtcagc agggagtttg   1740
tggaggagtt catctggccg gccatccagt ccagcgcact gtatgaggac cgctacctcc   1800
tgggcacctc tcttgccagg ccctgcatcg cccgcaaaca agtggaaatc gcccagcggg   1860
agggggccaa gtatgtgtcc cacggcgcca caggaaaggg gaacgatcag gtccggtttg   1920
agctcagctg ctactcactg gcccccccaga taaaggtcat tgctccctgg aggatgcctg   1980
aattctacaa ccggttcaag ggccgcaatg acctgatgga gtacgcaaag caacacggga   2040
ttcccatccc ggtcactccc aagaacccgt ggagcatgga tgagaacctc atgcacatca   2100
gctacgaggc tggaatcctg gagaacccca agaaccaagc gcctccaggt ctctacacga   2160
agacccagga cccagccaaa gcccccaaca cccctgacat tctcgagatc gagttcaaaa   2220
aaggggtccc tgtgaaggtg accaacgtca aggatggcac cacccaccag acctccttgg   2280
agctcttcat gtacctgaac gaagtcgcgg gcaagcatgg cgtgggccgt attgacatcg   2340
tggagaaccg cttcattgga atgaagtccc gaggtatcta cgagacccca gcaggcacca   2400
tcctttacca cgctcattta gacatcgagg ccttcaccat ggaccgggaa gtgcgcaaaa   2460
```

```
tcaaacaagg cctgggcttg aaatttgctg agctggtgta taccggtttc tggcacagcc   2520
ctgagtgtga atttgtccgc cactgcatcg ccaagtccca ggagcgagtg gaagggaaag   2580
tgcaggtgtc cgtcctcaag ggccaggtgt acatcctcgg ccgggagtcc ccactgtctc   2640
tctacaatga ggagctggtg agcatgaacg tgcagggtga ttatgagcca actgatgcca   2700
ccgggttcat caacatcaat tccctcaggc tgaaggaata tcatcgtctc cagagcaagg   2760
tcactgccaa atgataagca tgcggatctg cctcgactgt gccttctagt tgccagccat   2820
ctgttgtttg cccctccccc gtgccttcct tgaccctgga aggtgccact cccactgtcc   2880
tttcctaata aaatgaggaa attgcatcgc attgtctgag taggtgtcat tctattctgg   2940
ggggtggggt ggggcaggac agcaaggggg aggattggga agacaatagc aggcatgctg   3000
gggactcgag ttaagggcga attcccgata aggatcttcc tagagcatgg ctacgtagat   3060
aagtagcatg gcgggttaat cattaactac aaggaacccc tagtgatgga gttggccact   3120
ccctctctgc gcgctcgctc gctcactgag gccgggcgac caaaggtcgc ccgacgcccg   3180
ggctttgccc gggcggcctc agtgagcgag cgagcgcgca gccttaatta acctaattca   3240
ctggccgtcg ttttacaacg tcgtgactgg gaaaaccctg gcgttaccca acttaatcgc   3300
cttgcagcac atcccccttt cgccagctgg cgtaatagcg aagaggcccg caccgatcgc   3360
ccttcccaac agttgcgcag cctgaatggc gaatgggacg cgccctgtag cggcgcatta   3420
agcgcggcgg gtgtggtggt tacgcgcagc gtgaccgcta cacttgccag cgccctagcg   3480
cccgctcctt tcgctttctt cccttccttt ctcgccacgt tcgccggctt tccccgtcaa   3540
gctctaaatc gggggctccc tttagggttc cgatttagtg ctttacggca cctcgacccc   3600
aaaaaacttg attagggtga tggttcacgt agtgggccat cgccctgata gacggttttt   3660
cgccctttga cgttggagtc cacgttcttt aatagtggac tcttgttcca aactggaaca   3720
acactcaacc ctatctcggt ctattctttt gatttataag ggattttgcc gatttcggcc   3780
tattggttaa aaaatgagct gatttaacaa aaatttaacg cgaattttaa caaaatatta   3840
acgcttacaa tttaggtggc acttttcggg gaaatgtgcg cggaacccct atttgtttat   3900
ttttctaaat acattcaaat atgtatccgc tcatgagaca ataaccctga taaatgcttc   3960
aataatattg aaaaaggaag agtatgagta ttcaacattt ccgtgtcgcc cttattccct   4020
tttttgcggc attttgcctt cctgtttttg ctcacccaga aacgctggtg aaagtaaaag   4080
atgctgaaga tcagttgggt gcacgagtgg gttacatcga actggatctc aacagcggta   4140
agatccttga gagttttcgc cccgaagaac gttttccaat gatgagcact tttaaagttc   4200
tgctatgtgg cgcggtatta tcccgtattg acgccgggca agagcaactc ggtcgccgca   4260
tacactattc tcagaatgac ttggttgagt actcaccagt cacagaaaag catcttacgg   4320
atggcatgac agtaagagaa ttatgcagtg ctgccataac catgagtgat aacactgcgg   4380
ccaacttact tctgacaacg atcggaggac cgaaggagct aaccgctttt ttgcacaaca   4440
tgggggatca tgtaactcgc cttgatcgtt gggaaccgga gctgaatgaa gccataccaa   4500
acgacgagcg tgacaccacg atgcctgtag caatggcaac aacgttgcgc aaactattaa   4560
ctggcgaact acttactcta gcttcccggc aacaattaat agactggatg gaggcggata   4620
aagttgcagg accacttctg cgctcggccc ttccggctgg ctggtttatt gctgataaat   4680
ctggagccgg tgagcgtggg tctcgcggta tcattgcagc actggggcca gatggtaagc   4740
cctcccgtat cgtagttatc tacacgacgg ggagtcaggc aactatggat gaacgaaata   4800
```

```
gacagatcgc tgagataggt gcctcactga ttaagcattg gtaactgtca gaccaagttt   4860
actcatatat actttagatt gatttaaaac ttcattttta atttaaaagg atctaggtga   4920
agatcctttt tgataatctc atgaccaaaa tcccttaacg tgagttttcg ttccactgag   4980
cgtcagaccc cgtagaaaag atcaaaggat cttcttgaga tccttttttt ctgcgcgtaa   5040
tctgctgctt gcaaacaaaa aaaccaccgc taccagcggt ggtttgtttg ccggatcaag   5100
agctaccaac tctttttccg aaggtaactg gcttcagcag agcgcagata ccaaatactg   5160
ttcttctagt gtagccgtag ttaggccacc acttcaagaa ctctgtagca ccgcctacat   5220
acctcgctct gctaatcctg ttaccagtgg ctgctgccag tggcgataag tcgtgtctta   5280
ccgggttgga ctcaagacga tagttaccgg ataaggcgca gcggtcgggc tgaacggggg   5340
gttcgtgcac acagcccagc ttggagcgaa cgacctacac cgaactgaga tacctacagc   5400
gtgagctatg agaaagcgcc acgcttcccg aagggagaaa ggcggacagg tatccggtaa   5460
gcggcagggt cggaacagga gagcgcacga gggagcttcc agggggaaac gcctggtatc   5520
tttatagtcc tgtcgggttt cgccacctct gacttgagcg tcgatttttg tgatgctcgt   5580
caggggggcg gagcctatgg aaaaacgcca gcaacgcggc ctttttacgg ttcctggcct   5640
tttgctggcc ttttgctcac atgttctttc ctgcgttatc ccctgattct gtggataacc   5700
gtattaccgc ctttgagtga gctgataccg ctcgccgcag ccgaacgacc gagcgcagcg   5760
agtcagtgag cgaggaagcg gaagagcgcc caatacgcaa accgcctctc cccgcgcgtt   5820
ggccgattca ttaatgcagc tggcacgaca ggtttcccga ctggaaagcg ggcagtgagc   5880
gcaacgcaat taatgtgagt tagctcactc attaggcacc ccaggcttta cactttatgc   5940
ttccggctcg tatgttgtgt ggaattgtga gcggataaca atttcacaca ggaaacagct   6000
atgaccatga ttacgccaga tttaattaag g                                  6031
```

<210> SEQ ID NO 33
<211> LENGTH: 6850
<212> TYPE: DNA
<213> ORGANISM: Artificial Sequence
<220> FEATURE:
<223> OTHER INFORMATION: constructed sequence

<400> SEQUENCE: 33

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagctagc ggatccaggt taatttttaa aaagcagtca    240
aaagtccaag tggcccttgg cagcatttac tctctctgtt tgctctggtt aataatctca    300
ggagcacaaa cattccagat ccaggttaat ttttaaaaag cagtcaaaag tccaagtggc    360
ccttggcagc atttactctc tctgtttgct ctggttaata atctcaggag cacaaacatt    420
ccagatccgg cgcgccaggg ctggaagcta cctttgacat catttcctct gcgaatgcat    480
gtataatttc tacagaacct attagaaagg atcacccagc ctctgctttt gtacaacttt    540
cccttaaaaa actgccaatt ccactgctgt ttggcccaat agtgagaact tttcctgct     600
gcctcttggt gcttttgcct atggccccta ttctgcctgc tgaagacact cttgccagca    660
tggacttaaa cccctccagc tctgacaatc ctctttctct tttgttttac atgaagggtc    720
tggcagccaa agcaatcact caaagttcaa accttatcat tttttgcttt gttcctcttg    780
gccttggttt tgtacatcag ctttgaaaat accatcccag ggttaatgct ggggttaatt    840
```

```
tataactaag agtgctctag ttttgcaata caggacatgc tataaaaatg gaaagatgtt    900
gctttctgag agagcggccg cgtttgtttc ctttttaaa atacattgag tatgcttgcc    960
ttttagatat agaaatatct gatgctgtct tcttcactaa attttgatta catgatttga   1020
cagcaatatt gaagagtcta acagccagca cgcaggttgg taagtactgg ttctttgtta   1080
gctaggtttt cttcttcttc atttttaaaa ctaaatagat cgacaatgct tatgatgcat   1140
ttatgtttaa taaacactgt tcagttcatg atttggtcat gtaattcctg ttagaaaaca   1200
ttcatctcct tggtttaaaa aaattaaaag tgggaaaaca aagaaatagc agaatatagt   1260
gaaaaaaaat aaccacatta tttttgtttg gacttaccac tttgaaatca aaatgggaaa   1320
caaaagcaca aacaatggcc ttatttacac aaaaagtctg attttaagat atatgacatt   1380
tcaaggtttc agaagtatgt aatgaggtgt gtctctaatt ttttaaatta tatatcttca   1440
atttaaagtt ttagttaaaa cataaagatt aacctttcat tagcaagctg ttagttatca   1500
ccaaagcttt tcatggatta ggaaaaaatc attttgtctc tatgtcaaac atcttggagt   1560
tgatatttgg ggaaacacaa tactcagttg agttccctag gggagaaaag caagcttaag   1620
aattgacata aagagtagga agttagctaa tgcaacatat atcactttgt tttttcacaa   1680
ctacagtgac tttatgtatt tcccagagga aggcatacag ggaagaaatt atcccatttg   1740
gacaaacagc atgttctcac aggaagcatt tatcacactt acttgtcaac tttctagaat   1800
caaatctagt agctgacagt accaggatca ggggtgccaa ccctaagcac ccccagaaag   1860
ctgactggcc ctgtggttcc cactccagac atgatgtcag ctggaccata attaggcttc   1920
tgttcttcag gagacatttg ttcaaagtca tttgggcaac catattctga aaacagccca   1980
gccagggtga tggatcactt tgcaaagatc ctcaatgagc tattttcaag tgatgacaaa   2040
gtgtgaagtt aaccgctcat ttgagaactt tctttttcat ccaaagtaaa ttcaaatatg   2100
attagaaatc tgacctttta ttactggaat tctcttgact aaaagtaaaa ttgaatttta   2160
attcctaaat ctccatgtgt atacagtact gtgggaacat cacagatttt ggctccatgc   2220
cctaaagaga aattggcttt cagattattt ggattaaaaa caaagacttt cttaagagat   2280
gtaaaatttt catgatgttt tctttttgc taaaactaaa gaattattct tttacatttc    2340
agatggccgc caccatgagc agcaagggct ctgtggtgct ggcctactct ggcggcctgg   2400
acaccagctg tatcctcgtg tggctgaaag aacagggcta cgacgtgatc gcctacctgg   2460
ccaacatcgg ccagaaagag gacttcgagg aagcccggaa gaaggccctg aagctgggcg   2520
ccaagaaggt gttcatcgag gacgtgtccc gcgagttcgt ggaagagttc atctggcccg   2580
ccatccagag cagcgccctg tacgaggaca gatacctgct gggcaccagc ctggccagac   2640
cctgtatcgc ccggaaacag gtggaaatcg cccagcgcga gggcgccaaa tacgtgtctc   2700
acggcgccac cggcaagggc aacgaccagg tgcgctttga gctgagctgc tactccctgg   2760
ccccccagat caaagtgatc gccccttggc ggatgcccga gttctacaac cggttcaagg   2820
gccggaacga cctgatggaa tacgccaagc agcacggcat ccccatcccc gtgaccccca   2880
agaacccttg gagcatggac gagaacctga tgcacatcag ctacgaggcc ggcatcctgg   2940
aaaaccccaa gaatcaggcc cctcccggcc tgtacacaaa gacccaggac cctgccaagg   3000
cccccaacac ccccgacatt ctggaaatcg agttcaagaa aggcgtgccc gtgaaagtga   3060
ccaacgtgaa ggacggcacc acccaccaga cctccctgga actgttcatg tacctgaacg   3120
aggtggccgg caagcacggc gtgggcagaa tcgacatcgt ggaaaacaga ttcatcggca   3180
```

-continued

```
tgaagtcccg gggcatctac gagacaccag ccggcaccat cctgtaccac gcccacctgg   3240
atatcgaggc cttcaccatg gaccgggaag tgcggaagat caagcagggc ctgggcctga   3300
agttcgccga gctggtgtac acaggctttt ggcacagccc cgagtgcgag tttgtgcggc   3360
actgcattgc caagagccag gaacgggtgg aaggcaaggt gcaggtgtcc gtgctgaagg   3420
gccaggtgta cattctgggc agagagagcc ccctgagcct gtacaacgag gaactggtgt   3480
ctatgaacgt gcagggcgac tacgagccca ccgacgccac cggcttcatc aacatcaaca   3540
gcctgagact gaaagagtac caccggctgc agtccaaagt gaccgccaag tgataagcat   3600
gcggatctgc ctcgactgtg ccttctagtt gccagccatc tgttgtttgc ccctcccccg   3660
tgccttcctt gaccctggaa ggtgccactc ccactgtcct ttcctaataa aatgaggaaa   3720
ttgcatcgca ttgtctgagt aggtgtcatt ctattctggg gggtggggtg gggcaggaca   3780
gcaaggggga ggattgggaa gacaatagca ggcatgctgg ggactcgagt taagggcgaa   3840
ttcccgataa ggatcttcct agagcatggc tacgtagata agtagcatgg cgggttaatc   3900
attaactaca aggaacccct agtgatggag ttggccactc cctctctgcg cgctcgctcg   3960
ctcactgagg ccgggcgacc aaaggtcgcc cgacgcccgg gctttgcccg ggcggcctca   4020
gtgagcgagc gagcgcgcag ccttaattaa cctaattcac tggccgtcgt tttacaacgt   4080
cgtgactggg aaaaccctgg cgttacccaa cttaatcgcc ttgcagcaca tccccctttc   4140
gccagctggc gtaatagcga agaggcccgc accgatcgcc cttcccaaca gttgcgcagc   4200
ctgaatggcg aatgggacgc gccctgtagc ggcgcattaa gcgcggcggg tgtggtggtt   4260
acgcgcagcg tgaccgctac acttgccagc gccctagcgc ccgctccttt cgctttcttc   4320
ccttcctttc tcgccacgtt cgccggcttt ccccgtcaag ctctaaatcg ggggctccct   4380
ttagggttcc gatttagtgc tttacggcac ctcgacccca aaaaacttga ttagggtgat   4440
ggttcacgta gtgggccatc gccctgatag acggtttttc gccctttgac gttggagtcc   4500
acgttcttta atagtggact cttgttccaa actggaacaa cactcaaccc tatctcggtc   4560
tattcttttg atttataagg gattttgccg atttcggcct attggttaaa aaatgagctg   4620
atttaacaaa aatttaacgc gaattttaac aaaatattaa cgcttacaat ttaggtggca   4680
cttttcgggg aaatgtgcgc ggaaccccta tttgtttatt tttctaaata cattcaaata   4740
tgtatccgct catgagacaa taaccctgat aaatgcttca ataatattga aaaaggaaga   4800
gtatgagtat tcaacatttc cgtgtcgccc ttattccctt ttttgcggca ttttgccttc   4860
ctgtttttgc tcacccagaa acgctggtga aagtaaaaga tgctgaagat cagttgggtg   4920
cacgagtggg ttacatcgaa ctggatctca acagcggtaa gatccttgag agttttcgcc   4980
ccgaagaacg ttttccaatg atgagcactt ttaaagttct gctatgtggc gcggtattat   5040
cccgtattga cgccgggcaa gagcaactcg gtcgccgcat acactattct cagaatgact   5100
tggttgagta ctcaccagtc acagaaaagc atcttacgga tggcatgaca gtaagagaat   5160
tatgcagtgc tgccataacc atgagtgata acactgcggc caacttactt ctgacaacga   5220
tcggaggacc gaaggagcta accgcttttt tgcacaacat gggggatcat gtaactcgcc   5280
ttgatcgttg ggaaccggag ctgaatgaag ccataccaaa cgacgagcgt gacaccacga   5340
tgcctgtagc aatggcaaca acgttgcgca aactattaac tggcgaacta cttactctag   5400
cttcccggca acaattaata gactggatgg aggcggataa agttgcagga ccacttctgc   5460
gctcggccct tccggctggc tggtttattg ctgataaatc tggagccggt gagcgtgggt   5520
ctcgcggtat cattgcagca ctggggccag atggtaagcc ctcccgtatc gtagttatct   5580
```

acacgacggg gagtcaggca actatggatg aacgaaatag acagatcgct gagataggtg 5640
cctcactgat taagcattgg taactgtcag accaagttta ctcatatata ctttagattg 5700
atttaaaact tcatttttaa tttaaaagga tctaggtgaa gatccttttt gataatctca 5760
tgaccaaaat cccttaacgt gagttttcgt tccactgagc gtcagacccc gtagaaaaga 5820
tcaaaggatc ttcttgagat cctttttttc tgcgcgtaat ctgctgcttg caaacaaaaa 5880
aaccaccgct accagcggtg gtttgtttgc cggatcaaga gctaccaact ctttttccga 5940
aggtaactgg cttcagcaga gcgcagatac caaatactgt tcttctagtg tagccgtagt 6000
taggccacca cttcaagaac tctgtagcac cgcctacata cctcgctctg ctaatcctgt 6060
taccagtggc tgctgccagt ggcgataagt cgtgtcttac cgggttggac tcaagacgat 6120
agttaccgga taaggcgcag cggtcgggct gaacgggggg ttcgtgcaca cagcccagct 6180
tggagcgaac gacctacacc gaactgagat acctacagcg tgagctatga gaaagcgcca 6240
cgcttcccga agggagaaag gcggacaggt atccggtaag cggcagggtc ggaacaggag 6300
agcgcacgag ggagcttcca gggggaaacg cctggtatct ttatagtcct gtcgggtttc 6360
gccacctctg acttgagcgt cgatttttgt gatgctcgtc aggggggcgg agcctatgga 6420
aaaacgccag caacgcggcc tttttacggt tcctggcctt ttgctggcct tttgctcaca 6480
tgttctttcc tgcgttatcc cctgattctg tggataaccg tattaccgcc tttgagtgag 6540
ctgataccgc tcgccgcagc cgaacgaccg agcgcagcga gtcagtgagc gaggaagcgg 6600
aagagcgccc aatacgcaaa ccgcctctcc ccgcgcgttg gccgattcat taatgcagct 6660
ggcacgacag gtttcccgac tggaaagcgg gcagtgagcg caacgcaatt aatgtgagtt 6720
agctcactca ttaggcaccc caggctttac actttatgct tccggctcgt atgttgtgtg 6780
gaattgtgag cggataacaa tttcacacag gaaacagcta tgaccatgat tacgccagat 6840
ttaattaagg 6850

<210> SEQ ID NO 34
<211> LENGTH: 5608
<212> TYPE: DNA
<213> ORGANISM: Artificial Sequence
<220> FEATURE:
<223> OTHER INFORMATION: constructed sequence

<400> SEQUENCE: 34
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctacc tcgtgatcgc ccggcccctg ttcaaacatg 240
tcctaatact ctgtctctgc aagggtcatc agtagttttc catcttactc aacatcctcc 300
cagtggaatt catttcatag aacgaatgtt ccgatgctct aatctctcta gacaaggttc 360
atatttgtat gggttactta ttctctcttt gttgactaag tcaataatca gaatcagcag 420
gtttgcagtc agattggcag ggataagcag cctagctcag gagaagtgag tataaaagcc 480
ccaggctggg agcagccatc agcggccgat ctagcttact tgtggtacca gctcggatcc 540
tgagaacttc agggtgagtc tatgggaccc ttgatgtttt ctttcccctt cttttctatg 600
gttaagttca tgtcatagga aggggagaag taacagggta cacatattga ccaaatcagg 660
gtaattttgc atttgtaatt ttaaaaaatg ctttcttctt ttaatatact tttttgttta 720

-continued

```
tcttatttct aatactttcc ctaatctctt tctttcaggg caataatgat acaatgtatc    780
atgcctcttt gcaccattct aaagaataac agtgataatt tctgggttaa ggcaatagca    840
atatttctgc atataaatat ttctgcatat aaattgtaac tgatgtaaga ggtttcatat    900
tgctaatagc agctacaatc cagctaccat tctgctttta ttttatggtt gggataaggc    960
tggattattc tgagtccaag ctaggccctt ttgctaatca tgttcatacc tcttatcttc   1020
ctcccacagc tcctgggcaa cgtgctggtc tgtgtgctgg cccatcactt tggcaaagaa   1080
ttgatctcga gtaactgaag gcggccgcca ccatgtccag caaaggctcc gtggttctgg   1140
cctacagtgg cggcctggac acctcgtgca tcctcgtgtg gctgaaggaa caaggctatg   1200
acgtcattgc ctatctggcc aacattggcc agaaggaaga cttcgaggaa gccaggaaga   1260
aggcactgaa gcttggggcc aaaaaggtgt tcattgagga tgtcagcagg gagtttgtgg   1320
aggagttcat ctggccggcc atccagtcca gcgcactgta tgaggaccgc tacctcctgg   1380
gcacctctct tgccaggccc tgcatcgccc gcaaacaagt ggaaatcgcc cagcgggagg   1440
gggccaagta tgtgtcccac ggcgccacag gaaaggggaa cgatcaggtc cggtttgagc   1500
tcagctgcta ctcactggcc ccccagataa aggtcattgc tccctggagg atgcctgaat   1560
tctacaaccg gttcaagggc cgcaatgacc tgatggagta cgcaaagcaa cacgggattc   1620
ccatcccggt cactcccaag aacccgtgga gcatggatga gaacctcatg cacatcagct   1680
acgaggctgg aatcctggag aaccccaaga accaagcgcc tccaggtctc tacacgaaga   1740
cccaggaccc agccaaagcc cccaacaccc ctgacattct cgagatcgag ttcaaaaaag   1800
gggtccctgt gaaggtgacc aacgtcaagg atggcaccac ccaccagacc tccttggagc   1860
tcttcatgta cctgaacgaa gtcgcgggca agcatggcgt gggccgtatt gacatcgtgg   1920
agaaccgctt cattggaatg aagtcccgag gtatctacga gaccccagca ggcaccatcc   1980
tttaccacgc tcatttagac atcgaggcct tcaccatgga ccgggaagtg cgcaaaatca   2040
aacaaggcct gggcttgaaa tttgctgagc tggtgtatac cggtttctgg cacagccctg   2100
agtgtgaatt tgtccgccac tgcatcgcca agtcccagga gcgagtggaa gggaaagtgc   2160
aggtgtccgt cctcaagggc caggtgtaca tcctcggccg ggagtcccca ctgtctctct   2220
acaatgagga gctggtgagc atgaacgtgc agggtgatta tgagccaact gatgccaccg   2280
ggttcatcaa catcaattcc ctcaggctga aggaatatca tcgtctccag agcaaggtca   2340
ctgccaaatg ataagcatgc ggatctgcct cgactgtgcc ttctagttgc cagccatctg   2400
ttgtttgccc ctcccccgtg ccttccttga ccctggaagg tgccactccc actgtccttt   2460
cctaataaaa tgaggaaatt gcatcgcatt gtctgagtag gtgtcattct attctggggg   2520
gtggggtggg gcaggacagc aagggggagg attgggaaga caatagcagg catgctgggg   2580
actcgagtta agggcgaatt cccgataagg atcttcctag agcatggcta cgtagataag   2640
tagcatggcg ggttaatcat taactacaag gaacccctag tgatggagtt ggccactccc   2700
tctctgcgcg ctcgctcgct cactgaggcc gggcgaccaa aggtcgcccg acgcccgggc   2760
tttgcccggg cggcctcagt gagcgagcga gcgcgcagcc ttaattaacc taattcactg   2820
gccgtcgttt tacaacgtcg tgactgggaa aaccctggcg ttacccaact taatcgcctt   2880
gcagcacatc cccctttcgc cagctggcgt aatagcgaag aggcccgcac cgatcgccct   2940
tcccaacagt tgcgcagcct gaatggcgaa tgggacgcgc cctgtagcgg cgcattaagc   3000
gcggcgggtg tggtggttac gcgcagcgtg accgctacac ttgccagcgc cctagcgccc   3060
gctcctttcg ctttcttccc ttcctttctc gccacgttcg ccggctttcc ccgtcaagct   3120
```

-continued

```
ctaaatcggg ggctcccttt agggttccga tttagtgctt tacggcacct cgaccccaaa   3180
aaacttgatt agggtgatgg ttcacgtagt gggccatcgc cctgatagac ggtttttcgc   3240
cctttgacgt tggagtccac gttctttaat agtggactct tgttccaaac tggaacaaca   3300
ctcaacccta tctcggtcta ttcttttgat ttataaggga ttttgccgat ttcggcctat   3360
tggttaaaaa atgagctgat ttaacaaaaa tttaacgcga attttaacaa aatattaacg   3420
cttacaattt aggtggcact tttcggggaa atgtgcgcgg aacccctatt tgtttatttt   3480
tctaaataca ttcaaatatg tatccgctca tgagacaata accctgataa atgcttcaat   3540
aatattgaaa aaggaagagt atgagtattc aacatttccg tgtcgccctt attccctttt   3600
ttgcggcatt ttgccttcct gtttttgctc acccagaaac gctggtgaaa gtaaaagatg   3660
ctgaagatca gttgggtgca cgagtgggtt acatcgaact ggatctcaac agcggtaaga   3720
tccttgagag ttttcgcccc gaagaacgtt ttccaatgat gagcactttt aaagttctgc   3780
tatgtggcgc ggtattatcc cgtattgacg ccgggcaaga gcaactcggt cgccgcatac   3840
actattctca gaatgacttg gttgagtact caccagtcac agaaaagcat cttacggatg   3900
gcatgacagt aagagaatta tgcagtgctg ccataaccat gagtgataac actgcggcca   3960
acttacttct gacaacgatc ggaggaccga aggagctaac cgcttttttg cacaacatgg   4020
gggatcatgt aactcgcctt gatcgttggg aaccggagct gaatgaagcc ataccaaacg   4080
acgagcgtga caccacgatg cctgtagcaa tggcaacaac gttgcgcaaa ctattaactg   4140
gcgaactact tactctagct tcccggcaac aattaataga ctggatggag gcggataaag   4200
ttgcaggacc acttctgcgc tcggcccttc cggctggctg gtttattgct gataaatctg   4260
gagccggtga gcgtgggtct cgcggtatca ttgcagcact ggggccagat ggtaagccct   4320
cccgtatcgt agttatctac acgacgggga gtcaggcaac tatggatgaa cgaaatagac   4380
agatcgctga gataggtgcc tcactgatta agcattggta actgtcagac caagtttact   4440
catatatact ttagattgat ttaaaacttc atttttaatt taaaaggatc taggtgaaga   4500
tcctttttga taatctcatg accaaaatcc cttaacgtga gttttcgttc cactgagcgt   4560
cagaccccgt agaaaagatc aaaggatctt cttgagatcc tttttttctg cgcgtaatct   4620
gctgcttgca aacaaaaaaa ccaccgctac cagcggtggt ttgtttgccg gatcaagagc   4680
taccaactct ttttccgaag gtaactggct tcagcagagc gcagatacca aatactgttc   4740
ttctagtgta gccgtagtta ggccaccact tcaagaactc tgtagcaccg cctacatacc   4800
tcgctctgct aatcctgtta ccagtggctg ctgccagtgg cgataagtcg tgtcttaccg   4860
ggttggactc aagacgatag ttaccggata aggcgcagcg gtcgggctga acggggggtt   4920
cgtgcacaca gcccagcttg gagcgaacga cctacaccga actgagatac ctacagcgtg   4980
agctatgaga aagcgccacg cttcccgaag ggagaaaggc ggacaggtat ccggtaagcg   5040
gcagggtcgg aacaggagag cgcacgaggg agcttccagg gggaaacgcc tggtatcttt   5100
atagtcctgt cgggtttcgc cacctctgac ttgagcgtcg atttttgtga tgctcgtcag   5160
gggggcggag cctatggaaa aacgccagca acgcggcctt tttacggttc ctggcctttt   5220
gctggccttt tgctcacatg ttctttcctg cgttatcccc tgattctgtg gataaccgta   5280
ttaccgcctt tgagtgagct gataccgctc gccgcagccg aacgaccgag cgcagcgagt   5340
cagtgagcga ggaagcggaa gagcgcccaa tacgcaaacc gcctctcccc gcgcgttggc   5400
cgattcatta atgcagctgg cacgacaggt ttcccgactg gaaagcgggc agtgagcgca   5460
```

acgcaattaa tgtgagttag ctcactcatt aggcacccca ggctttacac tttatgcttc 5520
cggctcgtat gttgtgtgga attgtgagcg gataacaatt tcacacagga aacagctatg 5580
accatgatta cgccagattt aattaagg 5608

<210> SEQ ID NO 35
<211> LENGTH: 5876
<212> TYPE: DNA
<213> ORGANISM: Artificial Sequence
<220> FEATURE:
<223> OTHER INFORMATION: constructed sequence

<400> SEQUENCE: 35
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctagc cgctgacaag gctcagaggc acacaggagt 240
ttctgggctc accctgcccc cttccaaccc ctcagttccc atcctccagc agctgtttgt 300
gtgctgcctc tgaagtccac actgaacaaa cttcagccta ctcatgtccc taaaatgggc 360
aaacattgca agcagcaaac agcaaacaca cagccctccc tgcctgctga ccttggagct 420
ggggcagagg tcagagacct ctctgggccc atgccacctc caacatccac tcgacccctt 480
ggaatttcgg tggagaggag cagaggttgt cctggcgtgg tttaggtagt gtgagaggga 540
gatccggcgc gcctggacac aggacgctgt ggtttctgag ccagggggcg actcagatcc 600
cagccagtgg acttagcccc tgtttgctcc tccgataact ggggtgacct tggttaatat 660
tcaccagcag cctcccccgt tgcccctctg gatccactgc ttaaatacgg acgaggacag 720
ggccctgtct cctcagcttc aggcaccacc actgacctgg gacagtgaat agcgagatct 780
agcttacttg tggtaccagc tcggatcctg agaacttcag ggtgagtcta tgggaccctt 840
gatgttttct ttccccttct tttctatggt taagttcatg tcataggaag gggagaagta 900
acagggtaca catattgacc aaatcagggt aattttgcat ttgtaatttt aaaaaatgct 960
ttcttctttt aatatacttt tttgtttatc ttatttctaa tactttccct aatctctttc 1020
tttcagggca ataatgatac aatgtatcat gcctctttgc accattctaa agaataacag 1080
tgataatttc tgggttaagg caatagcaat atttctgcat ataaatattt ctgcatataa 1140
attgtaactg atgtaagagg tttcatattg ctaatagcag ctacaatcca gctaccattc 1200
tgcttttatt ttatggttgg gataaggctg gattattctg agtccaagct aggccctttt 1260
gctaatcatg ttcatacctc ttatcttcct cccacagctc ctgggcaacg tgctggtctg 1320
tgtgctggcc catcactttg gcaaagaatt gatctcgagt aactgaaggc ggccgccacc 1380
atgtccagca aaggctccgt ggttctggcc tacagtggcg gcctggacac ctcgtgcatc 1440
ctcgtgtggc tgaaggaaca aggctatgac gtcattgcct atctggccaa cattggccag 1500
aaggaagact tcgaggaagc caggaagaag gcactgaagc ttggggccaa aaaggtgttc 1560
attgaggatg tcagcaggga gtttgtggag gagttcatct ggccggccat ccagtccagc 1620
gcactgtatg aggaccgcta cctcctgggc acctctcttg ccaggccctg catcgcccgc 1680
aaacaagtgg aaatcgccca gcgggagggg gccaagtatg tgtcccacgg cgccacagga 1740
aaggggaacg atcaggtccg gtttgagctc agctgctact cactggcccc ccagataaag 1800
gtcattgctc cctggaggat gcctgaattc tacaaccggt tcaagggccg caatgacctg 1860
atggagtacg caaagcaaca cgggattccc atcccggtca ctcccaagaa cccgtggagc 1920

```
atggatgaga acctcatgca catcagctac gaggctggaa tcctggagaa ccccaagaac   1980
caagcgcctc caggtctcta cacgaagacc caggacccag ccaaagcccc caacacccct   2040
gacattctcg agatcgagtt caaaaaaggg gtccctgtga aggtgaccaa cgtcaaggat   2100
ggcaccaccc accagacctc cttggagctc ttcatgtacc tgaacgaagt cgcgggcaag   2160
catggcgtgg gccgtattga catcgtggag aaccgcttca ttggaatgaa gtcccgaggt   2220
atctacgaga ccccagcagg caccatcctt taccacgctc atttagacat cgaggccttc   2280
accatggacc gggaagtgcg caaaatcaaa caaggcctgg gcttgaaatt tgctgagctg   2340
gtgtataccg gtttctggca cagccctgag tgtgaatttg tccgccactg catcgccaag   2400
tcccaggagc gagtggaagg gaaagtgcag gtgtccgtcc tcaagggcca ggtgtacatc   2460
ctcggccggg agtccccact gtctctctac aatgaggagc tggtgagcat gaacgtgcag   2520
ggtgattatg agccaactga tgccaccggg ttcatcaaca tcaattccct caggctgaag   2580
gaatatcatc gtctccagag caaggtcact gccaaatgat aagcatgcgg atctgcctcg   2640
actgtgcctt ctagttgcca gccatctgtt gtttgcccct cccccgtgcc ttccttgacc   2700
ctggaaggtg ccactcccac tgtcctttcc taataaaatg aggaaattgc atcgcattgt   2760
ctgagtaggt gtcattctat tctggggggt ggggtggggc aggacagcaa gggggaggat   2820
tgggaagaca atagcaggca tgctggggac tcgagttaag ggcgaattcc cgataaggat   2880
cttcctagag catggctacg tagataagta gcatggcggg ttaatcatta actacaagga   2940
acccctagtg atggagttgg ccactccctc tctgcgcgct cgctcgctca ctgaggccgg   3000
gcgaccaaag gtcgcccgac gcccgggctt tgcccgggcg gcctcagtga gcgagcgagc   3060
gcgcagcctt aattaaccta attcactggc cgtcgtttta caacgtcgtg actgggaaaa   3120
ccctggcgtt acccaactta atcgccttgc agcacatccc cctttcgcca gctggcgtaa   3180
tagcgaagag gcccgcaccg atcgcccttc ccaacagttg cgcagcctga atggcgaatg   3240
ggacgcgccc tgtagcggcg cattaagcgc ggcgggtgtg gtggttacgc gcagcgtgac   3300
cgctacactt gccagcgccc tagcgcccgc tcctttcgct ttcttccctt cctttctcgc   3360
cacgttcgcc ggctttcccc gtcaagctct aaatcggggg ctccctttag ggttccgatt   3420
tagtgcttta cggcacctcg accccaaaaa acttgattag ggtgatggtt cacgtagtgg   3480
gccatcgccc tgatagacgg tttttcgccc tttgacgttg gagtccacgt tctttaatag   3540
tggactcttg ttccaaactg gaacaacact caaccctatc tcggtctatt cttttgattt   3600
ataagggatt ttgccgattt cggcctattg gttaaaaaat gagctgattt aacaaaaatt   3660
taacgcgaat tttaacaaaa tattaacgct tacaatttag gtggcacttt tcggggaaat   3720
gtgcgcggaa cccctatttg tttatttttc taaatacatt caaatatgta tccgctcatg   3780
agacaataac cctgataaat gcttcaataa tattgaaaaa ggaagagtat gagtattcaa   3840
catttccgtg tcgcccttat tccctttttt gcggcatttt gccttcctgt ttttgctcac   3900
ccagaaacgc tggtgaaagt aaaagatgct gaagatcagt tgggtgcacg agtgggttac   3960
atcgaactgg atctcaacag cggtaagatc cttgagagtt ttcgccccga agaacgtttt   4020
ccaatgatga gcacttttaa agttctgcta tgtggcgcgg tattatcccg tattgacgcc   4080
gggcaagagc aactcggtcg ccgcatacac tattctcaga atgacttggt tgagtactca   4140
ccagtcacag aaaagcatct tacggatggc atgacagtaa gagaattatg cagtgctgcc   4200
ataaccatga gtgataacac tgcggccaac ttacttctga caacgatcgg aggaccgaag   4260
```

gagctaaccg cttttttgca caacatgggg gatcatgtaa ctcgccttga tcgttgggaa 4320
ccggagctga atgaagccat accaaacgac gagcgtgaca ccacgatgcc tgtagcaatg 4380
gcaacaacgt tgcgcaaact attaactggc gaactactta ctctagcttc ccggcaacaa 4440
ttaatagact ggatggaggc ggataaagtt gcaggaccac ttctgcgctc ggcccttccg 4500
gctggctggt ttattgctga taaatctgga gccggtgagc gtgggtctcg cggtatcatt 4560
gcagcactgg ggccagatgg taagccctcc cgtatcgtag ttatctacac gacggggagt 4620
caggcaacta tggatgaacg aaatagacag atcgctgaga taggtgcctc actgattaag 4680
cattggtaac tgtcagacca agtttactca tatatacttt agattgattt aaaacttcat 4740
ttttaattta aaaggatcta ggtgaagatc ctttttgata atctcatgac caaaatccct 4800
taacgtgagt tttcgttcca ctgagcgtca gaccccgtag aaaagatcaa aggatcttct 4860
tgagatcctt tttttctgcg cgtaatctgc tgcttgcaaa caaaaaaacc accgctacca 4920
gcggtggttt gtttgccgga tcaagagcta ccaactcttt ttccgaaggt aactggcttc 4980
agcagagcgc agataccaaa tactgttctt ctagtgtagc cgtagttagg ccaccacttc 5040
aagaactctg tagcaccgcc tacatacctc gctctgctaa tcctgttacc agtggctgct 5100
gccagtggcg ataagtcgtg tcttaccggg ttggactcaa gacgatagtt accggataag 5160
gcgcagcggt cgggctgaac ggggggttcg tgcacacagc ccagcttgga gcgaacgacc 5220
tacaccgaac tgagatacct acagcgtgag ctatgagaaa gcgccacgct tcccgaaggg 5280
agaaaggcgg acaggtatcc ggtaagcggc agggtcggaa caggagagcg cacgagggag 5340
cttccagggg gaaacgcctg gtatctttat agtcctgtcg ggtttcgcca cctctgactt 5400
gagcgtcgat ttttgtgatg ctcgtcaggg gggcggagcc tatggaaaaa cgccagcaac 5460
gcggcctttt tacggttcct ggccttttgc tggccttttg ctcacatgtt ctttcctgcg 5520
ttatcccctg attctgtgga taaccgtatt accgcctttg agtgagctga taccgctcgc 5580
cgcagccgaa cgaccgagcg cagcgagtca gtgagcgagg aagcggaaga gcgcccaata 5640
cgcaaaccgc ctctccccgc gcgttggccg attcattaat gcagctggca cgacaggttt 5700
cccgactgga aagcgggcag tgagcgcaac gcaattaatg tgagttagct cactcattag 5760
gcaccccagg ctttacactt tatgcttccg gctcgtatgt tgtgtggaat tgtgagcgga 5820
taacaatttc acacaggaaa cagctatgac catgattacg ccagatttaa ttaagg 5876

<210> SEQ ID NO 36
<211> LENGTH: 4393
<212> TYPE: DNA
<213> ORGANISM: adeno-associated virus 8

<400> SEQUENCE: 36
cagagaggga gtggccaact ccatcactag gggtagcgcg aagcgcctcc cacgctgccg 60
cgtcagcgct gacgtaaatt acgtcatagg ggagtggtcc tgtattagct gtcacgtgag 120
tgcttttgcg gcattttgcg acaccacgtg gccatttgag gtatatatgg ccgagtgagc 180
gagcaggatc tccattttga ccgcgaaatt tgaacgagca gcagccatgc cgggcttcta 240
cgagatcgtg atcaaggtgc cgagcgacct ggacgagcac ctgccgggca tttctgactc 300
gtttgtgaac tgggtggccg agaaggaatg ggagctgccc ccggattctg acatggatcg 360
gaatctgatc gagcaggcac ccctgaccgt ggccgagaag ctgcagcgcg acttcctggt 420
ccaatggcgc cgcgtgagta aggccccgga ggccctcttc tttgttcagt tcgagaaggg 480
cgagagctac tttcacctgc acgttctggt cgagaccacg gggtcaagt ccatggtgct 540

-continued

```
aggccgcttc ctgagtcaga ttcgggaaaa gcttggtcca gaccatctac ccgcggggtc    600
gagccccacc ttgcccaact ggttcgcggt gaccaaagac gcggtaatgg cgccggcggg    660
ggggaacaag gtggtggacg agtgctacat ccccaactac ctcctgccca agactcagcc    720
cgagctgcag tgggcgtgga ctaacatgga ggagtatata agcgcgtgct tgaacctggc    780
cgagcgcaaa cggctcgtgg cgcagcacct gacccacgtc agccagacgc aggagcagaa    840
caaggagaat ctgaacccca attctgacgc gcccgtgatc aggtcaaaaa cctccgcgcg    900
ctatatggag ctggtcgggt ggctggtgga ccggggcatc acctccgaga agcagtggat    960
ccaggaggac caggcctcgt acatctcctt caacgccgcc tccaactcgc ggtcccagat   1020
caaggccgcg ctggacaatg ccggcaagat catggcgctg accaaatccg cgcccgacta   1080
cctggtgggg ccctcgctgc ccgcggacat tacccagaac cgcatctacc gcatcctcgc   1140
tctcaacggc tacgaccctg cctacgccgg ctccgtcttt ctcggctggg ctcagaaaaa   1200
gttcgggaaa cgcaacacca tctggctgtt tggacccgcc accaccggca agaccaacat   1260
tgcggaagcc atcgcccacg ccgtgccctt ctacggctgc gtcaactgga ccaatgagaa   1320
ctttcccttc aatgattgcg tcgacaagat ggtgatctgg tgggaggagg gcaagatgac   1380
ggccaaggtc gtggagtccg ccaaggccat tctcggcggc agcaaggtgc gcgtggacca   1440
aaagtgcaag tcgtccgccc agatcgaccc cacccccgtg atcgtcacct ccaacaccaa   1500
catgtgcgcc gtgattgacg ggaacagcac caccttcgag caccagcagc ctctccagga   1560
ccggatgttt aagttcgaac tcacccgccg tctggagcac gactttggca aggtgacaaa   1620
gcaggaagtc aaagagttct tccgctgggc cagtgatcac gtgaccgagg tggcgcatga   1680
gttttacgtc agaaagggcg gagccagcaa aagacccgcc cccgatgacg cggataaaag   1740
cgagcccaag cgggcctgcc cctcagtcgc ggatccatcg acgtcagacg cggaaggagc   1800
tccggtggac tttgccgaca ggtaccaaaa caaatgttct cgtcacgcgg gcatgcttca   1860
gatgctgttt ccctgcaaaa cgtgcgagag aatgaatcag aatttcaaca tttgcttcac   1920
acacggggtc agagactgct cagagtgttt ccccggcgtg tcagaatctc aaccggtcgt   1980
cagaaagagg acgtatcgga aactctgtgc gattcatcat ctgctggggc gggctcccga   2040
gattgcttgc tcggcctgcg atctggtcaa cgtggacctg gatgactgtg tttctgagca   2100
ataaatgact taaaccaggt atggctgccg atggttatct tccagattgg ctcgaggaca   2160
acctctctga gggcattcgc gagtggtggg cgctgaaacc tggagccccg aagcccaaag   2220
ccaaccagca aaagcaggac gacggccggg gtctggtgct tcctggctac aagtacctcg   2280
gacccttcaa cggactcgac aagggggagc ccgtcaacgc ggcggacgca gcggccctcg   2340
agcacgacaa ggcctacgac cagcagctgc aggcgggtga caatccgtac ctgcggtata   2400
accacgccga cgccgagttt caggagcgtc tgcaagaaga tacgtctttt gggggcaacc   2460
tcgggcgagc agtcttccag gccaagaagc gggttctcga acctctcggt ctggttgagg   2520
aaggcgctaa gacggctcct ggaaagaaga gaccggtaga gccatcaccc cagcgttctc   2580
cagactcctc tacgggcatc ggcaagaaag gccaacagcc cgccagaaaa agactcaatt   2640
ttggtcagac tggcgactca gagtcagttc cagaccctca acctctcgga gaacctccag   2700
cagcgccctc tggtgtggga cctaatacaa tggctgcagg cggtggcgca ccaatggcag   2760
acaataacga aggcgccgac ggagtgggta gttcctcggg aaattggcat tgcgattcca   2820
catggctggg cgacagagtc atcaccacca gcacccgaac ctgggccctg cccacctaca   2880
```

-continued

```
acaaccacct ctacaagcaa atctccaacg ggacatcggg aggagccacc aacgacaaca   2940

cctacttcgg ctacagcacc ccctgggggt attttgactt taacagattc cactgccact   3000

tttcaccacg tgactggcag cgactcatca acaacaactg gggattccgg cccaagagac   3060

tcagcttcaa gctcttcaac atccaggtca aggaggtcac gcagaatgaa ggcaccaaga   3120

ccatcgccaa taacctcacc agcaccatcc aggtgtttac ggactcggag taccagctgc   3180

cgtacgttct cggctctgcc caccagggct gcctgcctcc gttcccggcg gacgtgttca   3240

tgattcccca gtacggctac ctaacactca acaacggtag tcaggccgtg ggacgctcct   3300

ccttctactg cctggaatac tttccttcgc agatgctgag aaccggcaac aacttccagt   3360

ttacttacac cttcgaggac gtgcctttcc acagcagcta cgcccacagc cagagcttgg   3420

accggctgat gaatcctctg attgaccagt acctgtacta cttgtctcgg actcaaacaa   3480

caggaggcac ggcaaatacg cagactctgg gcttcagcca aggtgggcct aatacaatgg   3540

ccaatcaggc aaagaactgg ctgccaggac cctgttaccg ccaacaacgc gtctcaacga   3600

caaccgggca aaacaacaat agcaactttg cctggactgc tgggaccaaa taccatctga   3660

atggaagaaa ttcattggct aatcctggca tcgctatggc aacacacaaa gacgacgagg   3720

agcgtttttt tcccagtaac gggatcctga tttttggcaa acaaaatgct gccagagaca   3780

atgcggatta cagcgatgtc atgctcacca gcgaggaaga aatcaaaacc actaaccctg   3840

tggctacaga ggaatacggt atcgtggcag ataacttgca gcagcaaaac acggctcctc   3900

aaattggaac tgtcaacagc cagggggcct tacccggtat ggtctggcag aaccgggacg   3960

tgtacctgca gggtcccatc tgggccaaga ttcctcacac ggacggcaac ttccacccgt   4020

ctccgctgat gggcggcttt ggcctgaaac atcctccgcc tcagatcctg atcaagaaca   4080

cgcctgtacc tgcggatcct ccgaccacct tcaaccagtc aaagctgaac tctttcatca   4140

cgcaatacag caccggacag gtcagcgtgg aaattgaatg ggagctgcag aaggaaaaca   4200

gcaagcgctg gaaccccgag atccagtaca cctccaacta ctacaaatct acaagtgtgg   4260

actttgctgt taatacagaa ggcgtgtact ctgaaccccg ccccattggc acccgttacc   4320

tcacccgtaa tctgtaattg cctgttaatc aataaaccgg ttgattcgtt tcagttgaac   4380

tttggtctct gcg                                                      4393
```